United States Patent
Guo et al.

(10) Patent No.: US 10,718,711 B1
(45) Date of Patent: Jul. 21, 2020

(54) FIBER OPTIC SENSING APPARATUS, SYSTEM, AND METHOD OF USE THEREOF

(71) Applicant: JINAN UNIVERSITY, Guangzhou (CN)

(72) Inventors: Tuan Guo, Guangzhou (CN); Christophe Caucheteur, Guangzhou (CN); Fu Liu, Guangzhou (CN); Xuejun Zhang, Guangzhou (CN); Shunshuo Cai, Guangzhou (CN)

(73) Assignee: JINAN UNIVERSITY, Guangzhou (CN)

(*) Notice: Subject to any disclaimer, the term of this patent is extended or adjusted under 35 U.S.C. 154(b) by 0 days.

(21) Appl. No.: 16/382,186

(22) Filed: Apr. 11, 2019

(51) Int. Cl.
| | |
|---|---|
| *G01J 4/00* | (2006.01) |
| *G01N 21/552* | (2014.01) |
| *G01N 21/31* | (2006.01) |
| *G01N 33/00* | (2006.01) |

(52) U.S. Cl.
CPC .......... *G01N 21/553* (2013.01); *G01N 21/31* (2013.01); *G01N 33/005* (2013.01); *G01N 33/0054* (2013.01); *G01N 33/004* (2013.01); *G01N 33/0044* (2013.01); *G01N 33/0047* (2013.01); *G01N 2201/0846* (2013.01)

(58) Field of Classification Search
CPC ............... G01N 21/211; G01N 21/21; G01N 2021/213; G01J 4/00; G01B 11/0641
USPC ........................................................ 356/369
See application file for complete search history.

(56) References Cited

U.S. PATENT DOCUMENTS

| | | | | |
|---|---|---|---|---|
| 8,554,024 B2* | 10/2013 | Albert | .................... | G01B 11/18 385/12 |
| 2005/0117157 A1* | 6/2005 | Tarsa | ..................... | G01N 21/39 356/437 |
| 2006/0119853 A1* | 6/2006 | Baumberg | ........... | G01N 21/658 356/445 |
| 2008/0007732 A1* | 1/2008 | Ja | ....................... | G01N 21/6428 356/445 |

\* cited by examiner

*Primary Examiner* — Md M Rahman
(74) *Attorney, Agent, or Firm* — Junjie Feng

(57) ABSTRACT

A sensing apparatus, system, and use method for selective detection of a target molecule in a gaseous medium with a limit of detection of less than 50 ppm are provided. The sensing apparatus comprises an optical fiber having a core with a tilted grating, and a coating assembly that is both active to surface plasmon resonance (SPR) and reversibly reactive to the target molecule to allow for repeated detection. Upon a compatible light propagating in the optical fiber, surface plasmon waves at an interface between the coating assembly and the medium can be generated to thereby derive information of the target molecule. Signals from core mode optical waves can additionally be used as inherent reference to remove influences of fluctuations from environmental factors and input power level. There is at least one range of concentrations for the target molecule allowing for linear measurement. Multiplexing of a plurality of sensing apparatuses is also disclosed.

25 Claims, 33 Drawing Sheets

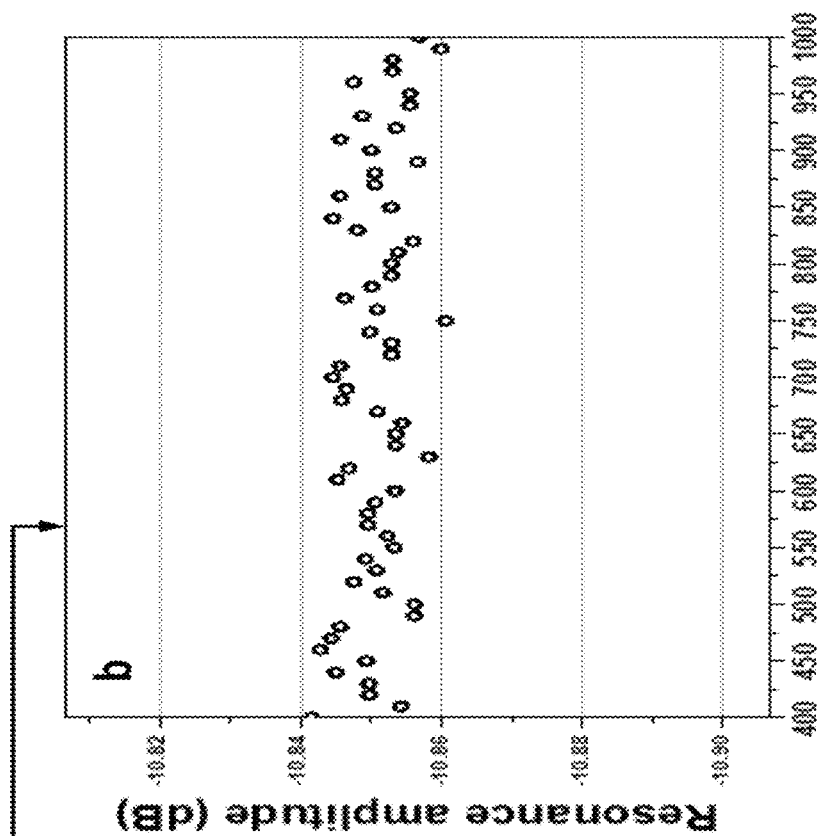
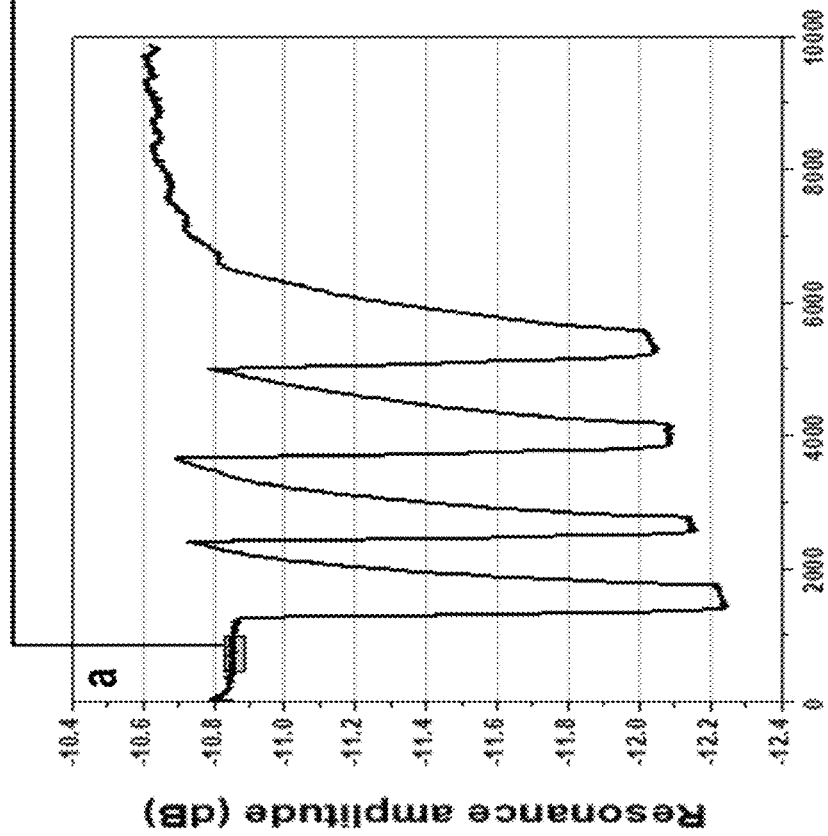
FIG. 15A
FIG. 15B

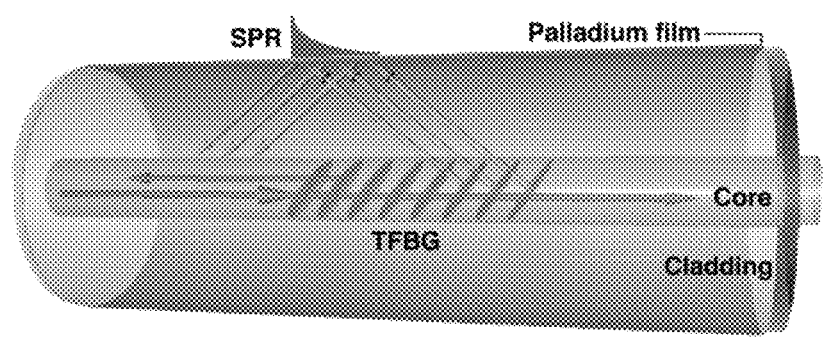
FIG. 16
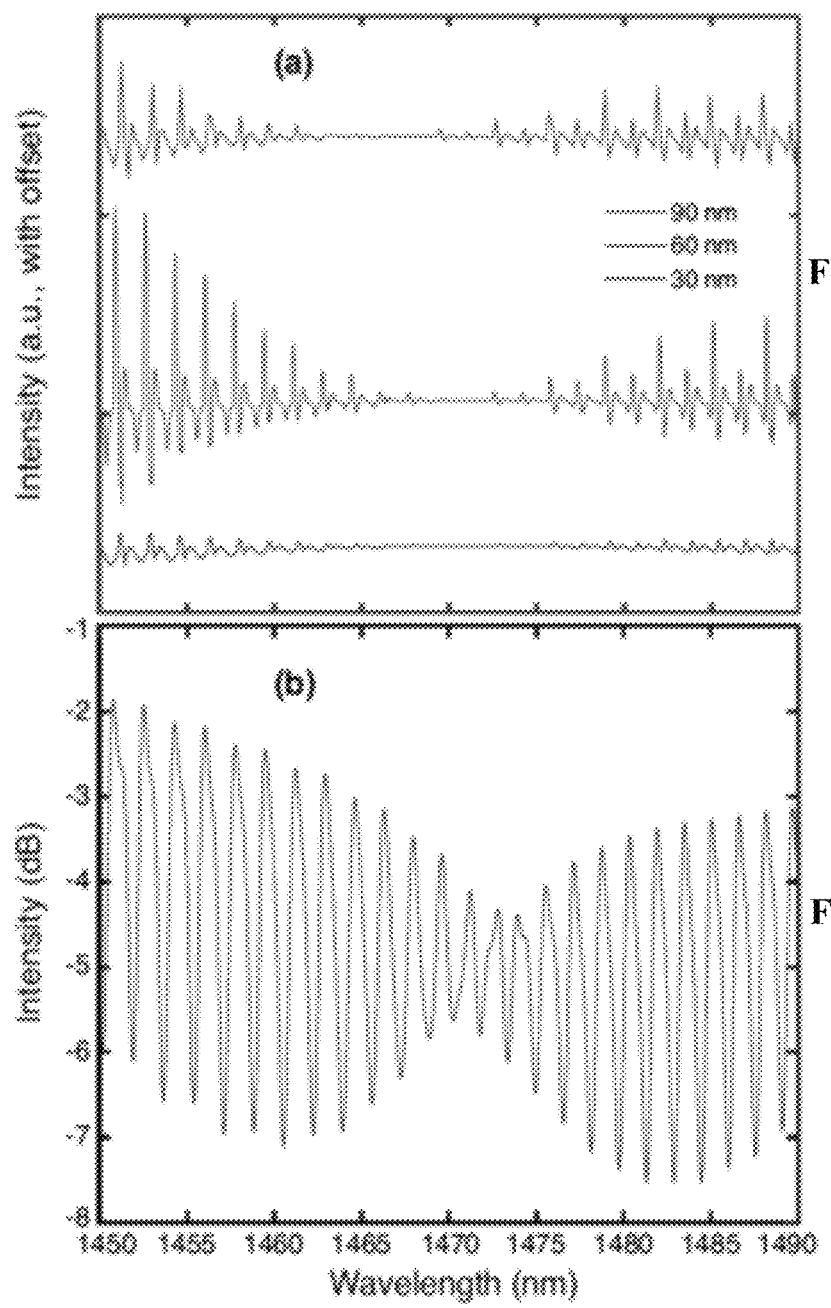
FIG. 17A
FIG. 17B

FIBER OPTIC SENSING APPARATUS, SYSTEM, AND METHOD OF USE THEREOF

TECHNICAL FIELD

This present disclosure relates generally to the field of chemical sensing technologies, and more specifically to a fiber optical sensing apparatus for detecting target molecules in a medium, especially in a gaseous medium.

BACKGROUND

Fiber optical sensors are optical fiber based sensing apparatuses that have been used for a wide variety of purposes, such as in the areas of energy, medicine, scientific research, industrial applications, etc. Such sensors have outstanding advantages, such as intrinsic safety, corrosion resistance, suitability for remote sensing, and immunity to electromagnetic interference.

Fiber optical sensors used for the detection of target chemicals in a liquid medium having a refractory index of more than 1.33, such as in a water solution, has witnessed a great development in the recent years, yet fiber optical sensors used for the detection of molecules in a gaseous medium having a refractory index of around 1.0, remain to be developed.

In the energy field, for example, hydrogen ($H_2$) is a promising energy source for helping supply the energy demands of the world while reducing toxic emissions from fossil fuels. However, it is also a highly flammable and explosive gas at concentrations ranging from 4%-75% in air, with a low ignition energy and high heat of combustion. Thus, it is vital to have an inexpensive device that can quickly, sensitively, reliably and safely monitor hydrogen concentrations in case there is a leak.

In chemical industry, certain gaseous molecules, such as ammonia ($NH_3$), have served as crucial precursors in the manufacturing of other important chemicals including fertilizers, cleaners, food products, and pharmaceutical products, etc. Yet due to its toxicity, ammonia could cause serious environmental problems if leaked, and thus reliable detection of $NH_3$ gas that has been leaked into the atmosphere is also needed.

SUMMARY

In a first aspect, a sensing apparatus is provided, which can be used for the selective detection of a target molecule in a gaseous medium with a limit of detection of less than 50 ppm. The sensing apparatus comprises an optical fiber and a coating assembly coating an outside thereof. The optical fiber comprises a core and a cladding surrounding the core, wherein the core is provided with a tilted grating. The coating assembly is configured to be active to surface plasmon resonance (SPR), and is further configured to be reversibly reactive to the target molecule to allow for repeated detection with high reproducibility. The tilted grating in the core and the coating assembly are configured to generate surface plasmon waves at an interface between the coating assembly and the gaseous medium upon a compatible electromagnetic radiation propagating in the optical fiber, and signals of the surface plasmon waves contain information of the target molecule in the gaseous medium.

Optionally in some embodiments of the sensing apparatus, there is at least one range of concentrations for the target molecule allowing the sensing apparatus to have a linear measurement therein.

Optionally in some embodiments of the sensing apparatus, the optical fiber is further configured to generate other optical waves in the core upon the compatible electromagnetic radiation propagating in the optical fiber, and the sensing apparatus is capable of reliably characterizing the target molecule in the gaseous medium with only minimal influence from fluctuations in certain factors based on the signals of the surface plasmon waves and using signals of the other optical waves as an inherent reference.

In some embodiments of the sensing apparatus, the coating assembly comprises a substrate layer and a reacting layer over an outer surface of the substrate layer. The substrate layer coats the cladding of the optical fiber, and is configured to be active to SPR and insensitive to the target molecule, whereas the reacting layer comprises a composition sensitive to the target molecule.

Herein the target molecule can be hydrogen, and the sensing apparatus according to some specific embodiments is configured for the detection of hydrogen in a gaseous medium, such as air. As such, the reactive layer can comprise palladium (Pd).

Optionally, the substrate layer can comprise at least one of gold (Au) or silver (Ag), and can have a thickness in a range of approximately 20-50 nm; and the reactive layer can comprise a palladium thin film having a thickness in range of approximately 3-15 nm.

Preferably, the substrate layer comprises a gold thin film having a thickness in a range of approximately 25-40 nm; the reactive layer comprises a palladium thin film having a thickness in a range of approximately 5-9 nm; and the internal tilt angle of the grating is at least approximately 20 degrees.

Herein the target molecule can be ammonia, and the sensing apparatus according to some embodiments is configured for the detection of ammonia in a gaseous medium, such as air. As such, the reactive layer can have a composition of at least one of an inorganic material which is selected from a group consisting of tin oxide ($SnO_2$), zinc oxide (ZnO), tungsten oxide ($WO_3$), titanium oxide ($TiO_2$), and iron oxide ($Fe_2O_3/Fe_3O_4$), or an organic material, which is selected from a group consisting of polyaniline, polypyrrole, and metal phthalocyanines.

Optionally, the substrate layer can comprise a gold thin film having a thickness in a range of approximately 40-60 nm; the reactive layer can comprise a polyaniline nanocomposite decorated $SnO_2$ thin film having a thickness of approximately 20-30 nm; and an internal tilt angle of the grating can be at least approximately 20 degrees.

In addition to hydrogen and ammonia, other gaseous target molecules can include methane ($CH_4$), hydrogen sulfide ($H_2S$), carbon monoxide (CO), etc.

In some other embodiments of the sensing apparatus, the coating assembly consists of one single film layer comprising a composition that is both active to SPR and sensitive to the target molecule.

Herein the target molecule can be hydrogen, and the sensing apparatus according to some embodiments is configured for the detection of hydrogen in the gaseous medium, such as air. As such, the coating assembly can include one single palladium film layer having a thickness in a range of approximately 40-70 nm; and an internal tilt angle of the grating can be at least approximately 6 degrees.

In yet some other embodiments of the sensing apparatus, the coating assembly comprises a substrate layer coating the cladding of the optical fiber, configured to be active to SPR and insensitive to the target molecule, and the substrate layer is provided with a modified outer surface exposed to the gaseous medium, configured to sensitive to the target molecule.

Herein the target molecule can be ammonia, and the sensing apparatus according to some embodiments is configured for the detection of ammonia in the gaseous medium, such as air. As such, the substrate layer can comprise at least one of gold (Au) or silver (Ag), and has a thickness in a range of approximately 30-70 nm; and the modified outer surface of the substrate layer can comprise $SnO_2$ nanoparticles.

In a second aspect, a sensing system comprising a sensing apparatus according to any one the embodiments described above is further provided. The sensing system comprises a sensing apparatus, a light source apparatus, and a signal detection apparatus. The light source apparatus is optically coupled to a first end of, and configured to provide an input light into, the sensing apparatus so as to allow the electromagnetic radiation to propagate in the core of the optical fiber of the sensing apparatus. The signal detection apparatus is coupled to the sensing apparatus and is configured to obtain the signals of the surface plasmon waves therefrom so as to derive the information of the target molecule in the medium.

According to some embodiments, the light source apparatus comprises a light source, a polarizer, and a polarization controller, which are sequentially along an optical pathway into the optical fiber of the sensing apparatus, arranged such that the input light emitted from the light source becomes a polarized light having a polarization direction substantially parallel to an inscription direction of the grating in the core of the optical fiber.

In some embodiments of the sensing system, the light source comprises a broadband source (BBS), and the signal detection apparatus comprises an optical spectrum analyzer (OSA).

In some other embodiments of the sensing system, the light source comprises a tunable laser (TLS). The signal detection apparatus includes an optical detector and an analog-to-digital converter. The optical detector is configured to detect, and to convert into analog electrical signals, the signals of the plasmon waves from the sensing apparatus. The analog-to-digital converter is configured to convert the analog electrical signals into digital electrical signals.

According to a transmission-mode sensing system, the signal detection apparatus is coupled to a second end of the optical fiber, wherein the second end is opposing to the first end of the optical fiber to which the light source apparatus is coupled, and thus the signals received by the signal detection apparatus is substantially optical waves transmitted through the second end of the optical fiber.

Herein optionally, the sensing system further comprises at least one other sensing apparatus, each having a second optical fiber, wherein the second optical fiber in the each of the at least one other sensing apparatus is optically connected to one another in series and is further connected in series to a beginning end of the optical fiber of the sensing apparatus to thereby share a common electromagnetic radiation propagation pathway. The signal detector is configured to differentially obtain signals of the surface plasmon waves from the sensing apparatus and each of the at least one other sensing apparatus.

According to a reflection-mode sensing system, the signal detection apparatus is coupled to the first end of the optical fiber, i.e., the signal detection apparatus and the signal detection apparatus are at a same side of the sensing apparatus and are coupled both to the first end of the optical fiber.

As such, a second end of the optical fiber is provided with a mirror having a reflection surface facing to, configured to reflect the electromagnetic radiation back towards, the first end of the optical fiber. The sensing system further comprises a coupler, which is arranged between the light source apparatus and the sensing apparatus along an input optical pathway and between the sensing apparatus and the signal detection apparatus along an output optical pathway. The coupler is configured to separate the input optical pathway and the output optical pathway to thereby allow the signal detection apparatus to obtain the signals of the surface plasmon waves from the sensing apparatus without being influenced by the input light.

In a third aspect, a method for selectively detecting a target molecule in a medium utilizing the aforementioned sensing system is further provided. The method comprises:

providing a sensing system;

arranging the sensing apparatus such that the coating assembly thereof exposes to the medium;

switching on the light source apparatus to provide an input light into the sensing apparatus;

obtaining, by means of the signal detection apparatus, signals of surface plasmon waves produced on the interface between the coating assembly and the medium upon excitement by the input light; and analyzing the signals of the surface plasmon waves to thereby derive the information of the target molecule in the medium.

According to some embodiments, the step of obtaining, by means of the signal detection apparatus, signals of surface plasmon waves produced on the interface between the coating assembly and the medium upon excitement by the input light comprises: obtaining, by means of the signal detection apparatus, signals of the surface plasmon waves and signals of other optical waves in the core. The step of analyzing the signals of the surface plasmon waves to thereby derive the information of the target molecule in the medium comprises: analyzing the signals of the surface plasmon waves and the signals of the other optical waves to thereby derive the information of the target molecule in the medium.

According to some embodiments, the light source apparatus comprises a broadband source (BBS), and the signal detection apparatus comprises an optical spectrum analyzer (OSA). As such, in the method, the step of switching on the light source apparatus to provide an input light into the sensing apparatus comprises: switching on the broadband source (BBS) to provide an input light with a broadband into the sensing apparatus. Correspondingly, the step of analyzing the signals of the surface plasmon waves comprises: performing a spectral interrogation over the signals of the surface plasmon waves to quantify a wavelength shift and optical intensity change induced by a refractive index change of the sensing apparatus so as to derive information of the target molecule in the gaseous medium.

According to some embodiments of the method, in the step of providing a sensing system, the sensing apparatus is determined to have a first wavelength of light that, upon being inputted into the sensing apparatus, produces a most sensitive mode of the plasmon waves, the light source apparatus comprises a tunable laser (TLS), and the signal detection apparatus comprises an optical detector and an analog-to-digital converter. As such, the step of switching on the light source apparatus to provide an input light into the sensing apparatus comprises: switching on the tunable laser (TLS) such that an input light having a second wavelength matching the first wavelength is produced and emits into the sensing apparatus. The step of obtaining, by means of the signal detection apparatus, signals of surface plasmon waves comprises the sub-steps of converting, by means of the optical detector, the signals of the surface plasmon waves from the sensing apparatus into analog electrical signals; and converting, by means of the analog-to-digital converter, the analog electrical signals into digital electrical signals. The step of analyzing the signals of the surface plasmon waves to thereby derive the information of the target molecule in the medium comprises: performing an interrogation over a quantification of intensity variations to thereby derive the information of the target molecule in the medium based on the digital electrical signals.

According to some embodiments, the sensing system comprises more than one sensing apparatus, optically connected to one another in series and each comprising an optical fiber sharing a common electromagnetic radiation propagation pathway. As such, in the method, the step of obtaining, by means of the signal detection apparatus, signals of surface plasmon waves produced on the interface between the coating assembly and the medium upon excitement by the input light comprises: differentially obtaining, by means of the signal detection apparatus, signals of surface plasmon waves from each of the more than one sensing apparatus. The step of analyzing the signals of the surface plasmon waves comprises: differentially analyzing the signals of the surface plasmon waves from the each of the more than one sensing apparatus.

BRIEF DESCRIPTION OF THE DRAWINGS

(FIG. 6A) Experimental transmission spectrum in air for a 23° tilted fiber Bragg grating (TFBG) in standard single mode optical fiber with 30 nm of gold deposited on the cladding surface and the input light polarized linearly along the vertical axis, i.e. p-polarized relative to the tilt direction (see inset for orientations). (FIG. 6B) Simulated electric field intensity distributions of three hybrid plasmonic cladding modes located within the SPR bandwidth. These modes have effective indices near 1.0 and between 5 and 30% of their total power propagating within a 2 m thick layer above the gold surface. (FIG. 6C) Reflective TFBG-SPR sensing system: a tilted grating is inscribed in the core of a standard single mode fiber by exposure to intense ultraviolet irradiation through a phase mask; a thin metal coating is deposited on the fiber cladding and an additional gold coating (or broadband chirped fiber Bragg grating) is added downstream of the TFBG to reflect the whole incident spectrum through the grating and towards the interrogation system. For a given grating period and light wavelength the cladding modes coupled from the core by the grating will be phase matched with surface plasmons propagating along the outside metal surface. (FIG. 6D) Photograph of configuration for gold-coated fiber-optic sensing probe;

(FIG. 9A) and (FIG. 9B) show how the selected mode resonance shifts in spectrum with increasing thickness of Pd; (FIG. 9C) wavelength and peak-to-peak amplitude change of the 1310 nm resonance as a function of deposition time and (FIG. 9D) the simulated Pd film thickness;

(FIG. 11A) Typical simulated response of the 1310 nm resonance to changes in the complex permittivity of a 7 nm thick Pd film on top of the 30 nm thick gold coating; (FIG. 11B) Peak-to-peak amplitude of the 1310 nm resonance as a function of the fractional change in refractive index for 4 values of the Pd thickness;

(FIG. 13A) Reflection spectrum of a 30 nm-Au coated TFBG and scanning electron micrograph of a cross-section of the gold film at the fiber surface; (FIG. 13B) Same as (FIG. 13A) but for the TFBG with an additional 7 nm thick layer of Pd. The SPR attenuation spectrum is shown as the shaded area in both spectra; (FIG. 13C) AFM of 30 nm gold film over optical fiber (fabricated by magnetron sputtering);

(FIG. 14A) Magnitude of the Poynting vector for the radially polarized SPR-cladding mode near the cladding surrounding boundary. (FIG. 14B) Measured reflected spectrum near the 1312 nm resonance as a function of $H_2$ concentration. (FIG. 14C) Measured wavelength and (FIG. 14D) peak-to-peak amplitude change of the 1312 nm resonance as a function of $H_2$ concentration;

FIGS. 15A-15B respectively show: (FIG. 15A) Response of the 1312 nm resonance amplitude to successive exposure of device to alternating concentrations of 0 and 3% $H_2$. (FIG. 15B) Zoom on the response between 400 and 1000 s showing the response noise;

FIG. 16 illustrates the physical principle of SPR excitation with the palladium coated TFBG according to Embodiment 2 of the disclosure;

FIGS. 17A and 17B respectively show: (FIG. 17A) simulation results showing the mode attenuation corresponding to the SPR region for a TFBG coated with 90, 60 and 30 nm of palladium and (FIG. 17B) measurement of the actual SPR region after 60 nm sputtering deposition;

(FIG. 21A) structure and work principle of the materials coated TFBG; (FIG. 21B) and (FIG. 21C) the detail of the polyaniline-$SnO_2$ hybrid thin film with the scale bar (white strip) are 50 um and 20 um respectively, and (d) the physical model of the p-n junction before and after exposure to ammonia;

DETAILED DESCRIPTION OF THE INVENTION

In one aspect, the present disclosure provides an optical fiber-based sensing apparatus that is capable of selectively and sensitively detecting a target molecule in a gaseous medium, such as hydrogen or ammonia in the air.

The sensing apparatus comprises an optical fiber and a coating assembly coating an outside thereof. The optical fiber comprises a core and a cladding surrounding the core, wherein the core is provided with a tilted grating. The coating assembly is configured to be active to surface plasmon resonance (SPR), and is further configured to be reversibly reactive to the target molecule to allow for repeated detection with high reproducibility. The sensing apparatus is configured, primarily through appropriate configurations of the grating (e.g. having an appropriate internal tilted angle, period, and pitch, etc.) and the coating assembly (e.g. having an appropriate composition, thickness, and configuration, etc.), such that upon a compatible electromagnetic radiation propagating in the optical fiber, surface plasmon waves can be generated at an interface between the coating assembly and the gaseous medium, whereas signals of the surface plasmon waves contain information of, and can be analyzed to characterize, the target molecule in the gaseous medium.

The sensing apparatus disclosed herein allows for a sensitive detection of target molecules in the gas medium, which can have a limit of detection (LOD) of at least less than 50 ppm (parts per million), and certain embodiments of the sensing apparatus can have an LOD reaching approximately 10 ppb (parts per billion). The coating assembly in the sensing apparatus is configured to be reversibly reactive to the target molecule to allow for repeated detection with high reproducibility. Depending on embodiments of the sensing apparatus there is at least one range of concentrations for the target molecule allowing the sensing apparatus to have a linear measurement therein, thus greatly facilitating the calibration and measurement. Furthermore, if additional information, for example, core-mode optical waves, can also be taken for the analysis, the sensing apparatus is capable of reliably characterizing the target molecule in the gaseous medium with only minimal influence from fluctuations in certain factors based on the signals of the surface plasmon waves and using signals of the other optical waves as an inherent reference.

Figure 1A:
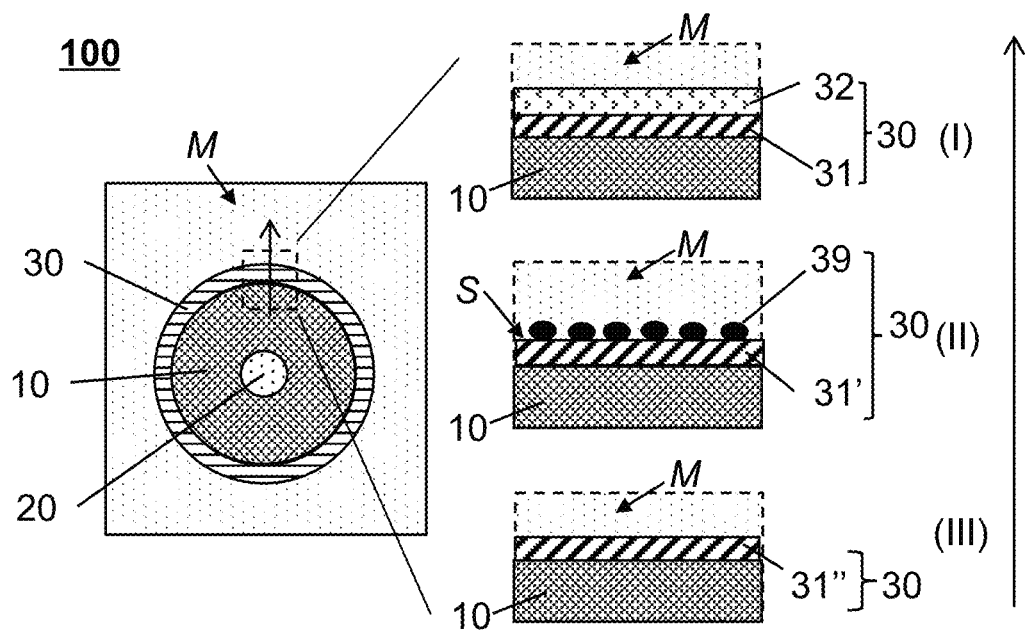
FIGS. 1A and 1B are respectively a cross-sectional view and a perspective view of a sensing apparatus according to some embodiments of the disclosure.
Figure 1B:
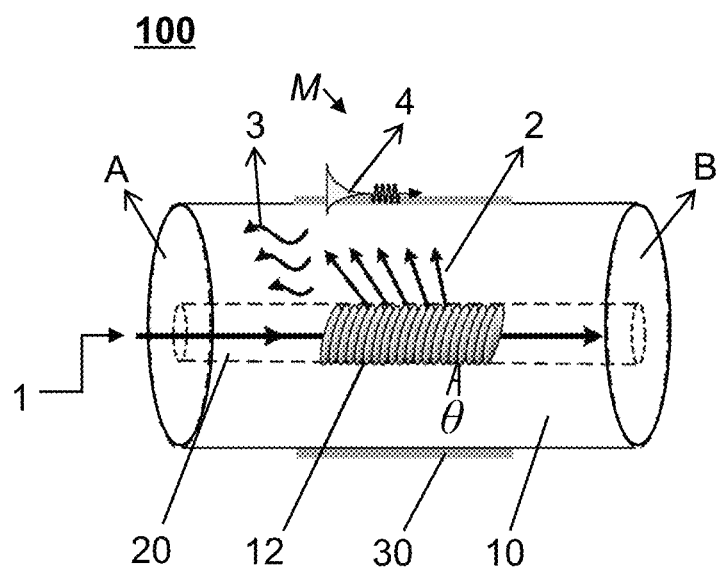

FIGS. 1A and 1B respectively illustrate a cross-sectional view and a perspective view of a sensing apparatus according to some embodiments of the disclosure. As illustrated in FIG. 1A, the sensing apparatus 100 includes a core 20 and a cladding 10, which are arranged coaxially to together form an optical fiber. A coating assembly 30 coats the cladding 10 of the optical fiber, with its outer surface exposing to the medium M.

As further illustrated, the coating assembly 30 can have three different configurations. According to a first configuration (I), the coating assembly 30 comprises two layers: a substrate layer 31 which attaches onto, and coats, the outer surface of the cladding 10, and a reacting layer 32 over the outer surface of the substrate layer 31 and is exposed to the medium M. The substrate layer 31 is configured to be active to SPR and insensitive to the target molecules (not shown) in the medium M. The reacting layer 32 comprises a composition that is sensitive to, and thus reacts with, the target molecule in the medium M Optionally, one or more intermediate layers can be arranged between the cladding 10 and the substrate layer 31, so as to reinforce the attachment between the substrate layer 31 to the outside of the cladding 10 of the optical fiber. Non-limiting examples of the compositions for each of the one or more intermediate layers include germanium (Ge), titanium (Ti), or $TiO_2$, etc.

According to a second configuration (II), the coating assembly 30 comprises only one substrate layer 31' which also coats the outer surface of the cladding 10 and is configured to be SPR active but target molecule insensitive, yet the substrate layer 31 is provided with a modified outer surface S, such as a nanoparticles 39-decorated surface. The nanoparticles 39 are configured to be able to react with the target molecules in the medium M.

According to a third configuration (III), the coating assembly 30 consists of only one single film layer 31", which both coats the cladding 10 of the optical fiber and is exposed to the medium M. The single film layer 31" comprises a composition that is both active to SPR and sensitive to the target molecule.

FIG. 1B illustrates a perspective view, and a working mechanism of the sensing apparatus shown in FIG. 1A. As illustrated, the core 20 of the optical fiber is provided with a tilted grating 12, i.e. grating having an internal tilt angle θ (defined as an angle of each plane of the grating relative to a plane that is substantially perpendicular to the axis of the core 20) of more than 0°. Upon an input light 1 entering from a first side surface A into the optical fiber and transmitting substantially along the core 20, the tilted grating 12 can reflect and/or refract the input light into the cladding 10 of the optical fiber (the light such reflected or refracted is shown as 2 in FIG. 1B), exciting plasmon waves 3 in the cladding and surface plasmon waves 4 at an interface between the coating assembly 30 and the medium M.

In addition, the sensing apparatus 100 can also generate optical waves in the core 20 of the optical fiber (i.e. core-mode optical waves, not shown in the above drawings) which, if detected, can be used as an inherent reference when doing the analysis of the surface plasmon waves 4 to thereby remove the unwanted influence, or interference, due to fluctuations from certain factors, such as those from the environment (e.g. temperature) or those from the sensing system (e.g. light source level). As such, the sensing apparatus 100 disclosed herein can have a feature of be capable of self-calibration.

The sensing apparatus 100 also has a second side surface B opposing to the first side surface A, and could be the light emitting surface (e.g. for a transmission-mode optical fiber), or could be a light reflecting surface (e.g. for a reflection-mode optical fiber). In the latter case, a mirror can be arranged on the second side surface, and will be described below in more detail.

The sensing apparatus 100 as illustrated in FIGS. 1A and 1B can be arranged with a light source apparatus 300 and a signal detection apparatus 200 (e.g. FIG. 2A) to thereby together form a sensing system.

Herein, the optical fiber can have components, compositions, dimensions, and/or configurations of the optical fibers mentioned in any of the embodiments that follow, such as those use for telecommunications-grade optical fiber (e.g. Corning SMF-28), but can also have other parameters.

Herein, the input light 1 as referred to above and illustrated in FIGS. 1A and 1B shall be understood as a suitable electromagnetic radiation emitted by a light source apparatus that can, upon reflection and refraction by the tilted grating, excite or induce the generation of surface plasmon waves 4 at an interface between the coating assembly 30 and the medium M to allow the analysis of the change of refracting indices in the medium M to derive information of the target molecules in the medium M. Preferably the input light 1 can be a polarized light having a polarization direction substantially parallel to an inscription direction (e.g. each plane of the grating 12) of the tilted grating 12 in the core 20 of the optical fiber. Yet a non-polarized light, or a polarized light with a polarization direction other than that perpendicular to the inscription direction of the tilted grating 12 can also be used as the input light 1 to thereby excite the generation of the surface plasmon waves 4.

Herein the target molecule can be a gas molecule, such as hydrogen ($H_2$) or ammonia ($NH_3$), and can also be other gas molecules, such as methane ($CH_4$), hydrogen sulfide ($H_2S$), carbon monoxide (CO), etc. The gaseous medium can be air, or can be a mixture of multiple gases.

Herein, the coating assembly 30 can include a substrate layer coating the cladding 10 of the optical fiber and having a composition that is SPR-active but non-reactive to the target molecule, such as in the configurations I and II of FIG. 1A. An SPR-active composition can be a composition with free electrons available for coupling into surface plasmon waves propagating along the surface of the material. Non-limiting examples of an SPR active composition include: a single material such as a metal (e.g. a noble metal such as Au or Ag), or a conducting metal oxide (e.g. indium tin oxide (ITO), but can also comprise a semiconductor material, a dielectric material, a two-dimensional material, or a mixture of two or more of the above single materials (e.g. an alloy, or a hybrid of a metal and a conducting metal oxide). In addition to having an SPR-active composition, the substrate layer is further configured to have an appropriate thickness that allows for exciting surface plasmon waves 4 at an interface between the coating assembly 30 and the medium M.

Optionally, the substrate layer 31 or 31' can include a thin film having a composition of a noble metal such as Au or Ag, with a thickness in a range of approximately 20-50 nm. Yet according to some embodiments, such as that illustrated in the configuration III in FIG. 1A, the coating assembly 30 can include only one single film layer that is both SPR-active and reactive to the target molecule, such as a palladium (Pd) film layer, having a thickness in a range of approximately 40-70 nm. Such a composition and thickness allows the Pd film layer to generate SPR and to be also reactive to hydrogen molecules. Other examples are also possible.

Furthermore, the coating assembly 30 is also configured to be sensitive or reactive to the target molecule, because of the presence of a reacting layer 32 in configuration I outside the substrate layer 31 and exposing to the medium M, or of the structures 39 on a medium-exposing surface S of the substrate layer 31' in configuration II, or of the dual-functionality single film layer 31" in configuration III. As such, any of the reacting layer 32, the structures 39, or the dual-functionality single film layer 31" in the coating assembly 30 can have a composition sensitive to the target molecule, which can selectively absorb, or react with, the target molecule. Take hydrogen as an illustrating example as the target molecule, compositions sensitive to hydrogen, or hydrogen-sensitive compositions, can include palladium and metallic La—$Mg_2$—Ni. Palladium can selectively absorb hydrogen gas and form the compound palladium hydride (PdHx, where x is the atomic ratio of H:Pd), and the metallic La—$Mg_2$—Ni can absorb hydrogen near ambient conditions and thus forming a hydride $LaMg_2NiH_7$. These chemical changes are associated with volume changes as well as modifications to the real and imaginary part of the metal permittivity. Other examples include a semiconductor material ($SnO_2$, $In_2O_3$).

Other examples include: graphite oxide as a composition sensitive to ammonia, $SnO_2$ as a composition sensitive to methane, According to some embodiments, the reacting layer 32, the structures 39, or the dual-functionality single film layer 31", can be further configured to have a structure with an increased effective surface area, such as a porous structure, a structure with nanoparticles or nanorods on a surface thereof, so as to allow for an increased sensitivity of the sensing apparatus to detect the target molecule in the medium. More preferably, the reacting layer 32, the structures 39, or the dual-functionality single film layer 31", can be further configured to have a periodical structure to thereby allow different sensing apparatuses to have more consensus detection results with less deviations therebetween. The formation of such periodical structure in any of the configurations I, II or III can be, for example, through self-assembly, or through 3D-printing.

In another aspect, the disclosure further provides a sensing system, which comprises a sensing apparatus as mentioned above and is capable of selectively and sensitively detecting a target molecule in a gaseous medium. In addition to the sensing apparatus, the sensing system further comprises a light source apparatus and a signal detection apparatus, which are both optically coupled to the sensing apparatus and configured respectively to provide an input light into the sensing apparatus, and to obtain signals of the surface plasmon waves induced at the medium-coating assembly interface from the sensing apparatus, so as to derive the information of the target molecule in the medium to realize the detection of the target molecule.

Depending on the different working mode, the sensing system has at least two configurations: a transmission mode and a reflection mode.

Figure 2A:
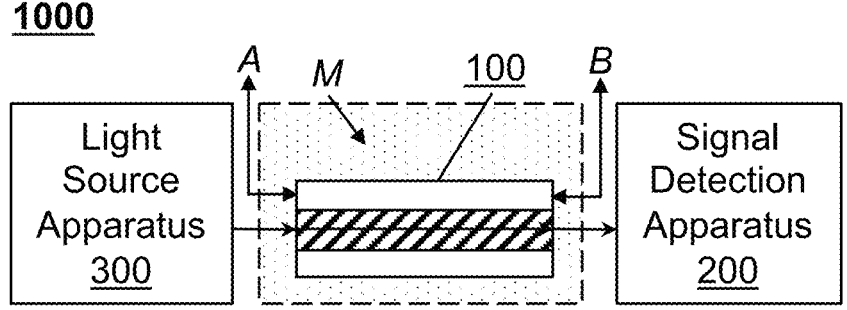
FIG. 2A is a block diagram of a transmission-mode sensing system according to some embodiments of the disclosure.

FIG. 2A is a block diagram of a transmission-mode sensing system according to some embodiments of the disclosure. As shown, the sensing system 1000 includes one sensing apparatus 100, arranged between a light source apparatus 300 and a signal detection apparatus 200 along a direction of light transmission (as shown by the rightward arrows in the figure). In other words, the light source apparatus 300 is optically coupled to a light-incident surface A of the sensing apparatus 100 and thus sends an input light through the light-incident surface A into the optical fiber (as shown by the block with a pattern of inclining lines in FIG. 2A) of the sensing apparatus 100, whereas the signal detection apparatus 200 is optically coupled to a light-emitting surface B of the sensing apparatus 100, and thus receives optical signals (i.e. signal of the SPR waves and core-mode optical waves) transmitted through the light-emitting surface B from the sensing apparatus 100.

Figure 2B:
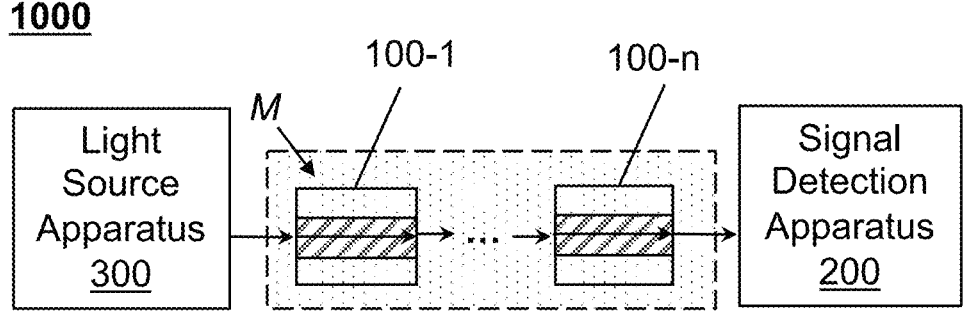
FIGS. 2B-2E are respectively a block diagram of a transmission-mode sensing system having multiplexed sensing apparatuses according to several different embodiments of the disclosure.
Figure 2C:
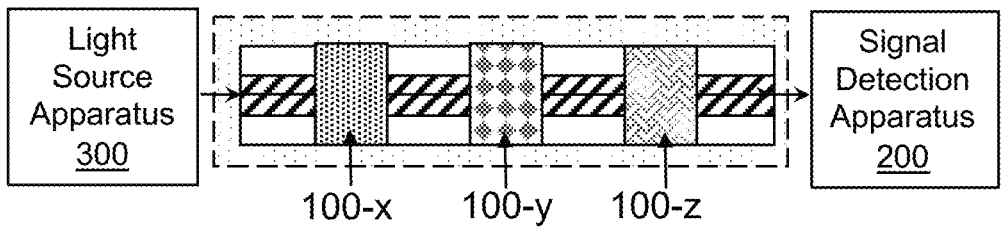

It is noted that the transmission configuration as above allows for multiplexing of more than one sensing apparatus 100 in one single sensing system 1000, in which the optical fibers of the more than one sensing apparatus (100-1, 100-2, . . . , 100-n) share a common light transmission pathway between one single light source apparatus 300 and one single signal detection apparatus 200. According to one embodiments illustrated in FIG. 2B, each of the more than one sensing apparatus (100-1, 100-2, . . . , 100-n) such multiplexed can be configured to have a different reactivity to a different target molecule (T1, T2, . . . , Tn), not shown in the figure) in a common medium M so as to realize simultaneous detection of a variety of different target molecules (T1, T2, . . . , Tn) in the medium Musing one single sensing system 1000. Herein optionally, the more than one sensing apparatus (100-1, 100-2, . . . , 100-n) can share one single optical fiber, yet are configured to have a different coating assembly arranged at a different region on the outside surface of the cladding of the optical fiber along a direction of light transmission in the core, as illustrated in FIG. 2C which shows three sensing apparatuses (100-x, 100-y, and 100-z) arranged on a single optical fiber. Optionally, the more than one sensing apparatus (100-1, 100-2, . . . , 100-n) do not share one single optical fiber, yet are optically connected in series through other optical connecting means (such as an optical connector). There are no limitations herein.

Figure 2D:
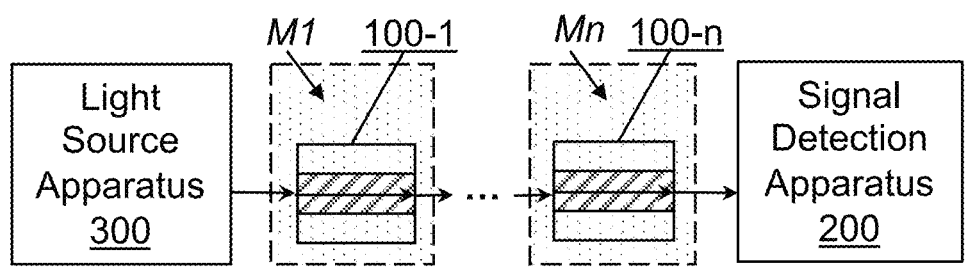

According to some other embodiments illustrated in FIG. 2D, each of the more than one sensing apparatus (100-1, 100-2, . . . , 100-n) such multiplexed can be configured to have a different reactivity to a different target molecule (T1, T2, . . . , Tn), each arranged in a different medium (M1, M2, . . . , Mn) and connected to a commonly shared light source apparatus 300 and a commonly shared signal detection apparatus 200, as such simultaneous detection of different target molecules (T1, T2, . . . , Tn) in different medium (M1, M2, . . . , Mn) can be realized.

Figure 2E:
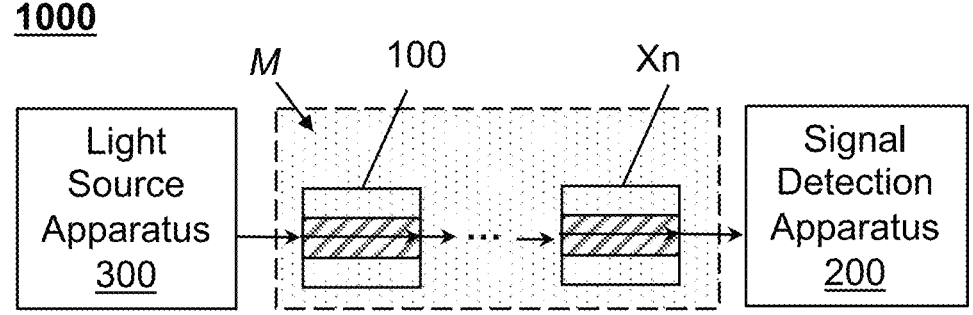

It is noted that in addition to the above embodiments where the more than one sensing apparatus are each configured to detect a target molecule, at least one (Xn) of these multiplexed sensing apparatuses may be configured for detection of a physical property, such as a temperature, a humidity, etc., of a medium M in which the sensing apparatus Xn is disposed. As such, simultaneous detection of a variety of physical and chemical characteristics of the medium by means of one single sensing system 1000 as shown in FIG. 2E having one shared light source apparatus 300 and one shared signal detection apparatus 200 can be realized.

Figure 3A:
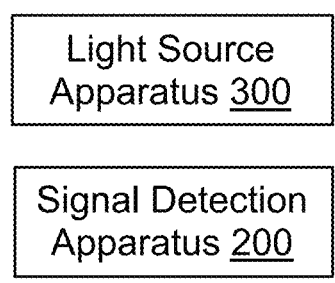
FIG. 3A is a block diagram of a reflection-mode sensing system according to some embodiments of the disclosure.
Figure 3A:
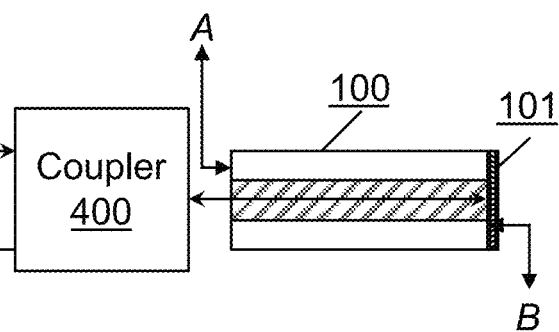

FIG. 3A is a block diagram of a reflection-mode sensing system according to some embodiments of the disclosure. As shown, the light source apparatus 300 and the signal detection apparatus 200 are substantially arranged over a same side of the sensing apparatus 100. Specifically, the light source apparatus 300 and the signal detection apparatus 200 are both optically coupled to a first end A of the optical fiber of the sensing apparatus 100, whereas a second end B is provided with a mirror 101, which has a reflection surface facing to, configured to reflect the light back towards, the first end A of the optical fiber. As such, the first end A is substantially a light-incident surface of the optical fiber, through which the input light provided by the light source apparatus 300 can enter into the optical fiber of the sensing apparatus 100. Then after reflection at the second end B of the optical fiber by the mirror 101, reflected light can transmit back through the first end A to be received by the signal detection apparatus 200.

In order to separate an input optical pathway and an output optical pathway to thereby allow the signal detection apparatus to obtain the signals of the surface plasmon waves from the sensing apparatus without being influenced by the input light, the sensing system 1000 further comprises a coupler 400, which is arranged between the light source apparatus 300 and the sensing apparatus 100 along the input optical pathway and between the sensing apparatus 100 and the signal detection apparatus 200 along the output optical pathway.

Figure 3B:
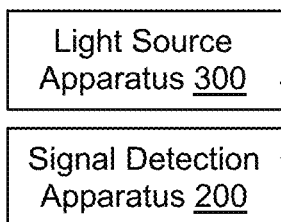
FIG. 3B is a block diagram of a reflection-mode sensing system having multiplexed sensing apparatuses according to some embodiments of the disclosure.
Figure 3B:
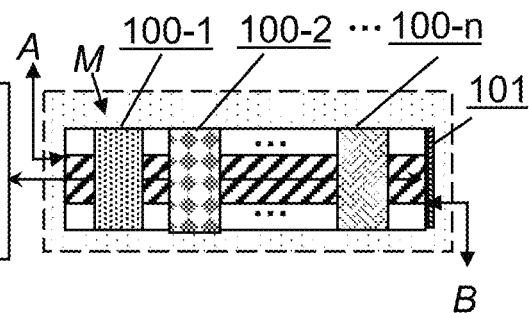

Similar to the transmission-mode sensing system, as illustrated in FIG. 3B, the reflection-mode sensing system can also realize multiplexing of more than one sensing apparatuses, wherein the more than one sensing apparatus 100 can be optically coupled one another in series and connected to the coupler 400.

In any one embodiment of the sensing system 100 described above, the light source apparatus 300 can include a light source, a polarizer, and a polarization controller (PC). Herein the light source can be a broadband source (BBS) or a tunable laser source (TLS). Light emitted from the light source can be converted into a polarized light having a polarization direction substantially parallel to an inscription direction of the tilted grating after the emitted light transmits through the polarizer and the polarization controller.

Figure 4A:
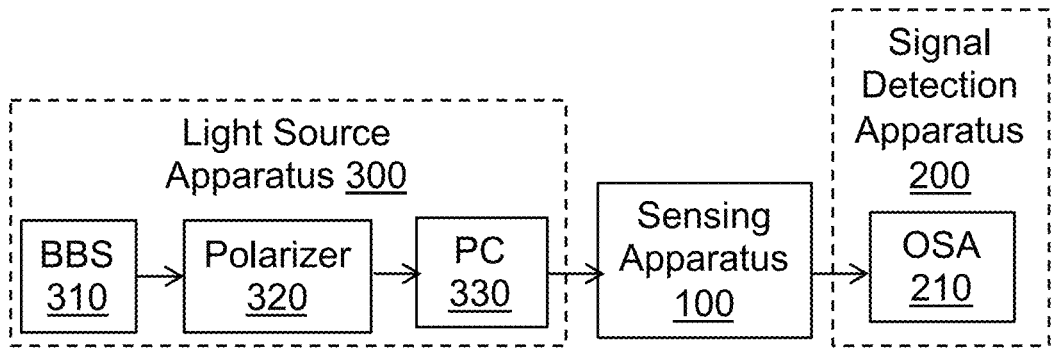
FIGS. 4A and 4B respectively shows a block diagram of a sensing system according to two different embodiments of the disclosure.

According to some embodiments of the sensing system 1000 as illustrated in FIG. 4A, the light source apparatus 300 can include a broadband source (BBS) 310, a polarizer 320, and a polarization controller (PC) 330, and in accordance, the signal detection apparatus 200 comprises an optical spectrum analyzer (OSA) 210. The broadband source (BBS) 310 can provide a broadband input light, which can be converted, via the polarizer 320 and the polarization controller (PC) 330, into a polarized light with aforementioned polarization direction before it enters into the optical fiber of the sensing apparatus so as to excite surface plasmon waves on the surface of the sensing apparatus 100. The optical spectrum analyzer (OSA) 210 is configured to analyze, via a spectral interrogation, the signals of the surface plasmon waves transmitted from the sensing apparatus 100 to quantify a wavelength shift and optical intensity change induced by a refractive index change of the sensing apparatus 100 so as to in turn derive information of, or characterize, the target molecule in the medium.

Figure 4B:
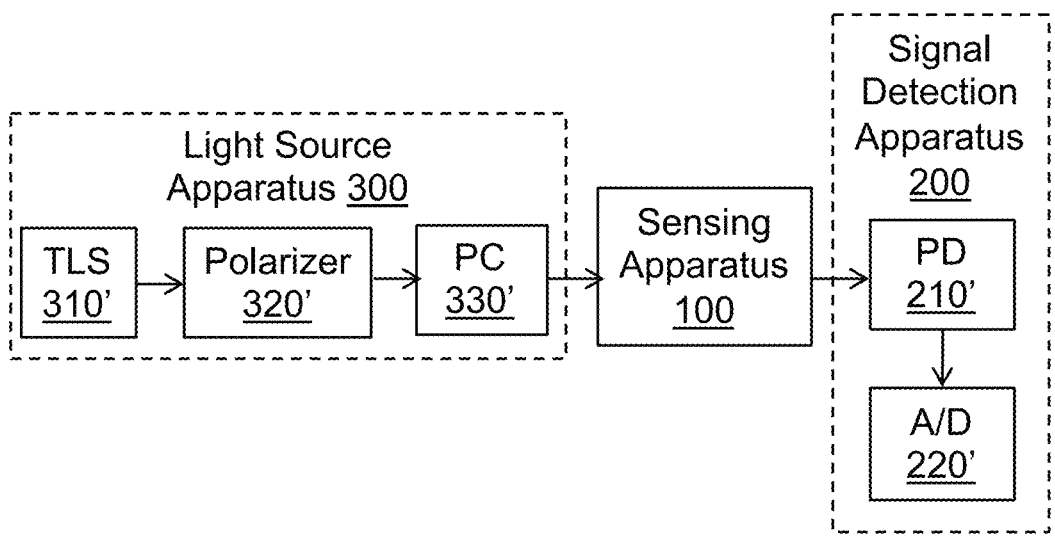

According to some other embodiments of the sensing system 1000 as illustrated in FIG. 4B, the light source apparatus 300 can include a tunable laser source (TLS) 310', a polarizer 320', and a polarization controller (PC) 330', and in accordance, the signal detection apparatus 200 comprises an optical detector (PD) 210' and an analog-to-digital converter (A/D) 220'. The tunable laser source (TLS) 310' is configured to provide an input light with a pre-determined narrow band, such as comprising a light with a second wavelength matching a predetermined first wavelength. A light with the predetermined first wavelength has been determined in advance to be able to produce one of the most sensitive modes of surface plasmon waves on the sensing apparatus, upon being inputted into the sensing apparatus. The pre-determination can be performed utilizing the embodiments of the sensing system as illustrated in FIG. 4A, where the sensing apparatus 100 to be examined is coupled to a broadband source (BBS) 310, a polarizer 320, a polarization controller (PC) 330, and an optical spectrum analyzer (OSA) 210 in a configuration illustrated in FIG. 4A. The broadband source (BBS) 310 is configured to provide a broadband input light, whereas an optical spectrum analyzer (OSA) 210 is configured to analyze at which wavelength the input light can generate one of the most sensitive modes of surface plasmon waves on the sensing apparatus 100.

The input light is further converted, via the polarizer 320' and the polarization controller (PC) 330', into a polarized light with aforementioned polarization direction before it enters into the optical fiber of the sensing apparatus so as to excite surface plasmon waves on the surface of the sensing apparatus 100. The optical detector 210' is configured to detect, and to convert into analog electrical signals, the signals of the plasmon waves from the sensing apparatus 100. The analog-to-digital converter 220' is further configured to convert the analog electrical signals into digital electrical signals, based on which an interrogation can be performed over a quantification of intensity variations to thereby derive the information of the target molecule in the medium.

In yet another aspect of the disclosure, a method for selectively detecting a target molecule in a medium utilizing the aforementioned sensing system is further provided.

Figure 5A:
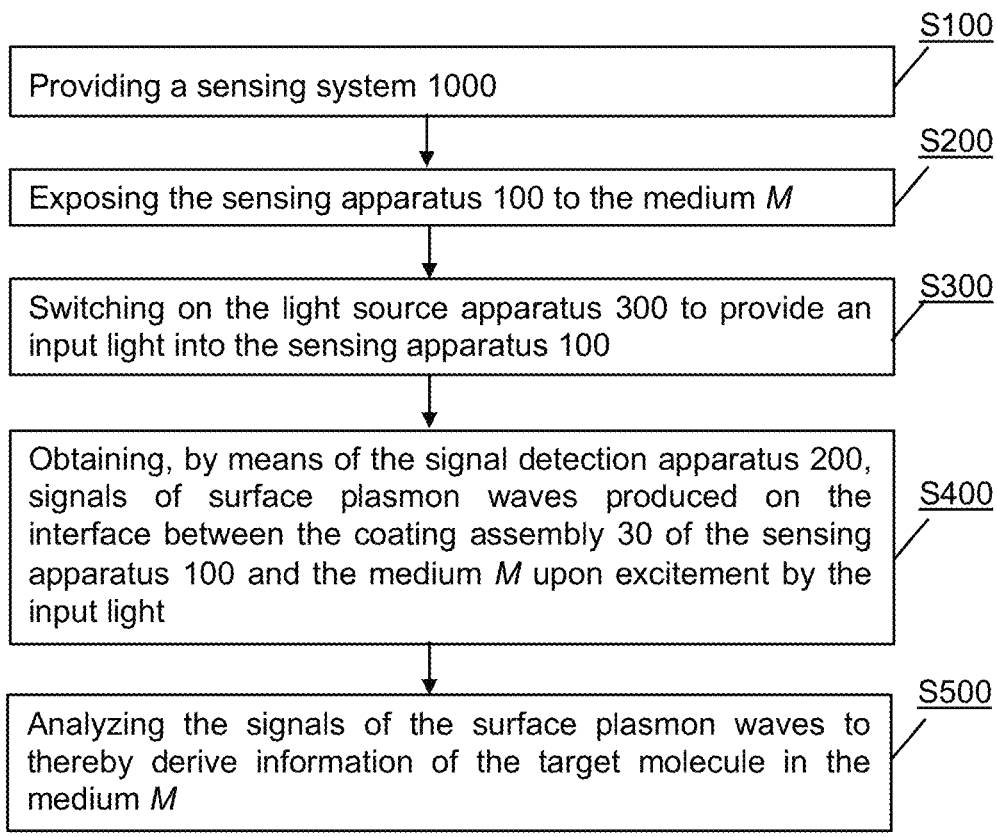
FIGS. 5A-5E respectively illustrate a flow chart of a method of using the sensing system according to different embodiments of the disclosure.

FIG. 5A illustrates a flow chart of the method according to some embodiments of the disclosure. As shown, the method comprises the following steps:

S100: Providing a sensing system 1000;

S200: Exposing the sensing apparatus 100 to the medium M;

S300: Switching on the light source apparatus 300 to provide an input light into the sensing apparatus 100;

S400: Obtaining, by means of the signal detection apparatus 200, signals of surface plasmon waves produced on the interface between the coating assembly 30 of the sensing apparatus 100 and the medium M upon excitement by the input light; and S500: Analyzing the signals of the surface plasmon waves to thereby derive the information of the target molecule in the medium M.

Figure 5B:
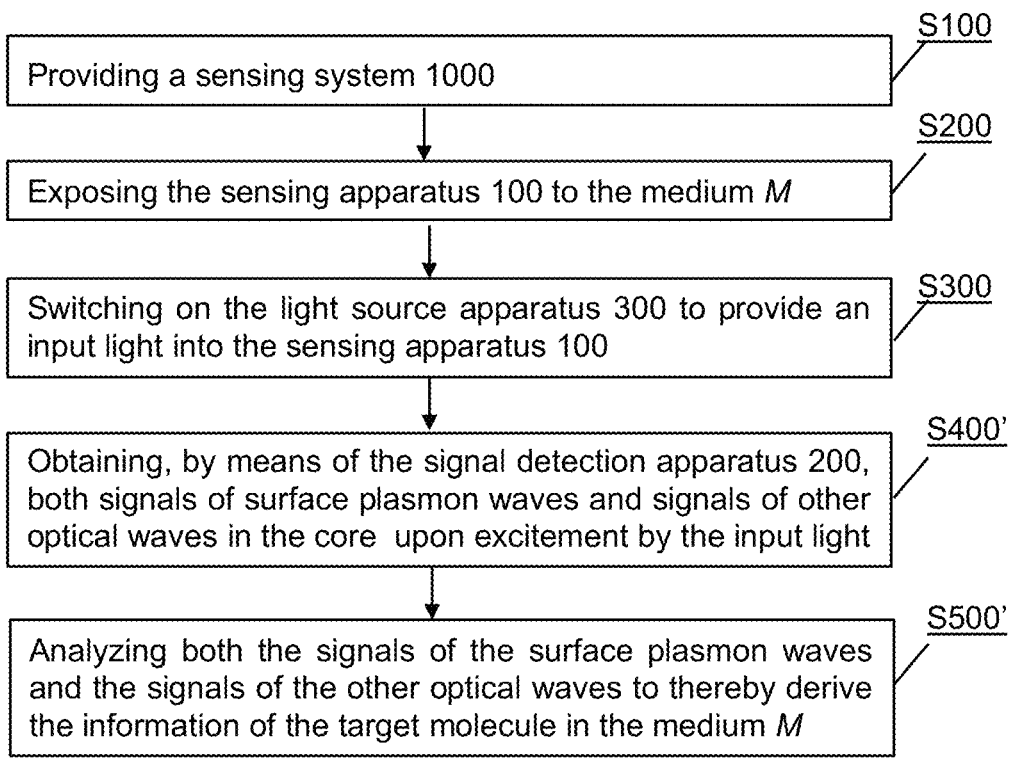

According to some embodiments of the sensing system 1000, the sensing apparatus 100 is configured to be able to generate optical waves in the core 20 of the optical fiber which, if detected, can be used as an inherent reference when doing the analysis of the surface plasmon waves 4 to thereby remove the unwanted influence, or interference, due to fluctuations from certain factors, such as those from the environment (e.g. temperature) or those from the sensing system (e.g. light source level). As such, according to some embodiments of the method illustrated in FIG. 5B, rather than only obtaining signals of signals of surface plasmon waves, step S400 comprises:

S400': Obtaining, by means of the signal detection apparatus 200, both signals of the surface plasmon waves and signals of other optical waves in the core. Accordingly, step S500 comprises:

S500': Analyzing both the signals of the surface plasmon waves and the signals of the other optical waves to thereby derive the information of the target molecule in the medium M.

Figure 5C:
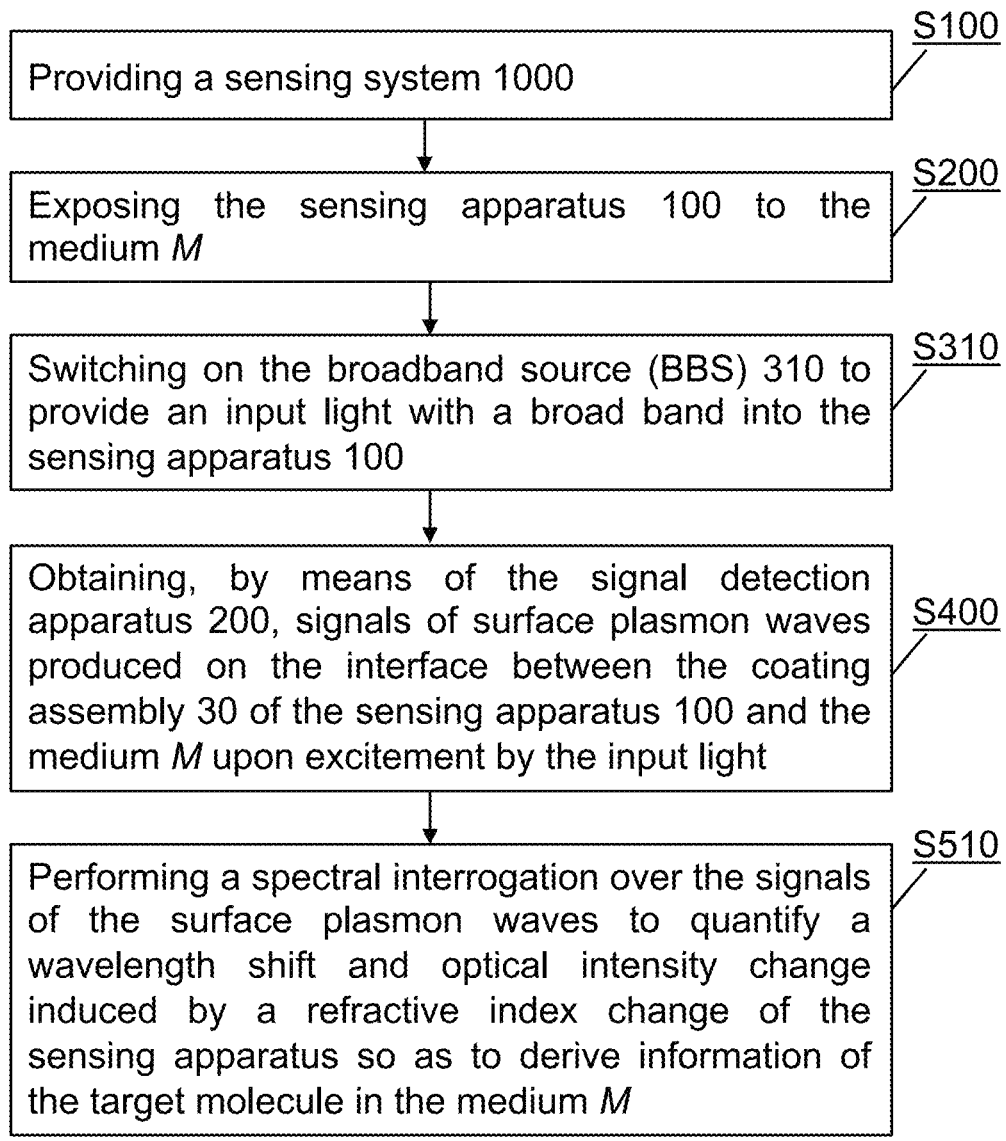

According to some embodiments, the light source apparatus 300 of the sensing system 1000 comprises a broadband source (BBS) 310, and the signal detection apparatus 200 comprises an optical spectrum analyzer (OSA) 210, as illustrated in FIG. 4A. As such, in the embodiments of the method utilizing the sensing system 100 as above, which is illustrated in FIG. 5C, step S300 of switching on the light source apparatus 300 to provide an input light into the sensing apparatus 100 comprises:

S310: Switching on the broadband source (BBS) 310 to provide an input light with a broad band into the sensing apparatus 100.

Further correspondingly, step S500 of analyzing the signals of the surface plasmon waves comprises:

S510: Performing a spectral interrogation over the signals of the surface plasmon waves to quantify a wavelength shift and optical intensity change induced by a refractive index change of the sensing apparatus so as to derive information of the target molecule in the medium M.

Figure 5D:
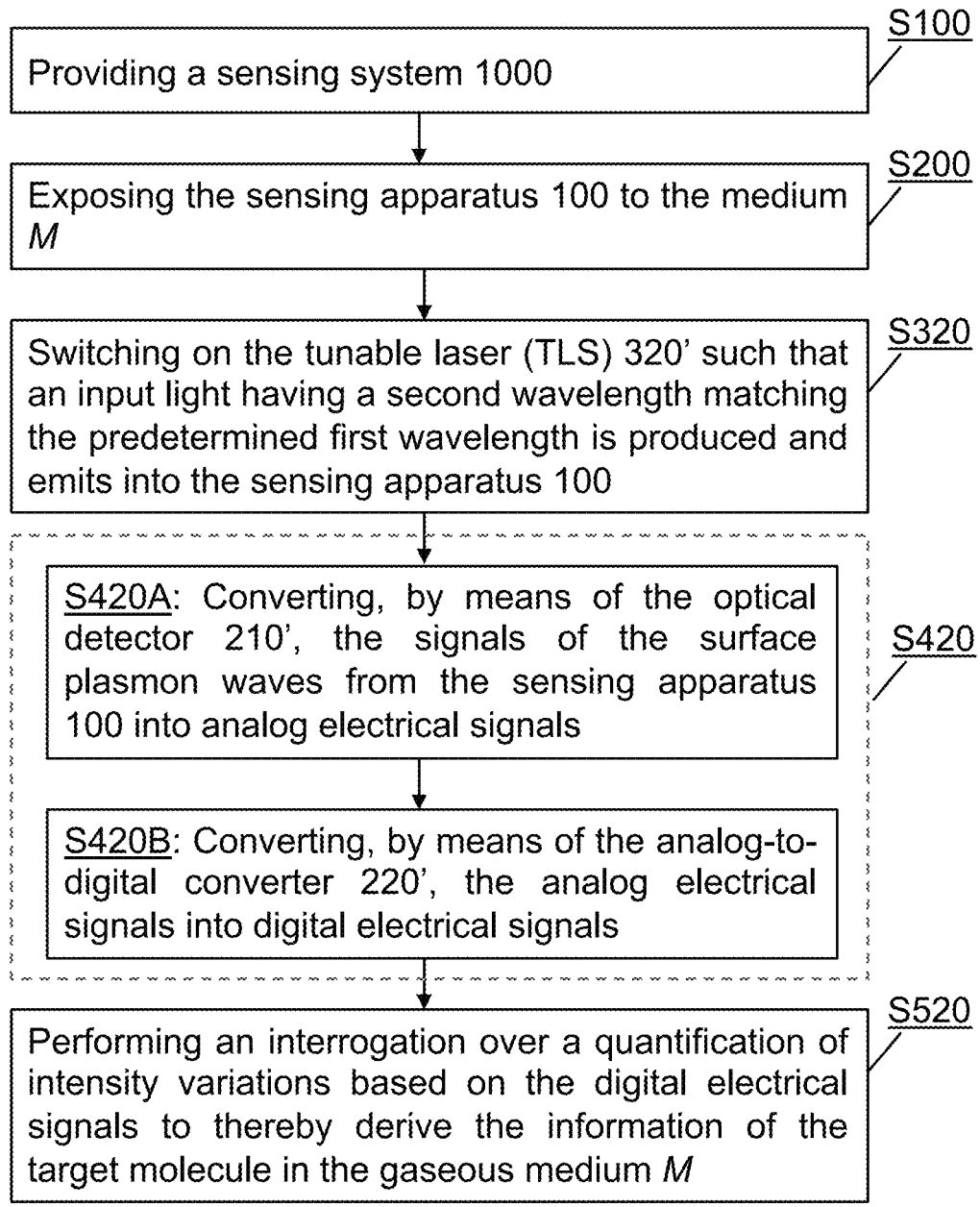

According to some other embodiments, the light source apparatus 300 of the sensing system 1000 comprises a tunable laser source (TLS) 310', and the signal detection apparatus 200 comprises an optical detector (PD) 210' and an analog-to-digital converter (A/D) 220', as illustrated in FIG. 4B. As such, in some embodiments of the method utilizing the sensing system as above, which is illustrated in FIG. 5D, step S300 of switching on the light source apparatus 300 to provide an input light into the sensing apparatus 100 comprises:

S320: Switching on the tunable laser (TLS) such that an input light having a second wavelength matching the pre-determined first wavelength is produced and emits into the sensing apparatus 100.

Correspondingly, step S400 of obtaining, by means of the signal detection apparatus 200, signals of surface plasmon waves produced on the interface between the coating assembly 30 of the sensing apparatus 100 and the medium M upon excitement by the input light comprises:

S420A: Converting, by means of the optical detector 210', the signals of the surface plasmon waves from the sensing apparatus 100 into analog electrical signals; and S420B: Converting, by means of the analog-to-digital converter 220', the analog electrical signals into digital electrical signals.

Further correspondingly, step S500 of analyzing the signals of the surface plasmon waves to thereby derive the information of the target molecule in the gaseous medium M comprises:

S520: Performing an interrogation over a quantification of intensity variations based on the digital electrical signals to thereby derive the information of the target molecule in the gaseous medium M.

Figure 5E:
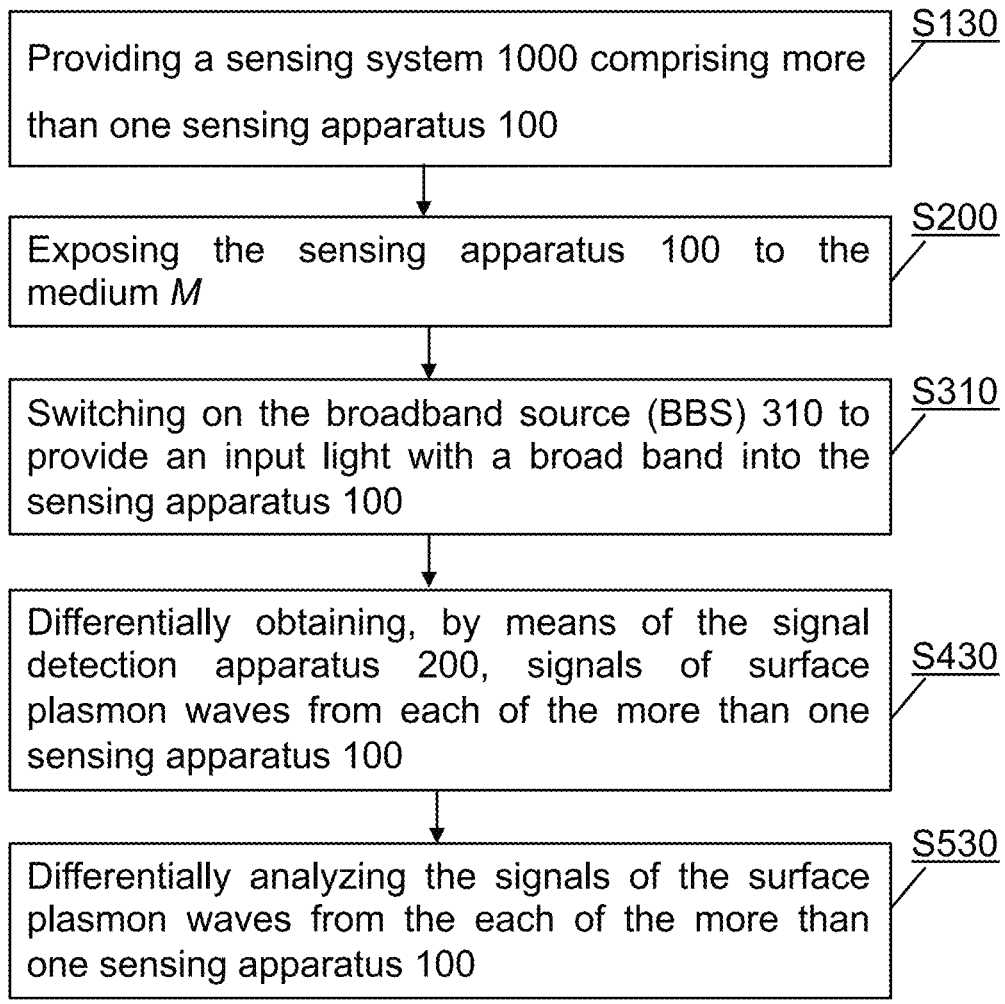

According to some embodiments, the sensing system 1000 comprises more than one sensing apparatus, which are multiplexed (i.e. optically connected to one another in series and each comprising an optical fiber sharing a common electromagnetic radiation propagation pathway), as illustrated in FIG. 2D or FIG. 3B. As such, in embodiments of the method utilizing the sensing system 1000 as above, which is illustrated in FIG. 5E, the step S100 comprises:

S130: Providing a sensing system 1000 comprising more than one sensing apparatus 100;

Correspondingly, the step S400 of obtaining, by means of the signal detection apparatus, signals of surface plasmon waves produced on the interface between the coating assembly and the gaseous medium upon excitement by the input light comprises:

S430: Differentially obtaining, by means of the signal detection apparatus 200, signals of surface plasmon waves from each of the more than one sensing apparatus 100.

Further correspondingly, the step S500 of analyzing the signals of the surface plasmon waves comprises:

S530: Differentially analyzing the signals of the surface plasmon waves from the each of the more than one sensing apparatus 100.

In the following, multiple embodiments are provided for a more detailed illustration of the sensing apparatus, system, and the use method for the detection of target molecules in the gas medium.

Embodiment 1

Embodiment 1 provides an optical fiber-based hydrogen-sensing apparatus with its coating assembly comprising a gold film layer (~30 nm) and a Pd film layer (3-43 nm, and preferably 7 nm). The sensor can be used to selectively detect $H_2$ concentrations between 0 and 3% (by volume) in a gaseous medium. In some embodiments, the tilt angle of the grating is fixed at 23 degrees in order to allow the excitation of surface plasmon resonances on the gold surface by high order cladding modes in air at wavelengths near 1310 nm. Simulations of the grating response based on measurable experimental parameters indicate that for palladium thicknesses between 3 and 10 nm the measured changes in the grating transmission become independent of thickness. Therefore for a 7 nm thick film any change in transmission can be traced directly to changes in permittivity. The relative change of the permittivity of the palladium layer was found to scale linearly with hydrogen concentration with a scaling factor of −0.093/% $H_2$ for hydrogen concentrations between 0 and 1.7%. The limit of detection of the grating configuration used was determined to be 380 ppm at three times the standard deviation for measurements averaged over 80 seconds. Using standard fiber optic instrumentations and single mode fiber, the signal to noise ratio was over 100.

Fiber SPR sensors are a subset of optical fiber sensors that benefit from the high confinement of intense electromagnetic fields at the surface of metal layers deposited on the fiber. Such sensors have been predominantly used in biochemical sensing where the surface sensitivity is a great advantage and where the phase matching of the surface plasmons to propagating fiber modes is facilitated by the fact that the surrounding medium is a liquid with a refractive index relatively close to that of the fiber. Even though Pd is a metal and should be useable for SPR, few such $H_2$ sensors, and especially fiber-based sensors have been reported so far. The reason for this is that the propagation constant of surface plasmons at the metal-air interface is more strongly mismatched to that of light guided in the fiber which makes the coupling of light to the SPR difficult, but also because in order to have the best (narrow and high attenuation) possible SPR the thickness of the metal must be at least several tens of nm, which slows the response time of the Pd to $H_2$ in-diffusion.

To develop this embodiment of the invention, the first step of the process is a combination of simulations and experiments on the effect of Pd thickness on the response TFBG-SPR sensors, since this parameter impacts the response speed and reversibility. Once the optimum thickness is chosen, further simulations are used to correlate the experimentally measured changes in the sensor response upon exposure to various concentrations of $H_2$ with changes in the optical properties of PdHx. The determination of the effect of $H_2$ on Pd can then be used to predict the performance of other similar sensor devices without having to calibrate each sensor individually. Of particular interest is the fact that for TFBG-SPR sensors with 30 nm thick gold coatings operating at wavelengths near 1.3 µm, the response of the sensor becomes insensitive to small changes in Pd thickness when this thickness is between 3 and 10 nm, thereby isolating the effect of $H_2$ ingress to permittivity changes only, which leads to a great simplification of the data analysis. It is important to note that because of the additional layer of Pd and operation at wavelengths near 1300 nm, a 30 nm gold thickness is used here instead of 50 nm. The paper is organized as follows: Section 2 briefly describes the sensor principle and the influence of the Pd thickness on the SPR response, from which an optimum Pd thickness of 7 nm is determined. Section 3 then presents experimental results and simulation support for the relationship between the complex permittivity of PdHx and hydrogen concentration in the range from 0 to 3% (i.e. up to just below the flammability threshold of $H_2$). This important result supports and confirms the fact that there is a linear relationship between concentration and complex permittivity, furthermore that the real and imaginary parts of the permittivity scale by the same amount and finally that the value obtained for the scaling factor conforms to previous partial findings at similar concentrations. The detection limit based on the relatively high signal to noise ratio of the TFBG-SPR device, the sensitivity and the standard deviation of the measurements is also reported. Section 4 summarizes and concludes the results with a discussion of their impact.

2 Methods, Simulations and Optimization 2.1 Simulations

Unlike standard fiber Bragg gratings, the response of TFBGs depends on the state of polarization of the input light launched in the core because the tilt in the grating planes effectively breaks the cylindrical symmetry of the fiber. In particular, when the input core light is p-polarized relative to the inclination plane of the grating fringes, high order cladding modes (with low values of effective indices) have electric fields polarized radially at the cladding surface, i.e. the equivalent of TM polarization in the planar case and thus ideally polarized to excite surface plasmons on metal coatings. The consequence for the grating transmission is a relatively narrow spectral region where the amplitudes of the cladding mode resonances are strongly diminished because of the coupling to a surface plasmon. For the results to be reported here, the fiber used was boron germanium co-doped highly photosensitive single-mode fiber (FIBERCORE PS1250/1500), and gold coated TFBGs were fabricated as reported in ref. (Albert et al., 2013) with a Bragg wavelength of 1543.34 nm for the core mode back reflection. This fiber has been designed to match the mode field diameter characteristics of typical, dual-wavelength, 1310 nm and 1550 nm telecommunications fiber, and it remains single-mode at wavelengths near 1300 nm where SPR effects occur in our sensors when the gold coating is exposed to air or dilute gases.

Figures 6A, 6B:
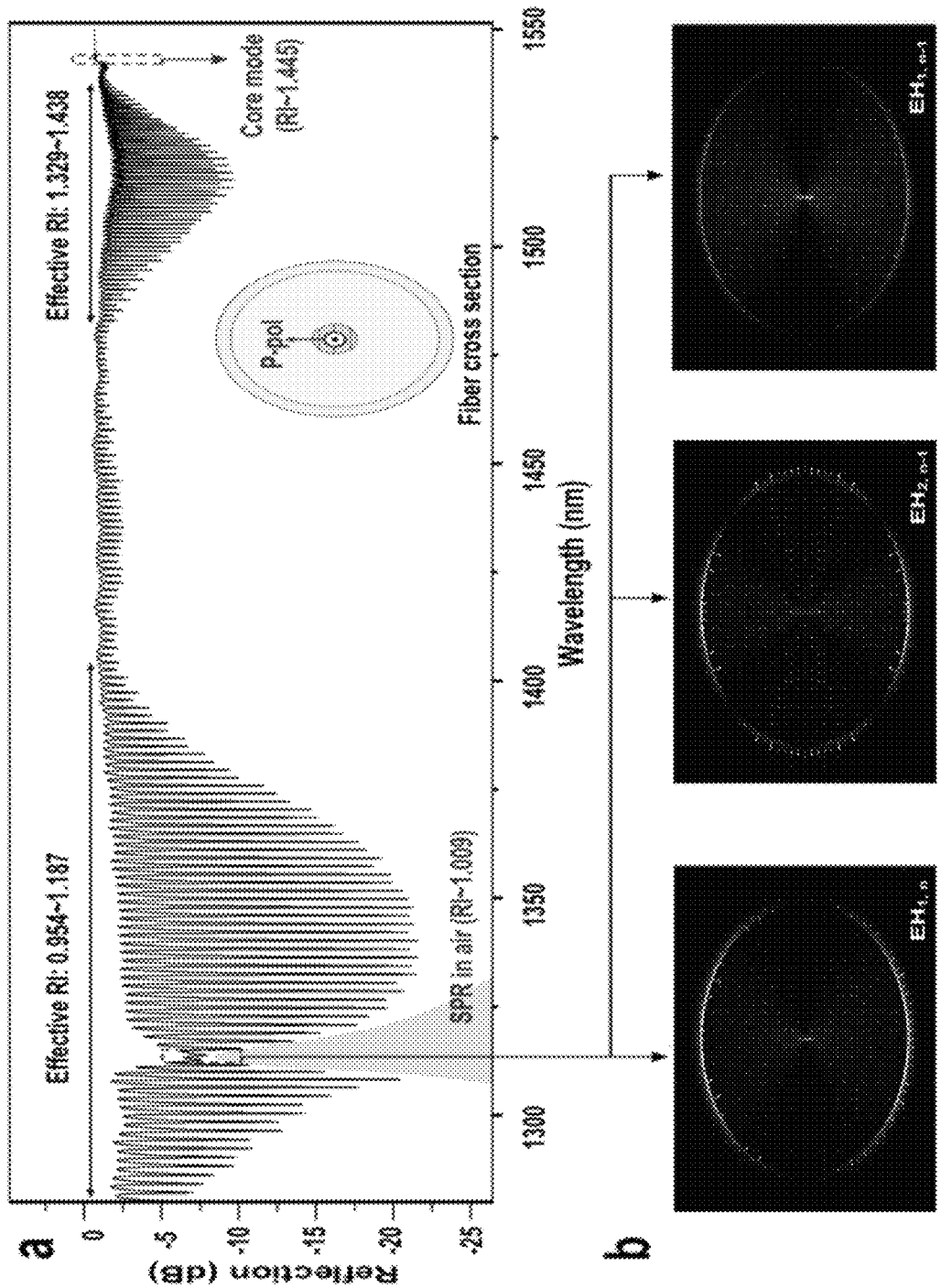
FIGS. 6A-6D respectively show.

FIG. 6A shows a typical experimental transmission spectrum of an 18 mm long, 23-degree tilt TFBG (internal angle relative to the fiber cross section) coated with 30 nm of gold and measured in air with input light p-polarized. The fine comb of cladding mode resonances is more complex than that of TFBGs with smaller tilt angles but a clear SPR signature is observed near 1312 nm. In fact, the tilt angle was chosen so that strong coupling occurs to high order cladding modes with a real part of their effective index close to 1.01, i.e. synchronous with the effective index of the surface plasmon of a gold surface in air at these wavelengths.

Figure 7A:
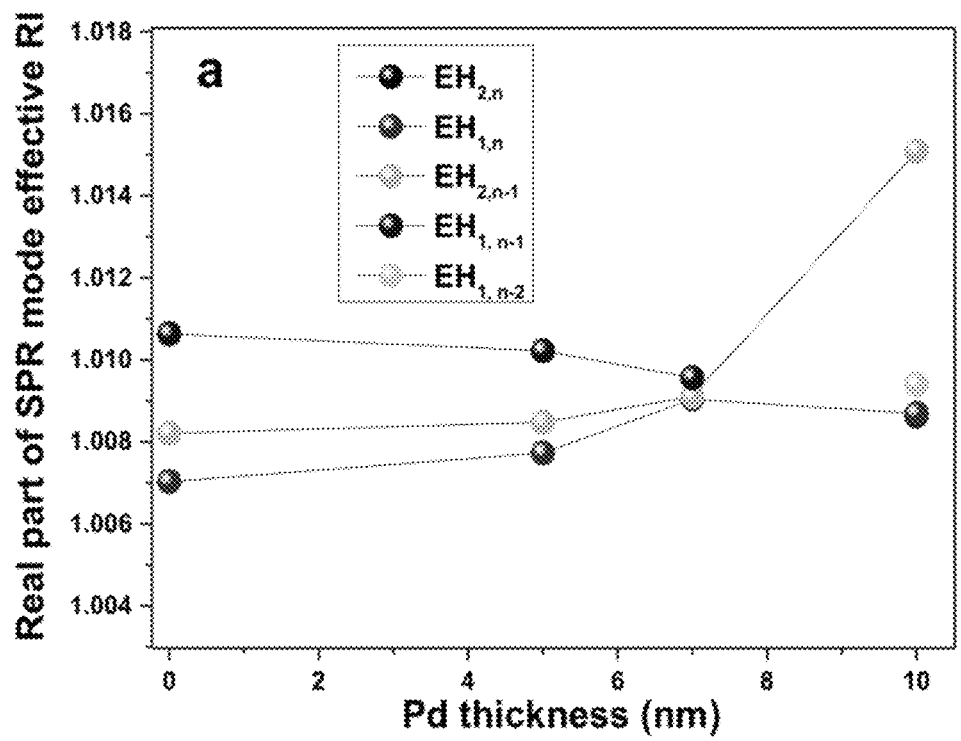
FIGS. 7A and 7B respectively illustrate simulated real part (FIG. 7A) and imaginary part (FIG. 7B) of the effective indices of cladding modes that are phase-matched to the surface plasmon over metal surface in the air.
Figure 7B:
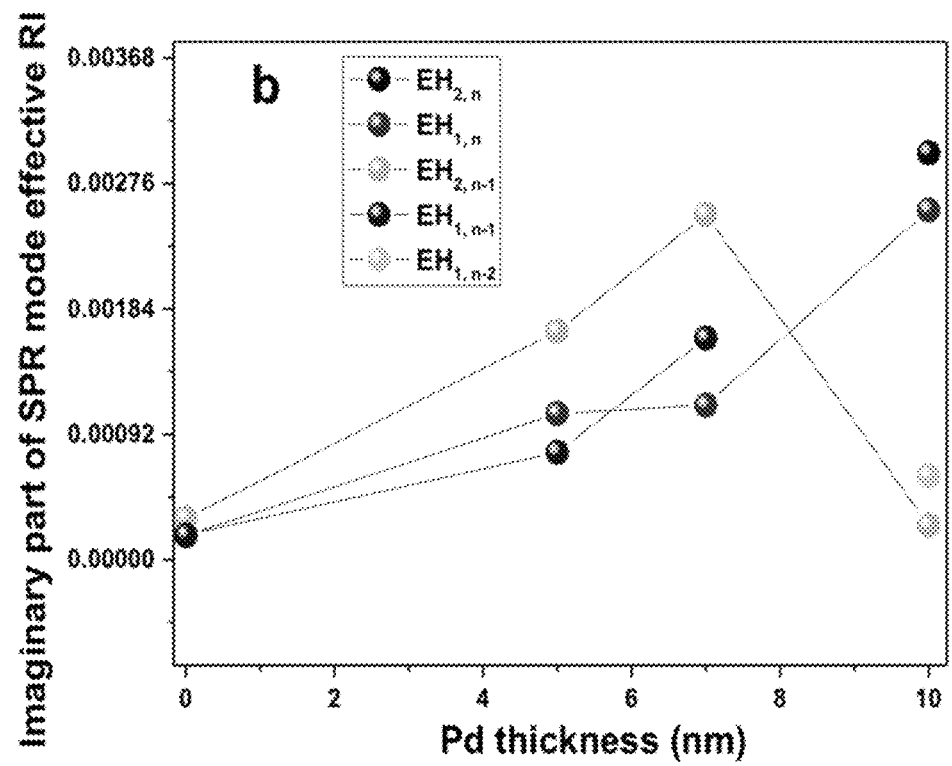

The simulation of the device transmission spectrum is carried out first by solving for the modes of the fiber structure (inclusive of core, cladding, metal layers, and outside medium) with a complex vectorial finite-difference algorithm, and then using coupled mode theory as described in (Erdogan and Sipe, 2008) for the transmission of TFBGs. The simulation parameters were a core radius of 4.1 µm with a refractive index of 1.4545, a cladding radius of 62.5 µm with a refractive index of 1.4467. The gold coating had a thickness of 30 nm and complex refractive index of 0.4538-8.37082i while the Pd layer had an index of 2.7423-7.3407i (Please note the values of refractive index of all solutions and optical fiber materials (core and cladding) was referenced to 1320 nm) and several values of thickness. These simulations first confirm that the real part of the surface plasmon effective index observed experimentally is near 1.009. FIGS. 7A and 7B show the simulated effective indices of the modes most strongly coupled to the surface plasmon, as indicated by the fact that they have the largest imaginary parts: they are $TM_{0n}$, $EH_{1n}$, and $EH_{2n}$ modes and they have a radial order n greater than 160. FIG. 6B further shows the distribution of the mode field power density (i.e. the Poynting vector) over the cross-section of the gold coated fiber for some SPR-active modes, with high field power located just above the cladding surface. As will be shown below, the $EH_{1n}$ mode most strongly coupled to the SPR has a surface power fraction near 47% and hence should be the most sensitive. However, this mode is also so attenuated and weakly coupled to the incident core mode that it actually disappears from the transmission spectrum and is impossible to monitor. The next mode on the short wavelength side is the $TM_{0n}$ mode which has a smaller attenuation and still 11% of power propagating above the fiber surface, and it is the one that will be used for measurement purposes.

Figure 6C:
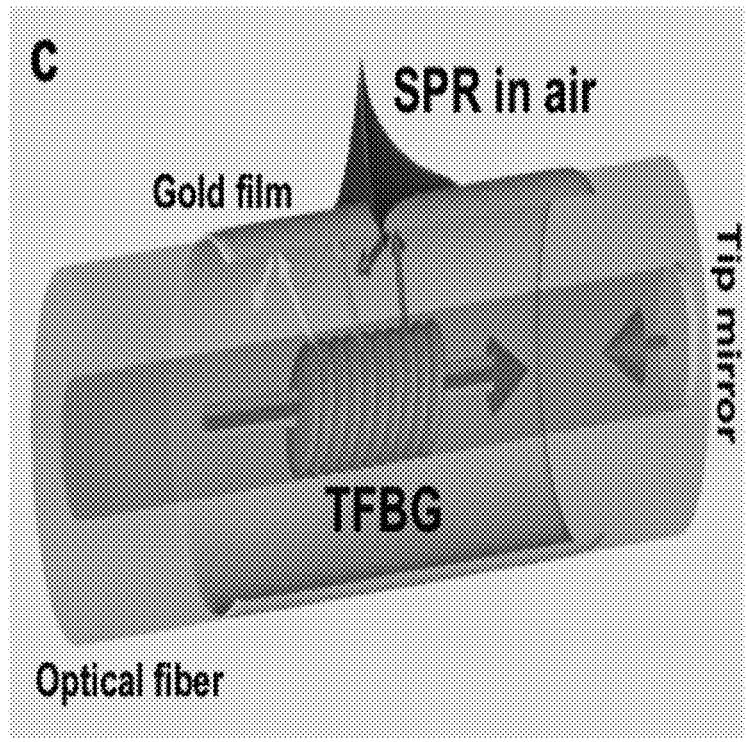
Figure 6D:
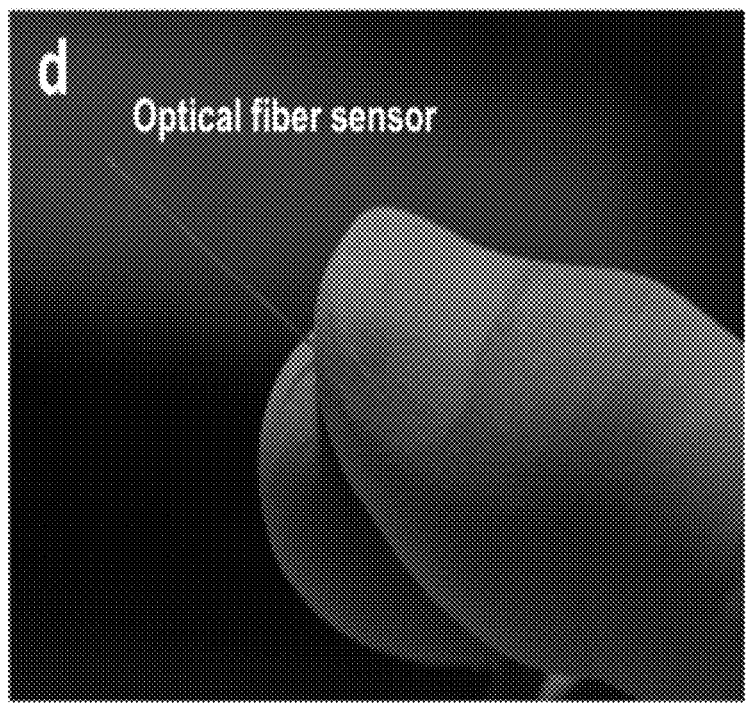

In order to facilitate the use of the TFBG as a measurement tool, the schematic and actual device configuration chosen is shown in FIGS. 6C and 6D. The metal coated TFBG is cut and the fiber end coated with a thin layer of gold acting as a broadband mirror. Light from a broadband source is coupled into the fiber through a coupler or circulator such that the reflected signal from the end mirror can be extracted and measured. This allows the measurement of the TFBG transmission spectra in reflection so that the device can be inserted into any location where the $H_2$ concentration needs to be monitored. In this configuration, the input light goes through the TFBG twice, an effect that is taken into account in the simulations of the spectra.

2.2 Optimization of Palladium Thickness

In this section, the simulation tool is first used to find the parameters of the gold coated TFBG used in the experiments from the measured spectrum. Apart from the known parameters of the Corning SMF-28 fiber used, the length of the grating and internal tilt angle, the remaining unknowns, which are the effective period and index modulation amplitude of the grating, can be found from the Bragg wavelength of the grating and the peak-to-peak amplitude of any given resonance (Erdogan and Sipe, 2008). For one of the devices used in the experiments, the measured spectrum shown in FIG. 8A was modeled with a refractive index modulation amplitude of 0.0012 and a period along the fiber axis of 532.73 nm.

Figure 8A:
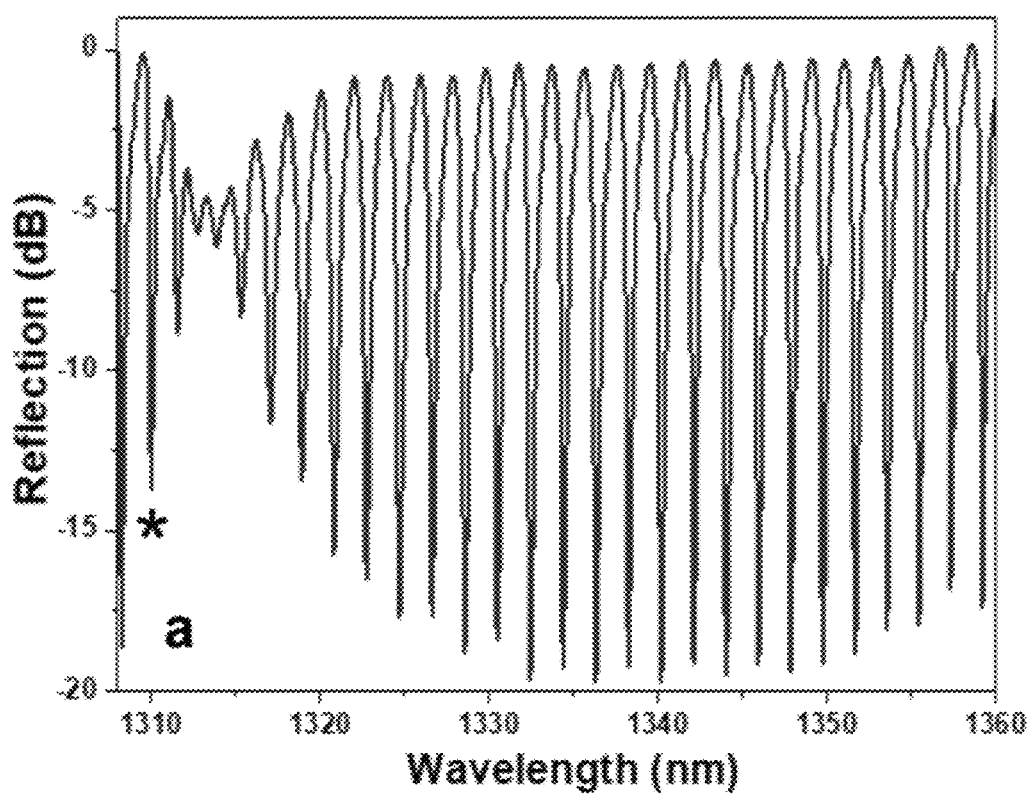
FIGS. 8A and 8B respectively show measured (FIG. 8A) and simulated (FIG. 8B) spectrum (zoomed SPR wavelength range) of an 18-mm long TFBG with a 30 nm thick gold coating and internal tilt angle of 23°. The refractive index modulation amplitude for which the simulated amplitude of the near 1310 nm resonance is equal to the measured one is 0.0012.
Figure 8B:
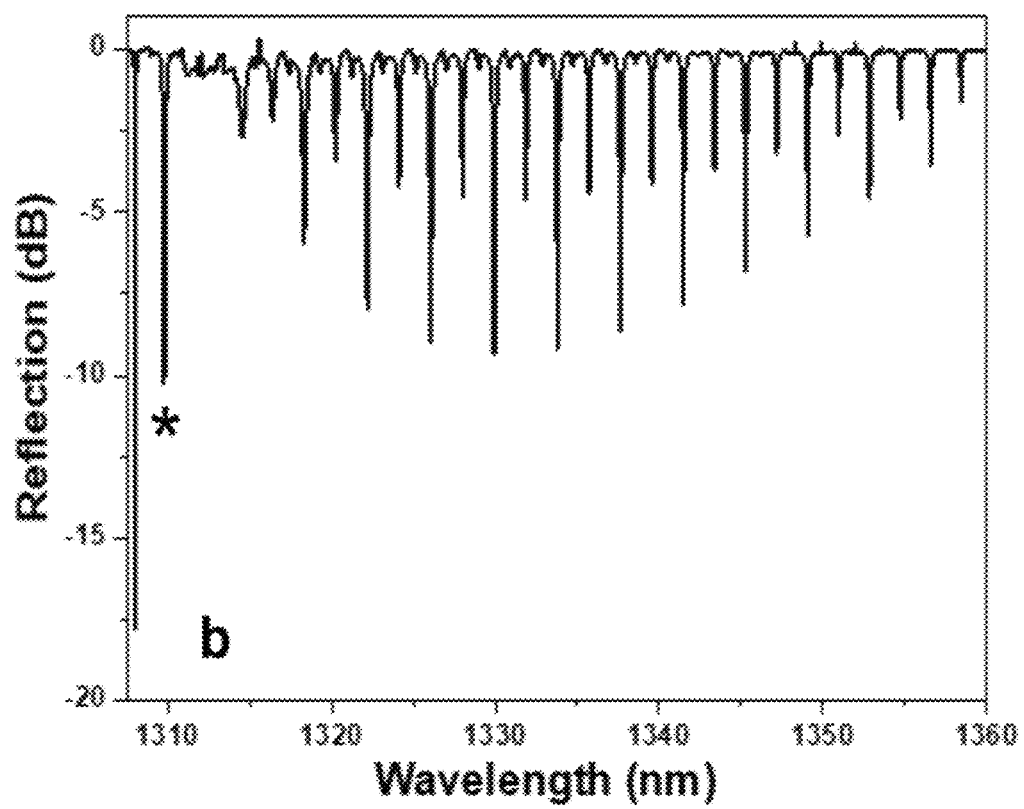
Figure 9B:
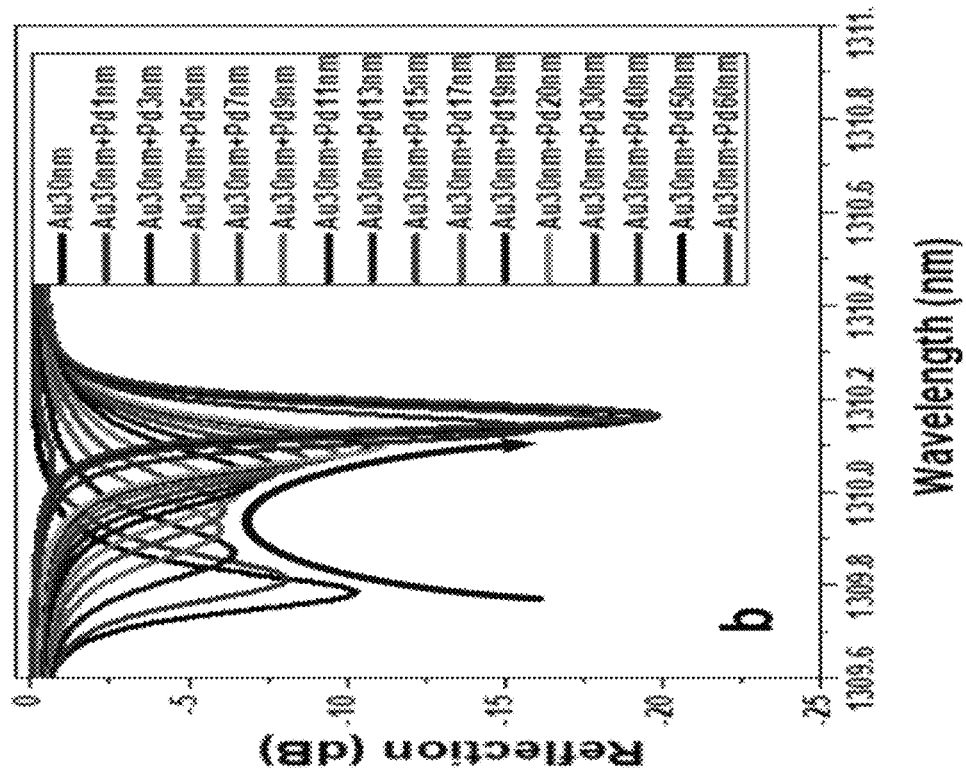
FIGS. 9A-9D respectively show experimental (FIG. 9A, FIG. 9C) and simulated (FIG. 9B, FIG. 9D) SPR spectral response when adds Pd to the gold coated TFBG (monitoring the 1310 nm mode resonance marked with "*" in FIG. 3)
Figure 9A:
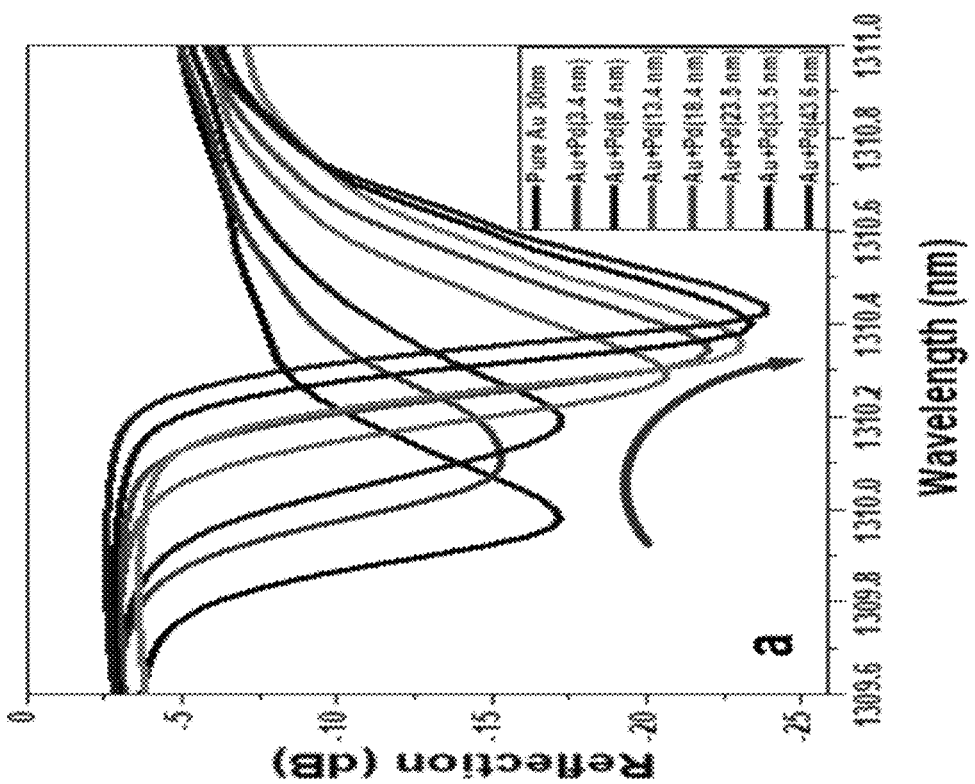
Figure 9D:
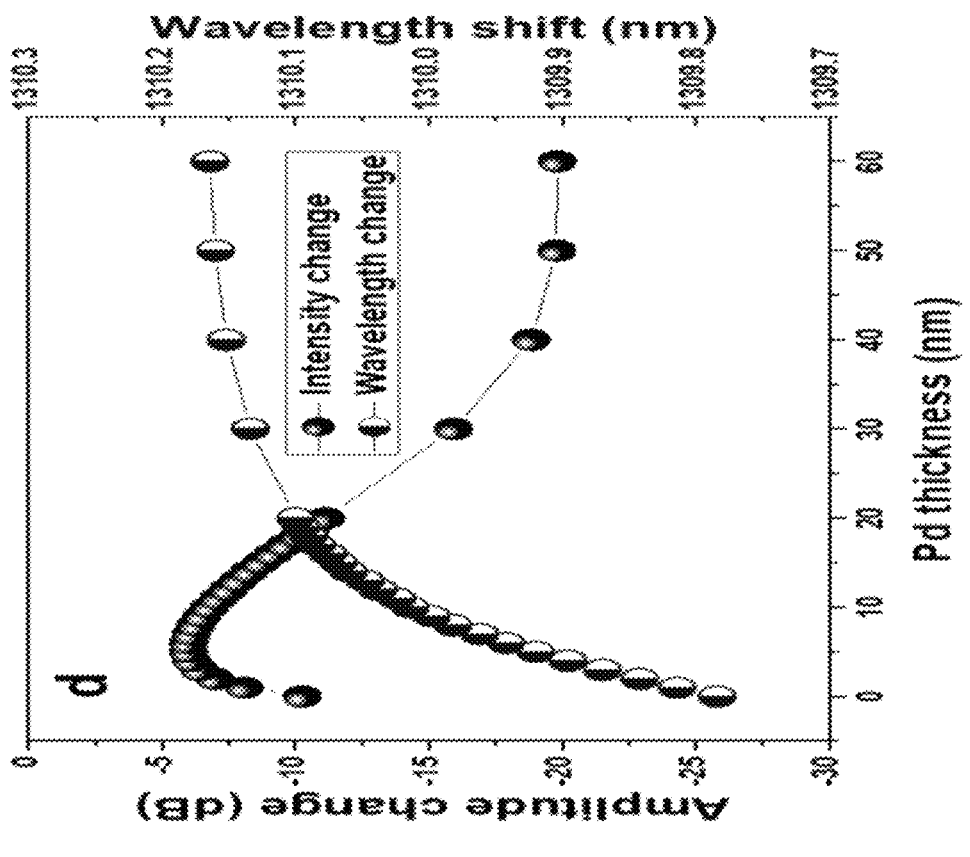
Figure 9C:
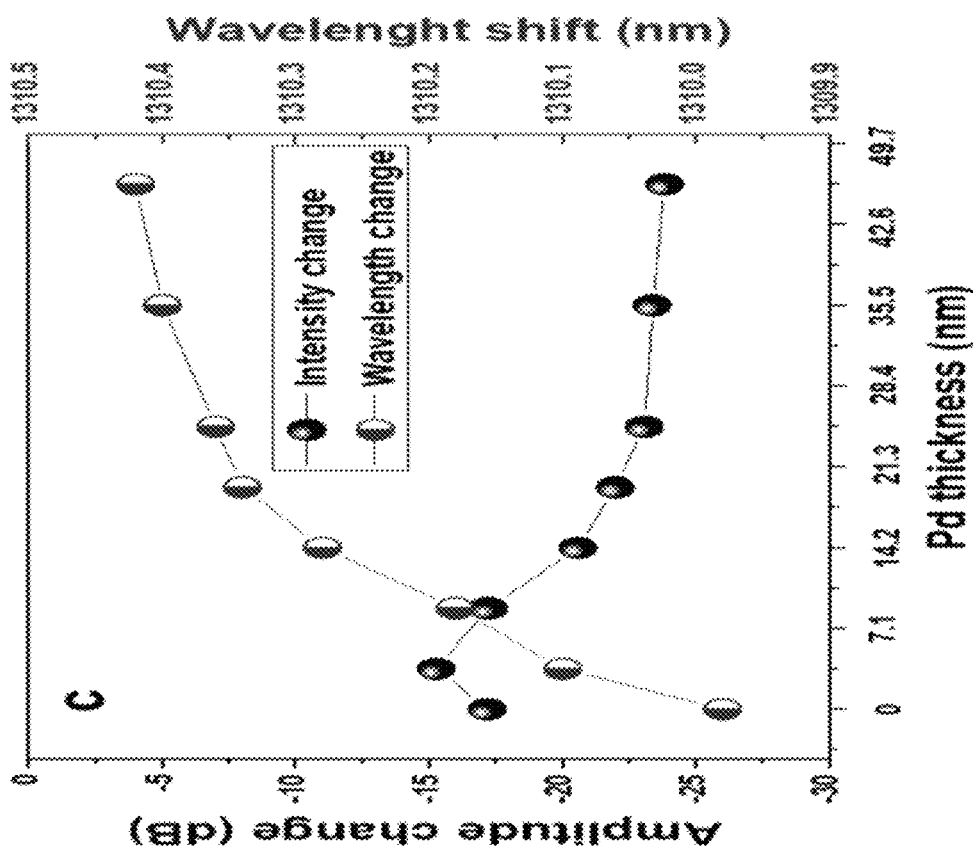

While the simulated spectrum shown in FIG. 8B does not fully match the experimental one, the main features are preserved and the grating parameters were adjusted so that the position, shape and peak-to-peak amplitude of the resonance located just on the blue side of the SPR maximum are identical to the measured one. This resonance provides a good compromise between plasmonic sensitivity enhancement and quality factor (narrow linewidth and large amplitude). With the model fiber thus obtained, simulations of the effect of increasing Pd thicknesses can be carried out and compared to the spectrum of the resonance measured after different durations of Pd deposition (FIGS. 9A-9D).

Figure 10:
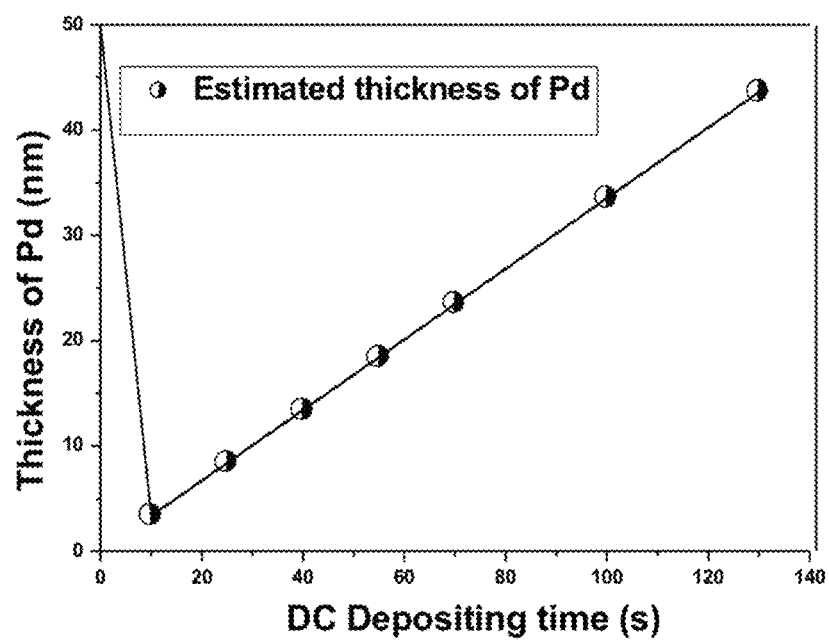
FIG. 10 shows estimation of the thickness of Pd with different depositing time according to the SEM when we deposited Pd for 20 s at the same condition.

The main outcomes of this analysis are that the identified resonance red-shifts rapidly with increasing Pd thickness and that its amplitude first decreases and then increases again, both in experiments and simulations. These changes appear to saturate for thicknesses exceeding 50 nm, indicating that the combined metal layers become thicker than the field penetration, as can be expected. Of particular interest is the fact that for thicknesses between 3 and 10 nm approximately, the amplitude of the simulated resonance becomes quite insensitive to thickness changes while the wavelength shifts rapidly. In spite of the lack of data for very small thicknesses, the experimental spectra show a similar effect with a maximum for a Pd deposition times of 10 seconds which corresponds to a thickness of 3.4 nm (from FIG. 10). This is interesting in the sense that the reaction of Pd with $H_2$ leads to volume changes in addition to chemical changes, so if we use a thickness in the aforementioned range the optical response that is measured by the TFBG will only be impacted by the chemical change (i.e. the change in permittivity) and not by thickness changes. Therefore further simulations are carried out to determine the effect of the Pd permittivity on the wavelength and amplitude of the 1310 nm resonance for several thicknesses between 0 and 20 nm and a 35% change in complex permittivity. One important assumption made in this simulation is that the real and imaginary parts of the complex permittivity change at the same rate, i.e. $\varepsilon(PdHx)=h(c)\cdot\varepsilon(Pd)$ where h(c) is a factor depending on the $H_2$ concentration, as indicated in ref (Bévenot et al., 2001). Early reports have demonstrated that the parameter h(c) is a nonlinear function decreasing with hydrogen concentration c and taking values less than 1. This function is an empirical one, the values of which can only be determined by comparison between simulation and experiment, which will be the case in the following.

Figure 11A:
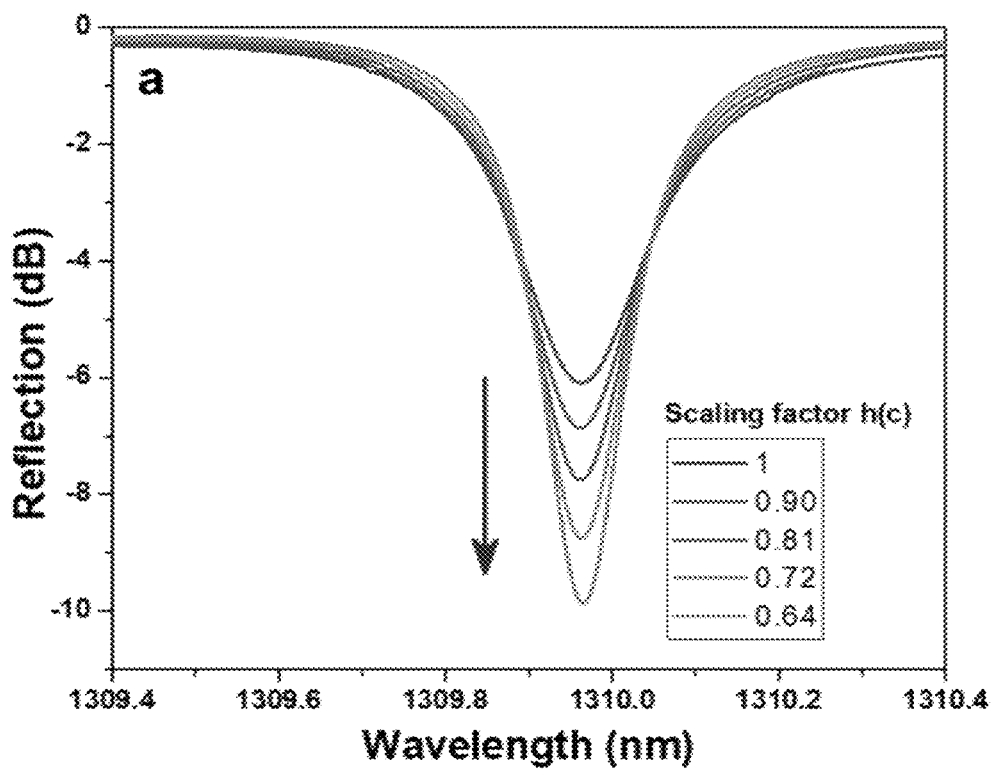
FIGS. 11A and 11B respectively show.
Figure 11B:
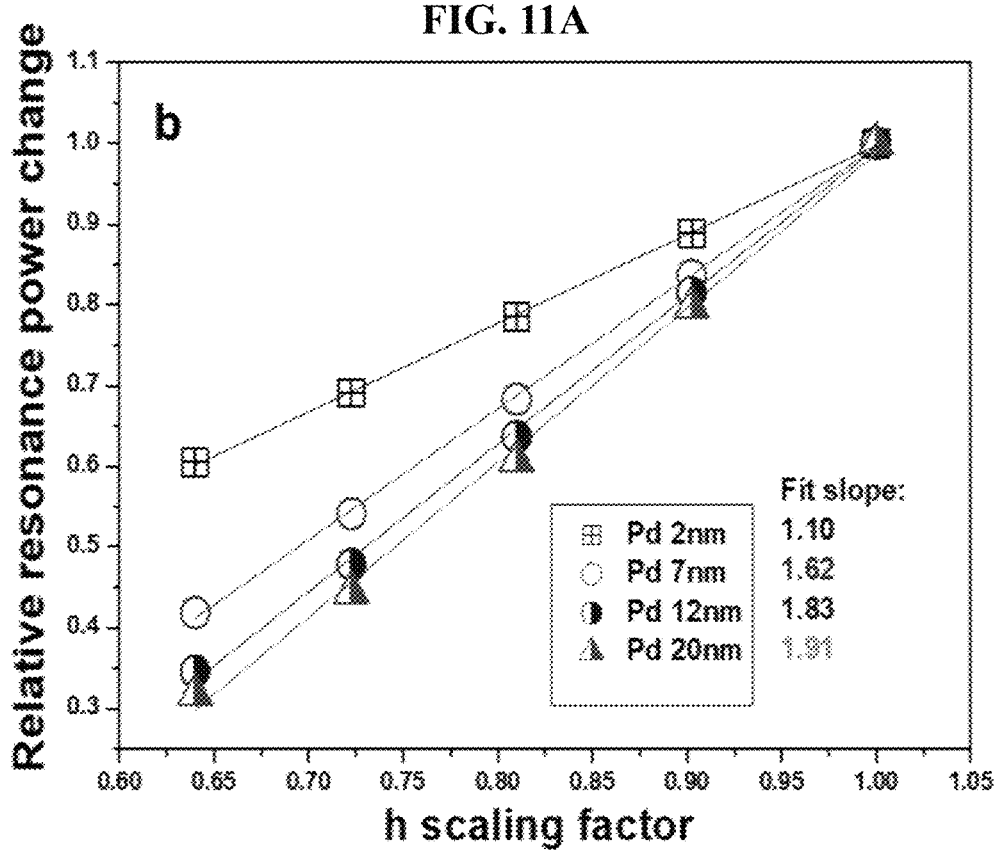

The results of this analysis show on FIGS. 11A and 11B that for a given thickness the resonance wavelength does not change but the amplitude increases with decreasing refractive index. Converting the dB scale of the reflection measurement in linear units, the sensitivity, i.e. rate of change of the reflected minimum power relative to its value for pure Pd (h=1), i.e. RP=P(h)/P(1), increases with thickness from 1.1 per fractional change in permittivity ($\Delta$h) at 2 nm, to 1.62 $\Delta h^{-1}$ at 7 nm and more slowly to 1.83 $\Delta h^{-1}$ and 1.91 $\Delta h^{-1}$ at 12 and 20 nm respectively. While it is customary to seek for the highest sensitivity in such experiments, here other factors come into play, namely the response time (faster for thinner Pd films) and the desired reversibility of the Pd-$H_2$ reaction. Because of this, a thickness of 7 nm was chosen for experiments designed to determine the permittivity of PdHx with sufficient precision to allow further use of such devices for $H_2$ sensing in practical applications.

2.3 Hydrogen Reactions with Pd-Coated, Au-Coated TFBG

Figure 12:
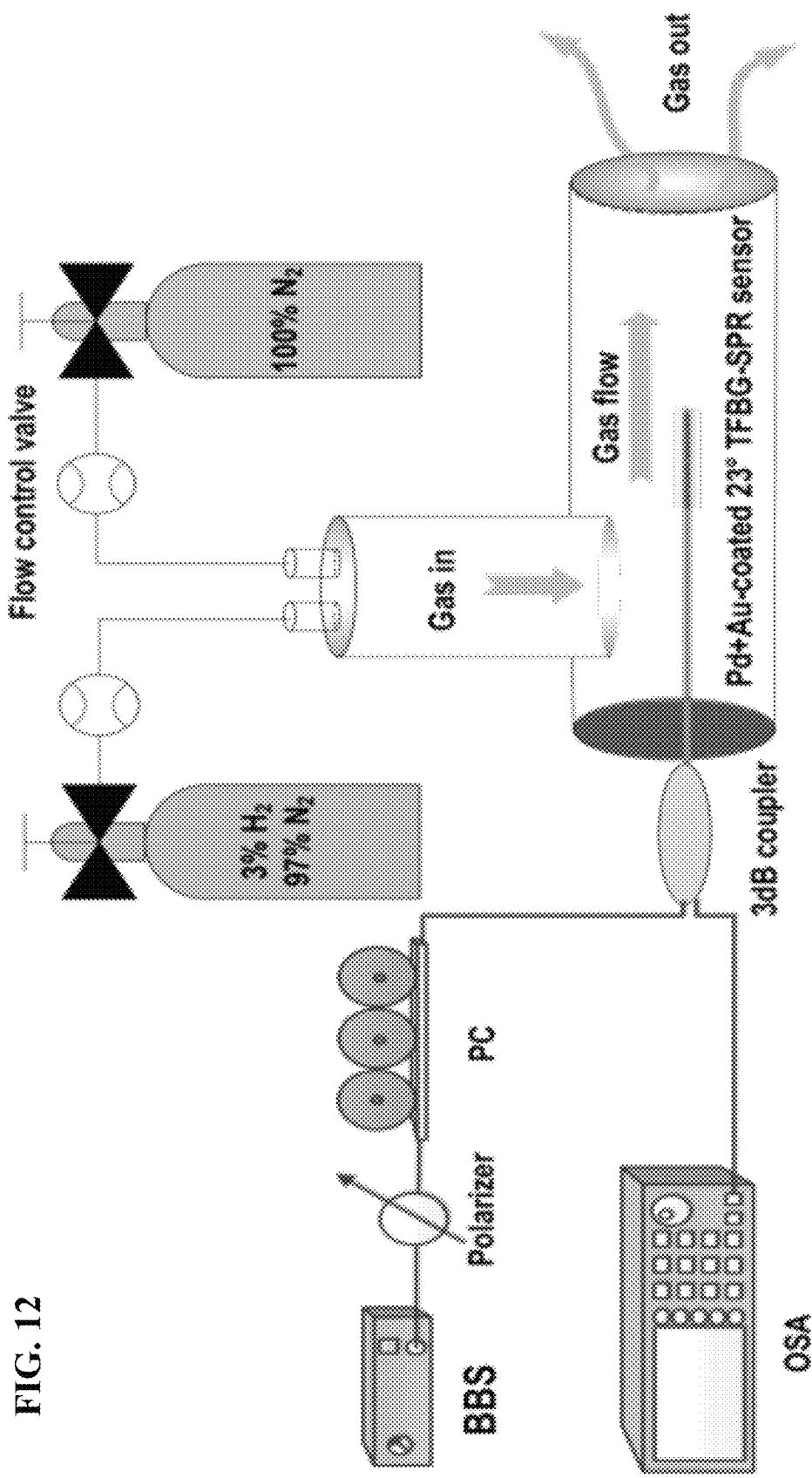
FIG. 12 shows the experimental setup to measure the coated TFBG response to various concentrations of $H_2$.
Figure 13A:
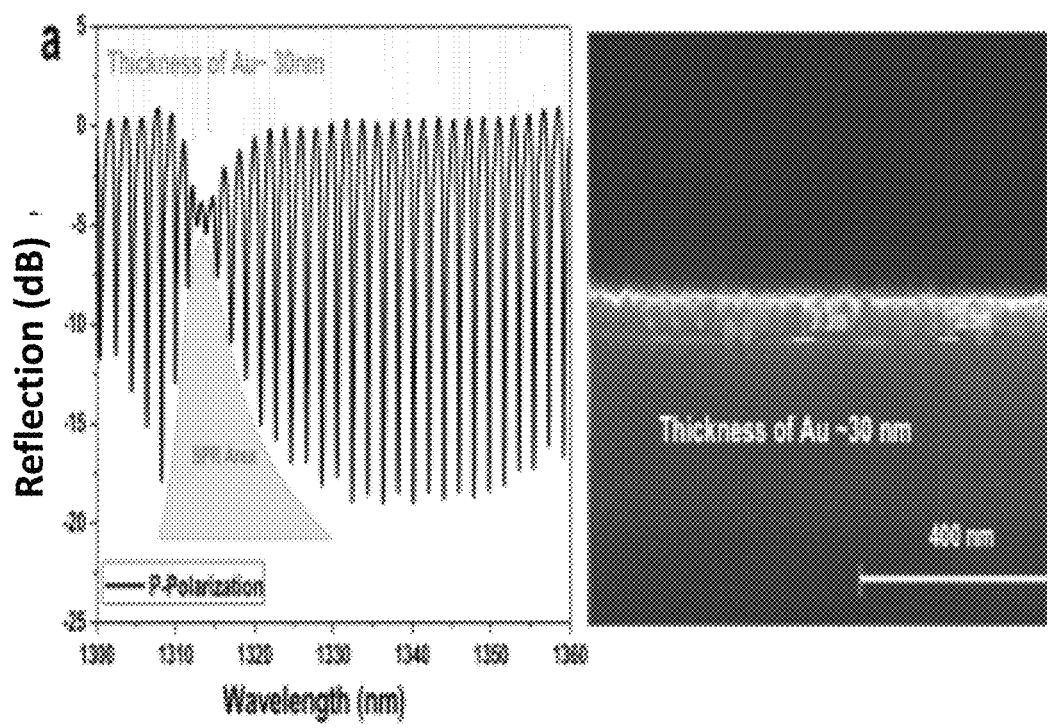
FIGS. 13A-13C respectively show.
Figure 13B:
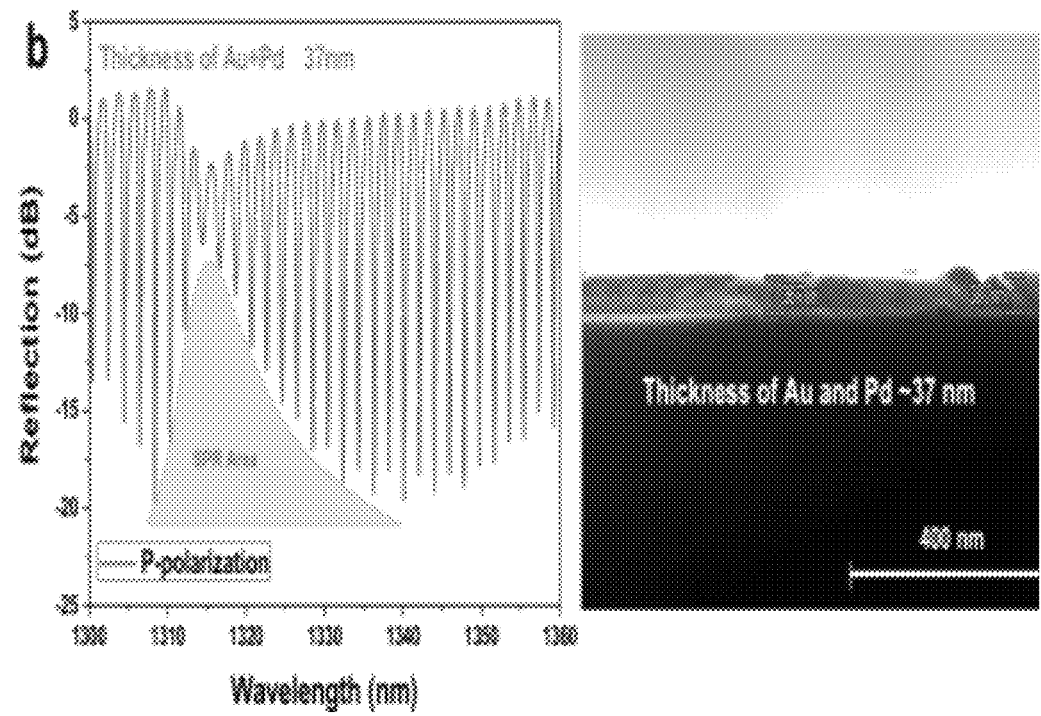
Figure 13C:
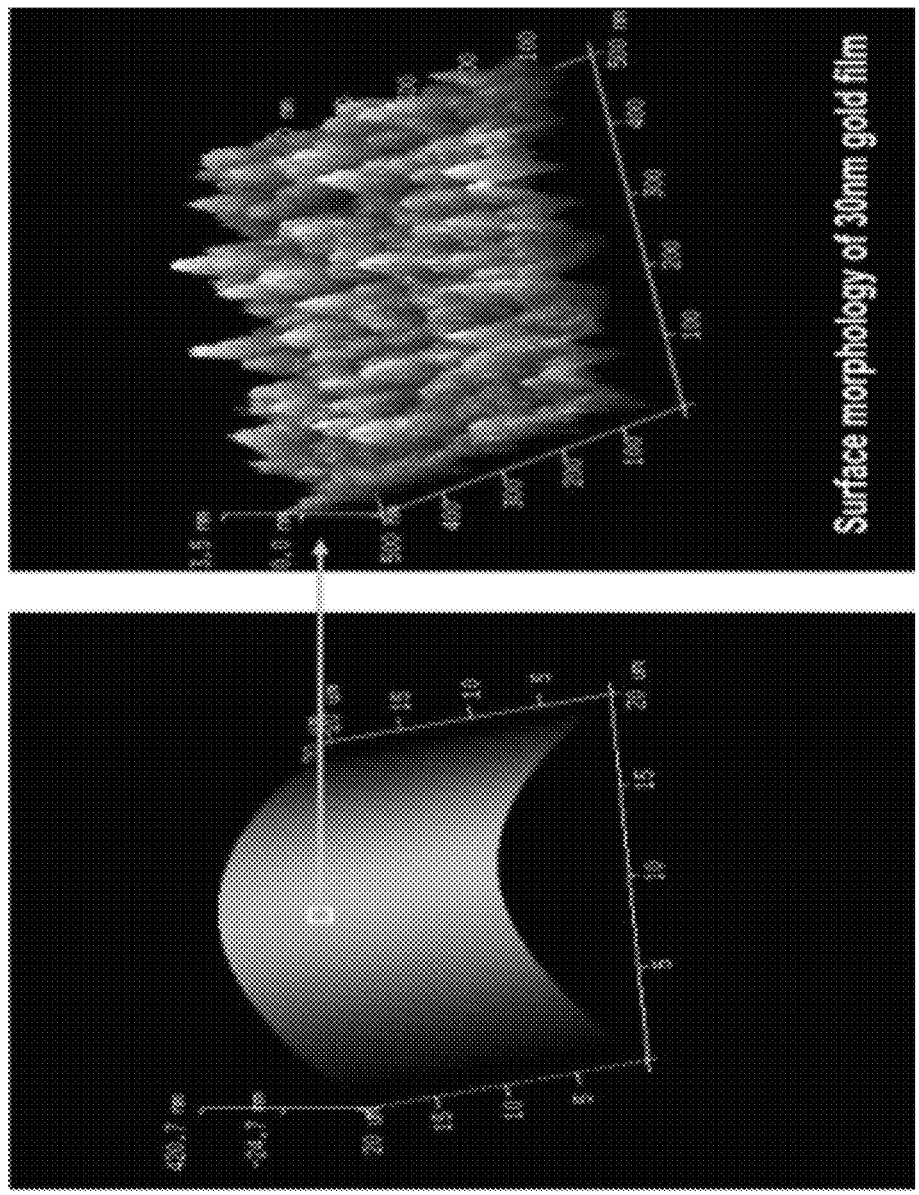

FIG. 12 shows the experimental setup for the measurement of the complex refractive index of thin Pd films exposed to various concentrations of $H_2$ based on an Au—Pd coated 23° TFBG with a ~200 nm thick gold mirror deposited on the cleaved end by direct current (DC) magnetron sputtering followed by a protective layer of 500 nm of $SiO_2$ using radio-frequency (RF) sputtering. The Pd coatings used were also deposited by magnetron sputtering. Light was launched in the core of the plasmonic TFBG from a broadband source (BBS) with wavelength range of 1280-1560 nm and the reflection spectrum was monitored by an optical spectrum analyzer (OSA) with a wavelength resolution of 0.02 nm. A linear polarizer and a polarization controller (PC) were placed upstream of the coupler to adjust and orient the state of polarization of light so as to provide the strongest SPR excitation. At this measurement resolution, spectra could be recorded continuously every 10 seconds. The gas chamber was made of a section of plastic tube which had an inlet and an outlet to allow the $H_2$-$N_2$ mixture flow in and out. The flow rates of hydrogen and nitrogen gases were individually controlled: the flow rate of nitrogen was kept at 500 cubic centimeters per minute (ccm) and while the flow rate from the 3% hydrogen in nitrogen cylinder was adjusted according to the required concentration. The inset of FIG. 12 shows the configuration of the Au—Pd coated TFBG probe. The azimuthal uniformity of the film thicknesses over the fiber surface was achieved by rotating fiber around its axis during all depositions except for the end-face mirror. The deposited gold film thickness was measured to be 32 nm and a further deposition of Pd for 20 seconds yielded an additional thickness of ~7 nm (from interpolation of the results in FIG. 10). Cross-sections of TFBGs with gold only and with gold-palladium combined films are shown in FIGS. 13A and 13B along with the corresponding spectra. Perfect thickness uniformity around the fiber circumference is not absolutely necessary to observe SPR effects (much of our earlier papers on this topic, available in the reference list, were obtained with double sided depositions that were much less uniform than those used here). The current method does provide very uniform coatings as shown in reference (Guo et al., 2017). FIG. 13C shows that the gold film has a RMS roughness of 0.7 nm. This roughness impacts the SPR response and this is the cause of the difference between the envelopes of the measured and simulated spectra (FIGS. 8A-8B and 9A-9D) since the simulated spectra assume "perfect" films with no additional loss from scattering. (Scattering adds a broadband additional loss in spectra, with some widening of the resonances). This being said, when fitting a single resonance (FIGS. 9A and 9B) the fact that we adjust the grating strength in the simulation to fit the measured resonance amplitude takes any scattering effect on the resonance into account implicitly. Further changes in scattering arising from adding up to 7 nm of Pd are negligible as can be seen on FIGS. 13A-13C by looking at resonances away from the SPR, and so are those following $H_2$ incorporation into the Pd. Therefore, and this is a key point of this whole work, we believe that our model reflects the experimental situation accurately, for a single resonance located on the shoulder of the SPR envelope.

3. Results and Discussions

Figure 14A:
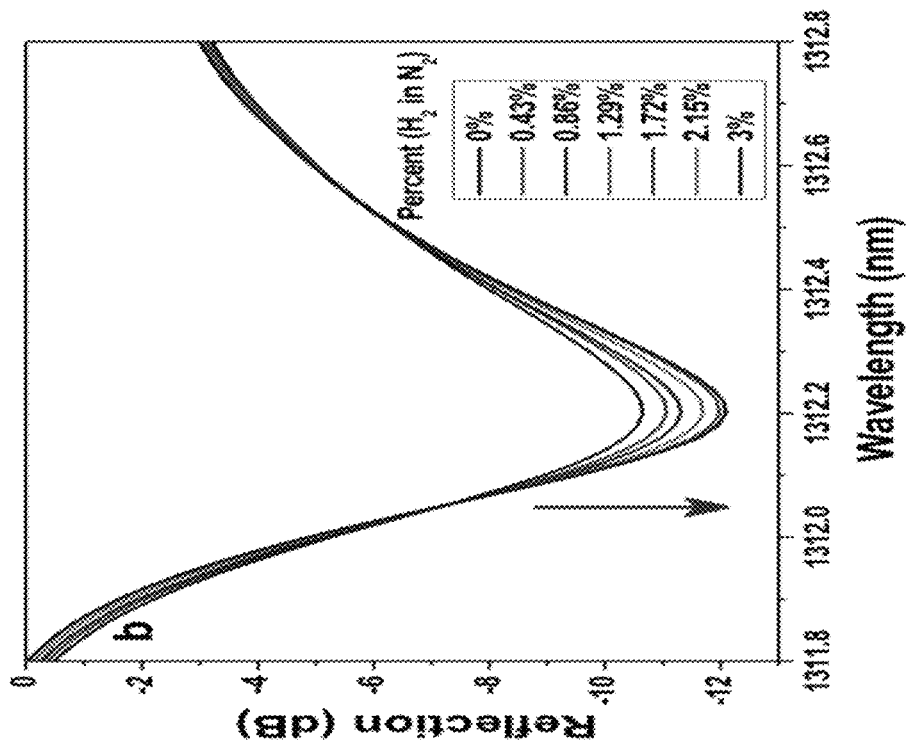
FIGS. 14A-14D respectively show.
Figure 14B:
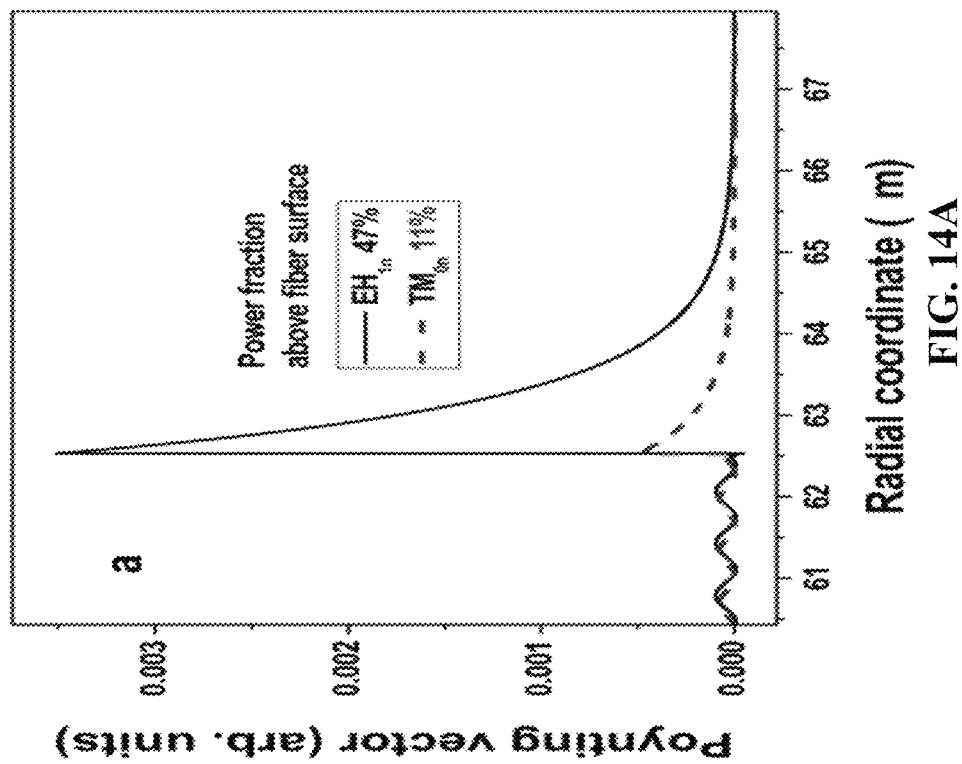

FIG. 14A shows the simulated distribution of the Poynting vector magnitude of the radially polarized electric field of the 1312 nm mode resonance near the cladding surface boundary: a strong enhancement of the mode power just above the metal layer is clearly seen due to coupling to the surface plasmon. Perturbations of any of the layers permittivity, such as those arising from the chemical reaction between $H_2$ and Pd, will be felt by the mode field and result in changes of its propagating characteristics and hence of the TFBG transmission spectrum. Such changes are clearly seen in FIG. 14B where the measured amplitude of the 1312 nm resonance is seen to increase when the ambient medium change from pure $N_2$ to 3% $H_2$ in $N_2$. It is interesting to note that the wavelength does not appear to change and this is confirmed by the more detailed experiment shown in FIGS. 14C and 14D. This means that either the thickness does not change (unlikely) or that as shown by the simulations in Section 2 the response of the TFBG is indeed insensitive to small thickness changes when its initial thickness is near 7 nm.

Figure 14D:
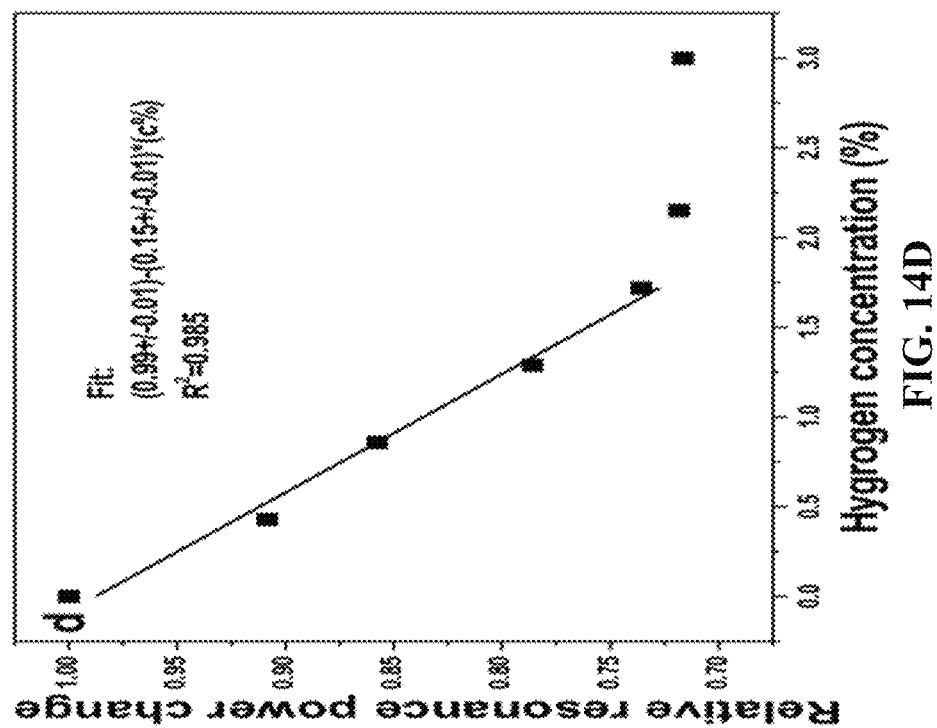
Figure 14C:
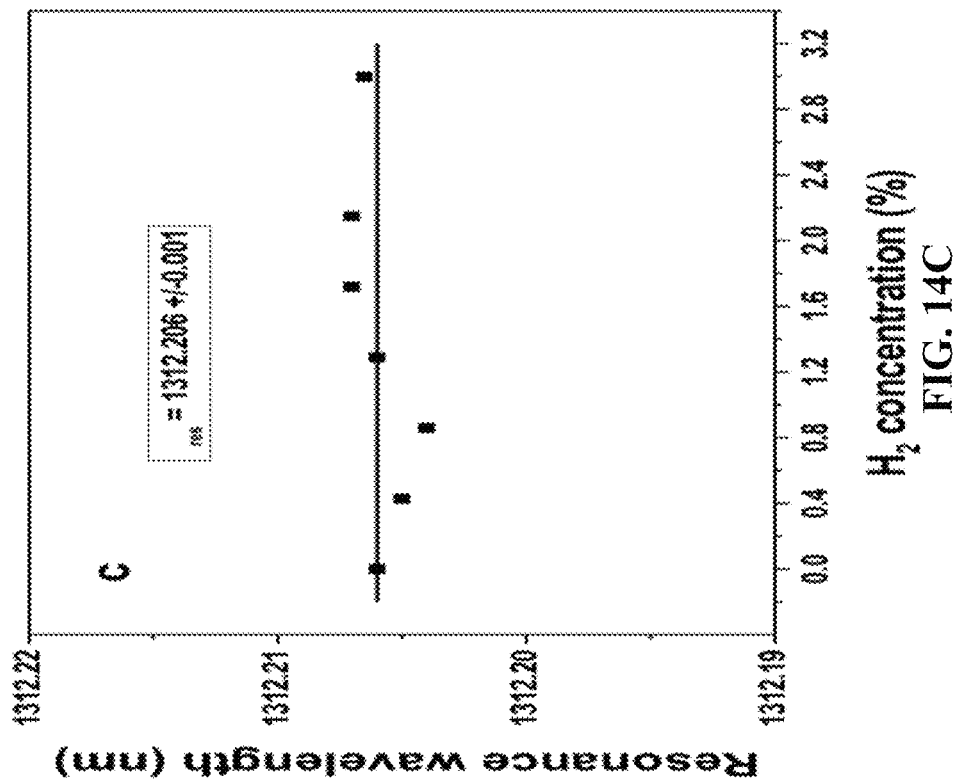

The relative power change of the 1312 nm resonance is linear over the concentration range from 0 to 1.7% with a slope of $\Delta RP/\Delta c$ %=$-0.15$ while the wavelength remains constant at 1312.206 nm+/$-0.001$ nm (FIGS. 14C and 14D). Comparing these to the simulations carried out for the TFBG with a 30 nm gold coating and 7 nm thick Pd film ($\Delta RP/\Delta h$=1.62) allows the determination of the complex permittivity of the PdHx ($\varepsilon_c$(PdHx)=h(c %)·$\varepsilon_c$(Pd) where h(c %)=1+($\Delta h/\Delta c$ %)·c) as follows:

$$\Delta h/\Delta c = (\Delta RP/\Delta c\ \%)/(\Delta RP/\Delta h) = -0.093 \text{ (for } c\ \%(H_2) \text{ between 0 and 1.7\%)} \quad (1)$$

Higher concentrations of $H_2$ do not cause further increases in the resonance amplitude for this particular configuration and hence cannot be measured, but the current approach does yield important information at concentrations covering about half the range over which the $H_2$ mixture is not igniting easily. At room temperature, 1-2% concentration range also corresponds to the beginning of the transition of the PdHx compound from the so-called alpha to the beta phase, where the alpha phase corresponds to a state where the $H_2$ is just dissolved into the Pd matrix and not chemically bonded to it whereas the beta phase corresponds to chemically stable palladium hydride.

In practice, once a device is fabricated (TFBG+gold+Pd), it is measured in air (known to be free of $H_2$) to obtain a starting spectrum (as in FIGS. 8A and 8B). Then inverse modelling is used to fit the only adjustable parameter that may vary from device to device, i.e. the initial amplitude of the SPR resonance of that particular device. After the fit, the model reproduces the initial state of the SPR resonance (FIGS. 9A-9D). Finally the response of this particular device to $H_2$ exposure can be predicted using the found relationship (Equation. (1)) between $H_2$ concentration and complex permittivity of Pd. Therefore, each device does not need to be exposed to different concentrations of $H_2$ prior to use to establish its calibration, which would be prohibitively expensive.

Another design criterion which resulted in giving up some sensitivity by going with a thinner Pd layer was the re-usability of the sensor and its temporal response. FIG. 15A shows a cycling experiment where the $H_2$ concentration was suddenly changed from 0 to 3%. The initial response is 100 s while the recovery takes approximately 400 s. The response and recovery times are ~50 s, for a Pd thickness of 5 nm on a gold waveguiding membrane of 20 nm thickness. That configuration had a sensitivity magnitude, measured for small $H_2$ concentrations, to be of the order of 0.3 dB/c %($H_2$), i.e. similar to the one measured here (−0.79 dB/c %($H_2$) after converting units). Finally, a closer examination of the initial plateau in FIG. 15A (shown as FIG. 15B) shows that the standard deviation (measurement noise) of the resonance amplitude for a constant (0%) $H_2$ concentration is +/−0.01 dB. Therefore, the limit of detection can be estimated in the usual manner by a measurement value equal to three times the standard deviation, which corresponds to a concentration of 0.038% or 380 ppm. In terms of signal to noise ratio, the power oscillations in FIG. 15A are more than 100 times larger than the noise seen in FIG. 15B. Finally, it is clear that the performance of this device drifts with successive cycling, which is a common feature for Pd coated sensing devices and is due to irreversible changes in the structure of the coatings. Therefore in its current state, the devices described here will perform best as part of alarm systems to detect when the concentration of $H_2$ exceeds predetermined levels and then replaced.

4. Conclusion

The complex permittivity of a nanoscale layer of Pd exposed to $H_2$ volume fractions between 0 and 1.7% in $N_2$ was determined at wavelengths near 1310 nm using a plasmon-assisted measurement by a tilted fiber Bragg grating (the sensor still responds for concentrations up to 3% hydrogen, but nonlinearly and gradually saturates beyond 1.7%). The complex permittivity decreases linearly by a factor equal to 0.093 per %-change in $H_2$ concentration in the range from 0 to 1.7%. Simulations and measurements indicate that the optical properties of the fiber grating coated with 30 nm of gold and 7 nm of palladium can be modelled with a combination of a finite difference complex mode solver and standard coupled mode theory. These simulations also indicate that the grating response is insensitive to thickness changes when the thickness of the Pd film lies in the 3-10 nm range. Therefore, knowledge of the complex permittivity of Pd as a function of $H_2$ concentration can be used to develop other sensors based on coated optical fibers and also to avoid having to calibrate individual sensors prior to use: a simple measurement in air enables the extraction of all the relevant parameters which can then be use to extract $H_2$ concentrations from changes in the sensor response. This "model-based" calibration of each sensor from a simple initial measurement in air is the key point that will enable the mass production of low cost, disposable sensor devices fabricated using mass production techniques already developed for FBGs in telecommunications and physical sensing (for strain and temperature). The response time of the device was measured to be of the order of 100 s and the recovery was 400 s, over several cycles between 0 and 3% $H_2$. While there is a small drift in response over successive cycles of exposure to $H_2$, the low cost of the sensor transducer enables its use as single use disposable device in alarm systems for $H_2$ leaks approaching the flammability concentrations. Finally, the limit of detection for $H_2$ concentrations below 1.7% was determined from the measured noise and detection sensitivity to be 0.04% at a level equal to 3 times the noise.

Embodiment 2

Embodiment 2 provides an optical fiber-based hydrogen-sensing apparatus with its coating assembly consisting of only one single Pd film layer. Due to the phase transition of palladium in the presence of hydrogen, intensity changes in the optical transmission of the devices are produced when interacting with this gas. It is demonstrated that these platforms can be used for hydrogen detection, being able to respond to concentrations way below the lower explosive limit.

1 Introduction

The basis of a TFBG is a periodic and permanent refractive index modulation of the optical fiber core that is angled with respect to the perpendicular to the fiber longitudinal axis. It causes a portion of the light that propagates through the fiber core to get coupled to the cladding. These beams form a comb of cladding mode resonances that are sensitive to refractive index changes in the medium surrounding the sensor. When the optical fiber is coated with a thin metal film at the grating location, cladding modes reaching the metal with a proper polarization and a certain incidence angle can excite a surface plasmon wave on the interface between the metal and a dielectric surrounding medium. Gold-coated TFBG sensors have achieved refractive index sensitivities of $10^{-5}$-$10^{-6}$ in biochemical applications (Caucheteur et al., 2015). TFBG-based SPR sensors have been typically developed using gold or silver coatings for convenience into biochemical sensing, where the surrounding media have refractive index values close to the one of water. However, the use of other metals widens the range of potential applications of these sensors. Many hydrogen sensors have been developed in the recent years. Some are electrical hydrogen gas sensors, usually based on palladium (Pd) nanowires and nanoparticles. However, such electrical sensors show enhanced sensitivity at high working temperatures, thus raising safety issues. Alternatively, optical sensors were based on different configurations of optics, such as a glass prism or a micro-mirror. Most of these fiber sensors were Pd-based instead of absorption spectroscopy because of the molecular structure of hydrogen, which does not allow the use of conventional absorption spectroscopy as an analytical tool, since molecular hydrogen is transparent at optical frequencies. And in the presence of hydrogen, palladium undergoes a reversible phase transition from metal to metal hydride, a phase in which hydrogen is inserted within the palladium crystal lattice, providing a mean to modify the optical properties of the sensors. The propagation constant of surface plasmons in palladium at the metal-liquid or metal-air interfaces is more strongly mismatched to that of gold-coated or silver-coated sensors, which makes the coupling of light to the SPR difficult. Some of the optical fiber SPR sensors were coated with hybrid metals, such as gold/palladium thin films or gold/palladium core/shell nanorod metamaterials, to ease the coupling of light to the SPR. The coupling problem of the single layer of palladium has been demonstrated for bulk SPR sensors using a palladium-coated glass prism based on the Kretschmann prism configuration and a very low incidence angle and in the case of optical fibers for unclad fibers where the use of strongly off-axis input light launched in the fiber allowed SPR excitation.

2 Methods, Simulations and Optimization

The optical structure proposed in this work is the one shown in FIG. 16, which consists of a single layer palladium-coated TFBG, instead of using hybrid coatings or additional materials sensitive to the gas. As mentioned before, the modes reflected by the grating planes and propagating through the optical fiber cladding excite an SPR at the interface between the palladium film and the surrounding medium. Unlike other FBG-based sensors exploiting the swelling of palladium, the optical response of this sensor will be influenced directly by the change of the metal coating from palladium to palladium hydride in the presence of hydrogen gas. This way, these structures could be applied in the industry for hydrogen detection at difficult access locations. In order to find a proper thickness of the palladium film to be deposited around the TFBG, simulations of the transmission spectrum for different thickness values were carried out. First, the modes of the fiber structure (including core, cladding, metal layers and surrounding medium) were solved with a complex vectorial finite-difference algorithm to apply afterwards the coupled mode theory to adapt the results to the particular case of TFBGs studied in transmission (Erdogan and Sipe, 1996). The simulation parameters were a core radius of 4.1 μm with a refractive index of 1.4545 RIU (refractive index unit), a cladding radius of 62.5 μm with a refractive index of 1.4467 RIU, a refractive index of palladium of 2.8716-7.9706i (Johnson and Christy, 1974) and several thickness values for the metal coating in the range from 20 nm to 100 nm. Al-though other values were simulated, FIG. 17A shows selected results obtained for a palladium thickness of 30, 60 and 90 nm, respectively. As it can be seen, for a metal coating of 90 nm, the coupling to the plasmon wave occurs, but the amplitude of the cladding modes at both sides is not enough to make the sensor practically interrogated. For the 30 nm coating, the shape of the spectrum is almost flat, since the coating is not thick enough and the cladding modes get radiated to the external medium. Finally, the optimization of the results led to a palladium coating of 60 nm and to an SPR location around 1470 nm. This is where the intensity of the cladding modes reaches an absolute minimum, corresponding to the maximum optical power coupled to the plasmon. For this thickness, there is a good ratio between the attenuation due to the coupling to the plasmon and the amplitude of the cladding modes around the SPR.

These results were experimentally verified by fabricating a structure like the simulated one. TFBGs with a tilt angle of 10° were photo-inscribed in the core of a hydrogen-loaded telecommunications-grade single-mode optical fiber (Corning SMF-28) with a Noria FBG manufacturing system using 193 nm excimer UV radiation and the phase-mask technique. TFBGs produced by this method exhibit a wide resonance comb whose cladding modes propagate even reaching refractive index values close to the one of the air, so they are convenient for gas sensing purposes. After the photo-inscription process, a film of 60 nm of palladium was deposited around the TFBG using a magnetron sputtering process. The transmission optical spectrum of the fabricated structure was measured using the same wavelength window of the simulations, resulting in the trace shown in FIG. 17B. As it can be seen, the SPR region is located at the expected wavelength range and the envelope of the spectrum clearly shows where the coupling to the SPR occurs.

Figure 18:
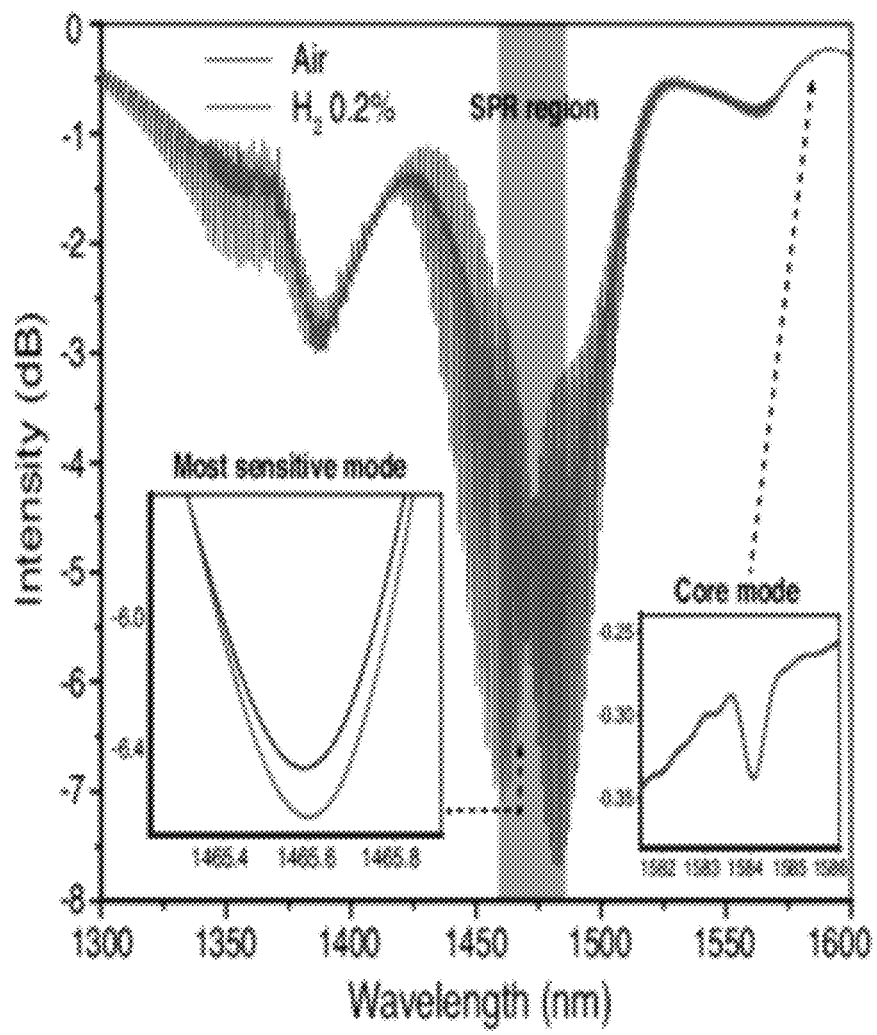
FIG. 18 shows optical transmission spectrum of the palladium-coated TFBG with the SPR region shadowed in yellow. The two inlay highlight the most RI-sensitive mode and the core mode, used as a temperature reference.

The full transmission spectrum of the structure is shown in FIG. 18, where it is possible to compare its response in the air to the one at a hydrogen atmosphere with a concentration of 0.2% in volume. First, it is possible to see again that the SPR region, highlighted in yellow, is clearly identifiable in the spectrum. Secondly, the inlay of the most sensitive mode illustrates the intensity change of the sensor in the presence of hydrogen due to the change of the metal into palladium hydride. TFBG-based SPR sensors can be interrogated both in wavelength and intensity, so the second method will be used in this case since the intensity change is the predominant alteration in the spectrum. Finally, the core mode is located at 1584.1 nm, and can be used as a temperature reference when carrying out a spectrometer-based interrogation.

Figure 19:
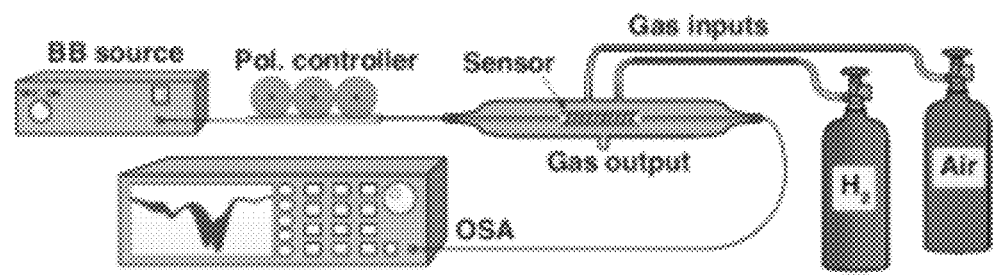
FIG. 19 illustrates the setup used to evaluate the response of the palladium coated TFBG in the presence of hydrogen gas.

The performance of the platform and its suitability for hydrogen detection were evaluated by introducing the sensor into a gas chamber and using the setup illustrated in FIG. 19. A broadband light source was connected to a polarization controller in order to select a radial (P) polarization and maximize the coupling of light to the plasmon, and finally the interrogation was carried out with an optical spectrum analyser. The gas chamber incorporated two gas inputs which were connected to gas cylinders of hydrogen and synthetic air respectively, this last one passing through a gas bubbler when humidity in the chamber was required. By controlling the flow of each of the gases, different hydrogen concentrations could be reached and most importantly, rapid changes from air to hydrogen atmospheres were performed.

3. Results and Discussions

Figure 20:
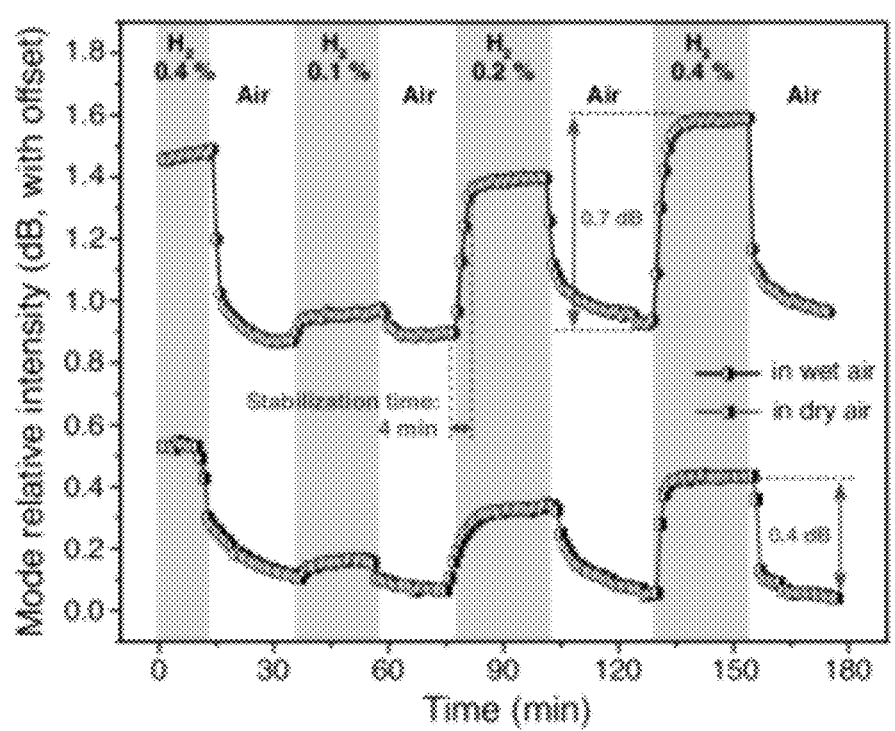
FIG. 20 illustrates the response of the sensor to the presence of hydrogen in wet (top) and dry air (bottom)

The result of the tests can be seen in FIG. 20, whose first highlight is an excellent reversibility of the sensor response with respect to the changes in the surrounding atmosphere. The changes were performed from air environments to others with some hydrogen content to simulate different kinds of leaks. As it can be seen, the sensor reacts to hydrogen concentrations of 0.1%, 0.2% and 0.4% in volume, all of them way below the lower explosive limit of the gas, which corresponds to a concentration of 4%. And when the hydrogen is flushed out of the gas chamber by introducing an air flow, the intensity of the mode goes back to previous values. As shown in the figure, the relative changes are higher when the sensor works in a wet atmosphere, reaching 0.7 dB when going from wet air to 0.4% of hydrogen, since humidity increases the absolute hydrogen concentration in the chamber. The stabilization time of the sensor was measured as well, resulting 4 min, although a rapid response can be observed almost in real time. In addition, the standard deviation of the mode intensity for a constant hydrogen concentration of 0.4% is ±0.0025 dB. That means that the theoretical limit of detection of this sensor can be estimated to be equivalent to a hydrogen concentration value of 0.004%, or 40 ppm.

4. Conclusion

The work describes the procedure to achieve SPR excitation with optical fiber gratings using a single-layer palladium coating. The propagation constant of surface plasmons in this metal mismatches the one of gold or silver, traditionally used for biochemical applications, so some simulations are carried out to obtain a proper thickness of palladium. The results show that with a film of 60 nm of palladium there is a maximum of light coupling from the cladding modes to the plasmon. A sensor based on a TFBG coated with a layer of these characteristics is fabricated and its transmission optical spectrum results to be in good agreement with the previous simulations. After that, the performance of the sensor was evaluated when exposing it to different hydrogen concentrations in an air atmosphere. The experimental results show that the sensor reacts to hydrogen leaks with concentrations of 0.1%, 0.2% or 0.4% in volume, all of them below the lower explosive limit of the gas, corresponding to 4%. Among the characteristics of the sensor it is worth mentioning a good reversibility, fast response and stabilization times and a low limit of detection. Together with the intrinsic features of optical fibers, these sensors provide a suitable solution for hydrogen detection into difficult access. Some examples include applications for certain industrial environments or installation of the sensors next to the fuel deposits of hydrogen-powered vehicles. Their aim will be focused on security and human or equipment preservation.

Embodiment 3

Embodiment 3 provides a hybrid organic-inorganic material film coated plasmonic highly tilted fiber Bragg grating (TFBG) sensor for ammonia detection. The sensor is made by coating a 50-nm-thick gold film over the 37.5 degree tilted fiber Bragg grating. And then, a hybrid organic-inorganic(polyaniline-$SnO_2$) material, a polyaniline nanocomposites decorated $SnO_2$ thin film, was coated over the gold film surface. A spectrally-dense comb of the backward-propagating cladding resonance mode is excited due to the fiber grating. A possible synergy of the $NH_3$ sensitive function material (polyaniline-$SnO_2$) and the plasmonic TFBG structure makes this device a unique tool for low concentration of ammonia measurement via monitoring the strength change of plasmon resonance intensity. The experimental results present that our gas sensor can detect ammonia at concentration in air as low as 5 ppm in room temperature, reversible property and excellent selectivity with $NH_3$. Furthermore, because of the property of the fiber sensor, the small size, lack of bulky was achieved. The real-time remote monitored ammonia at different concentrations and capability for measurements in harsh places can be achieved.

Introduction

Gas sensors are regarded as one of the most important technologies for monitoring environmental quality and human health. To date, Organic and inorganic materials as two kind of significate materials widely use in gas sensing. $SnO_2$ is one of the most popular inorganic material studied and used on the field of gas sensing. But its operation temperature is about more than 250° C. Similarly, although most of inorganic materials, likes zinc oxide(ZnO), tungsten oxide($WO_3$), titanium oxide($TiO_2$), iron oxide($Fe_2O_3$/$Fe_3O_4$), etc., are sensitivity to variety of gas at low levels, because of the change of their oxygen stoichiometry and electrically active surface charge. Some properties of the sensor, such as sensor life, portability and power consumption, are influenced by the need of the high operation. On the other hand, the gas sensing devices based on organic materials, such as polyaniline, polypyrrole, and metal phthalocyanines, have gas sensitivity at room temperature. However, due to the moisture and orderly structure, they are sometimes unstable and exhibit long response time.

Ammonia has given rise to serious environmental problems due to its toxicity, and reliable detection of $NH_3$ gas leaked into the atmosphere is needed. Current microfiber-based Mach-Zehnder interferometer coated with Graphene for $NH_3$ detection can realize limit detection of 40 ppm and response time of ~0.5 second for the concentration of 360 ppm. However, such microfiber based sensors have poor reproductivity, moreover, it is hardly to tackle the temperature induced cross-sensitivity. Herein an improved device using highly TFBG-SPR sensor coated with a hybrid organic-inorganic material (polyaniline-$SnO_2$) for $NH_3$ gas detection is disclosed. Because of a possible synergy of organic-inorganic (polyaniline-$SnO_2$) material and TFBG-SPR sensor, our device achieved concentration as low as 5 ppm, and response time is 100 seconds. The liner fit can be targeted from 5 ppm to 40 ppm. And it had excellent reversibility and selectivity to $NH_3$.

Materials and Methods

Materials: A 30-nm-thick tin oxide film was radio-frequency magnetron sputtered on the surface of the fiber SPR sensor using the magnetron sputtering coating machine (model TRI-S500 fiber material metal coating system). The polyaniline was decorated on the surface of the $SnO_2$ thin film.

Figure 21A:
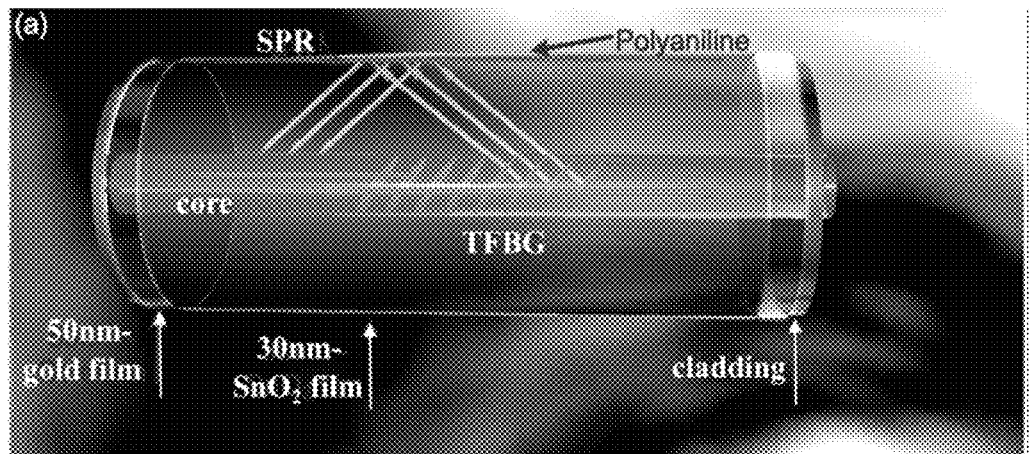
FIGS. 21A-21D respectively show.

Highly tilt fiber Bragg grating SPR sensor fabrication: FIG. 21A shows the configuration of the proposed $NH_3$ gas sensor and the detail information of the working principle of TFBG. A TFBG was inscribed in the core of hydrogen doped telecommunication-grade single mode fiber (Corning SM-28). TFBGs are fabricated using the same tools and phase-mask technique as standard FBGs, assembly rotation technique as described in (Guo et al., 2016). The excimer UV laser works at a wavelength of 193 nm and with a pulse power of 3 mJ at frequency of 200 Hz. The grating is with a pitch period of 536.075 nm and the tilt angle of 37.5° respected to the perpendicular to the optical fiber axis, so the maximum amplitude of cladding modes for measuring RI in the range 1.0 and below in gas environment can be achieved. The total grating length is 2 cm with a Bragg core mode of 1543 nm. With hydrogen-loading, the photosensitivity of the fiber core can be much improved. So we can easily fabricate a TFBG with reflectivity more than 95% over the fiber core.

A 50-nm-thick gold film was radio-frequency magnetron sputtered. The working principle of the gold coated TFBG can be seen in FIG. 21A, the arrows represent light resonantly coupled from the core mode to cladding modes propagating in the cladding, every wavelength of the resonance corresponding to an effective mode index. When the axial component of the propagation constant of the cladding mode equals that of an SPP, coupling to that SPP can occur and the transmission spectrum of the TFBG reveals a consequent reduction in the light intensity.

The following two equations can fully describe the working principle of TFBG sensor (Albert et al., 2013)(Guo, 2017).

$$\lambda_{clad,i} = \frac{(N_{core}^{eff} + N_{clad,i}^{eff})\Lambda}{\cos\theta} \quad (2)$$

$$\beta_{spp} = \frac{\omega}{c}\sqrt{\frac{\varepsilon_m \varepsilon_s}{\varepsilon_m + \varepsilon_s}} \quad (3)$$

The Equations (2) and (3) represent that the excitation of cladding modes in the fiber cladding can be targeted via the implementation of the phase match condition, where $N_{clad,i}^{eff}$ and $N_{core}^{eff}$ are the effective indices of the excited cladding mode with the order of i and input core mode, respectively; $\theta$ is the tilt angle of the TFBG. $\Lambda$ is the period of the grating, $\omega$ is the angular frequency of the light, c is the speed of light in vacuum; $\varepsilon_m$ and $\varepsilon_s$ are the complex relative permittivities of the metal film and the surrounding material adjacent to the metal interface where the SPP is located, respectively. When $\beta_{spp}=\beta_{clad,i}=\omega\cdot N_{clad,i}^{eff}/c$, combined with a proper polarization control, SPR can be achieved. Therefore, any perturbations near the metal layer can be detected by measuring the power changes of the matched cladding modes.

Organic-Inorganic Materials Principle

Figure 21B:
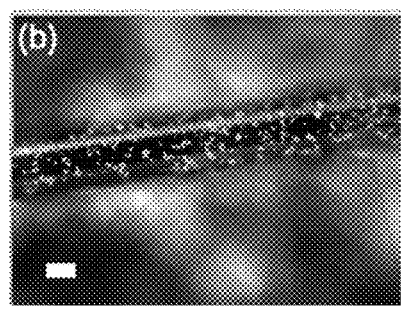
Figure 21C:
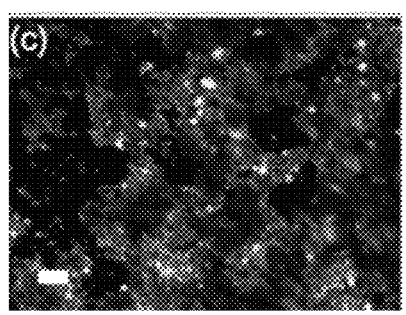
Figure 21D:
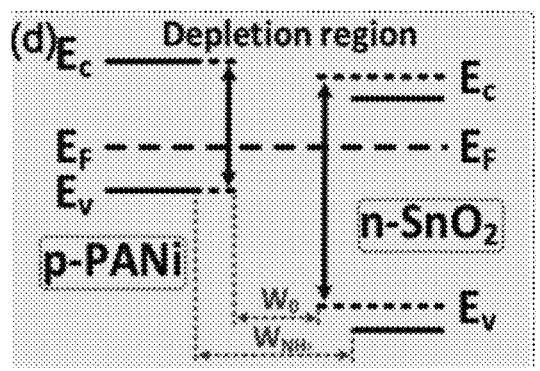

The polyaniline-$SnO_2$ hybrid thin film is one of the most promising materials thanks to its high gas response at room temperature. FIGS. 21B and 21C are two photos of the polyaniline over on the surface of $SnO_2$ taken by microscope, the scale bar are 50 um and 20 um respectively. The Polyaniline serves as a p-type semiconductor, and $SnO_2$ was an n-type semiconductor. So, the hybrid thin film contained the properties of p-n junctions. The n-type $SnO_2$ formed a p-n junction to polyaniline with a depletion region. The physical models of conductive mechanism of polyaniline-$SnO_2$ hybrid thin film upon exposure to $NH_3$ gas (before and after gas) are shown in FIG. 21D. When the composites were exposed to $NH_3$ that acted as a dopant, the depletion region changed, and the resistance of conducting polymer increased continuously. Therefore, the width of the depletion region increased from $W_0$ to $W_{NH3}$, and the conductivity of the polyaniline channel decreased. Hence, permittivity of the composites changed significantly, which made it easy to detect small quantity of $NH_3$ with high response at room temperature.

Experimental System

Figure 22:
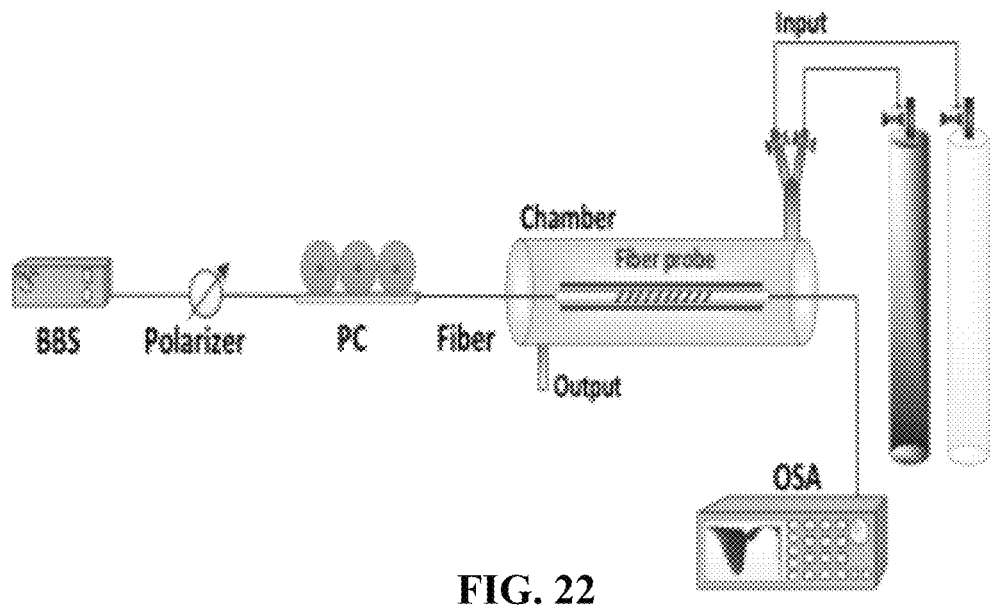
FIG. 22 illustrates a schematic configuration of the ammonia sensing system of this Embodiment 3.

Experimental setup: FIG. 22 depicts the schematic configuration of the ammonia sensing system. The sensing probe placed in the gas chamber providing various concentration of gas. A broadband source (BBS), with the wavelength range matched to the cladding mode and core mode resonance, followed by a linear polarizer, was the light source. The polarization state of the light launched into the TFBG sensor was controlled by a polarization controller (PC) which was adjusted to maximize the coupling of the excited cladding modes to the SPR, ensuring the strongest signal-to-noise ratio. The transmission spectrum from the sensor were monitored and recorded by an optical spectrum analyzer (OSA) with a resolution of 0.02 nm.

Figure 23:
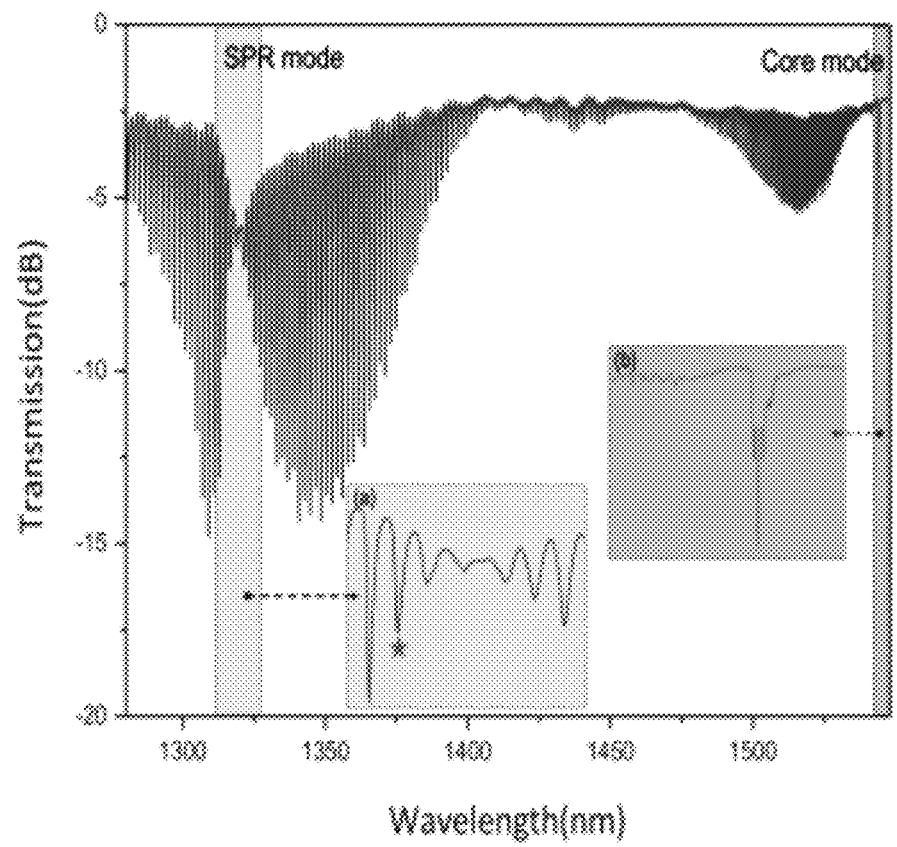
FIG. 23 shows transmission spectrum from the TFBG-SPR sensor: with (a) enlarged detail of the SPR mode resonance region and selected resonance (blue star) for sensing; and (b) enlarged detail of the core Bragg mode.

Sensor interrogation: FIG. 23 shows a typical measured spectrum of the functional material coated plasmonic TFBG ammonia sensor when exposure to air. Two spectral regions were studied during $NH_3$ measurement: the selected SPR mode resonance near 1314 nm, indicated with the blue star see at the inset (a), was monitored for sensing ammonia. At the same time, we monitored the core mode resonance near 1543 nm (see at the inset (b)) for calibrating temperature-induced cross-sensitivity.

Results and Analysis

Figure 24A:
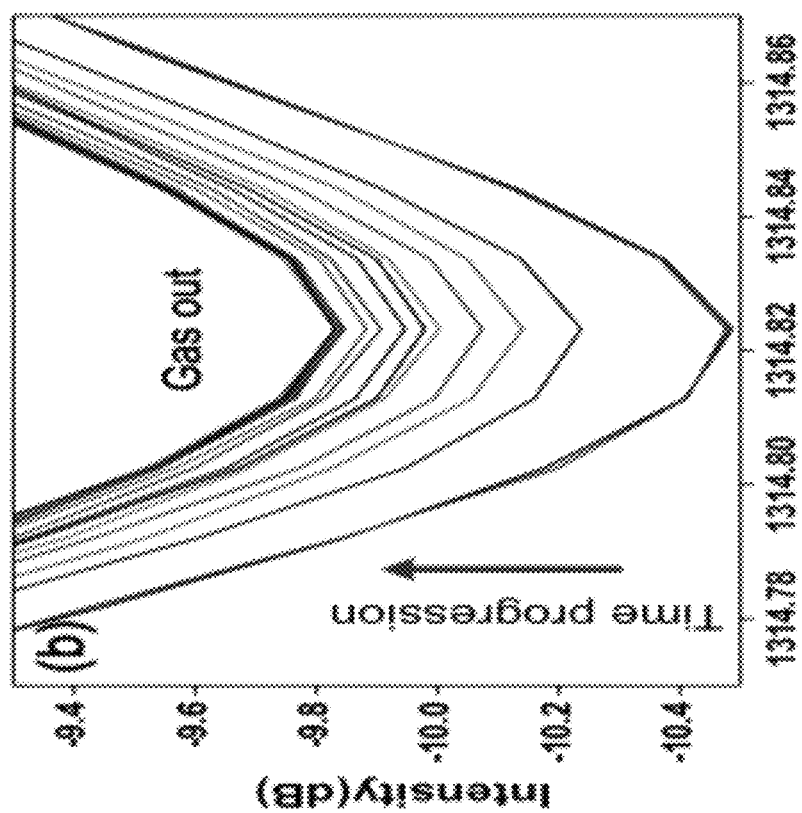
FIGS. 24A and 24B respectively show the intensity response of the selected resonance versus $NH_3$ (FIG. 24A) gas in and (FIG. 24B) gas out.
Figure 24B:
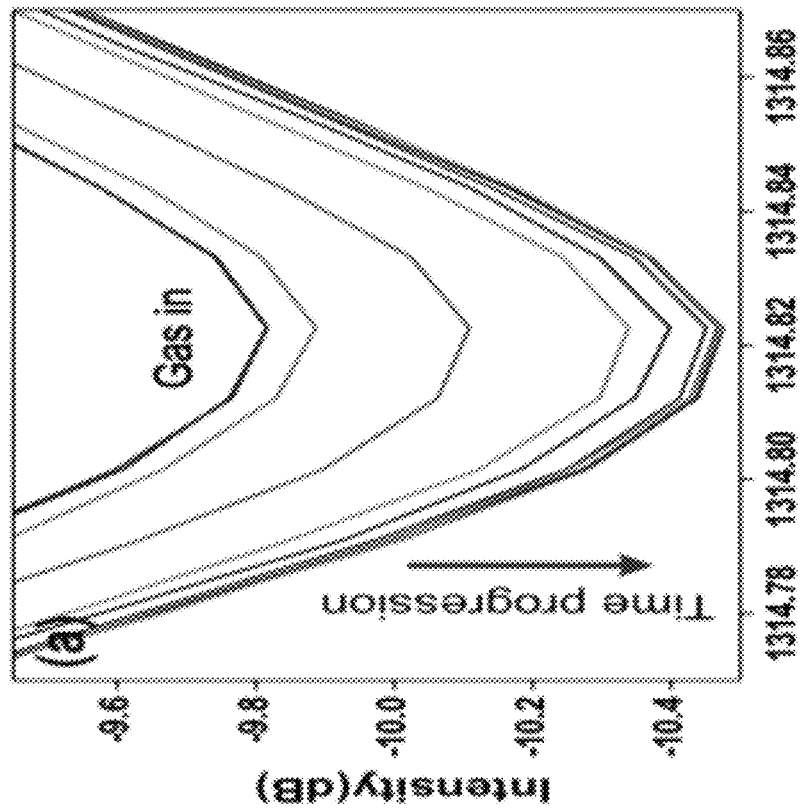
Figure 25:
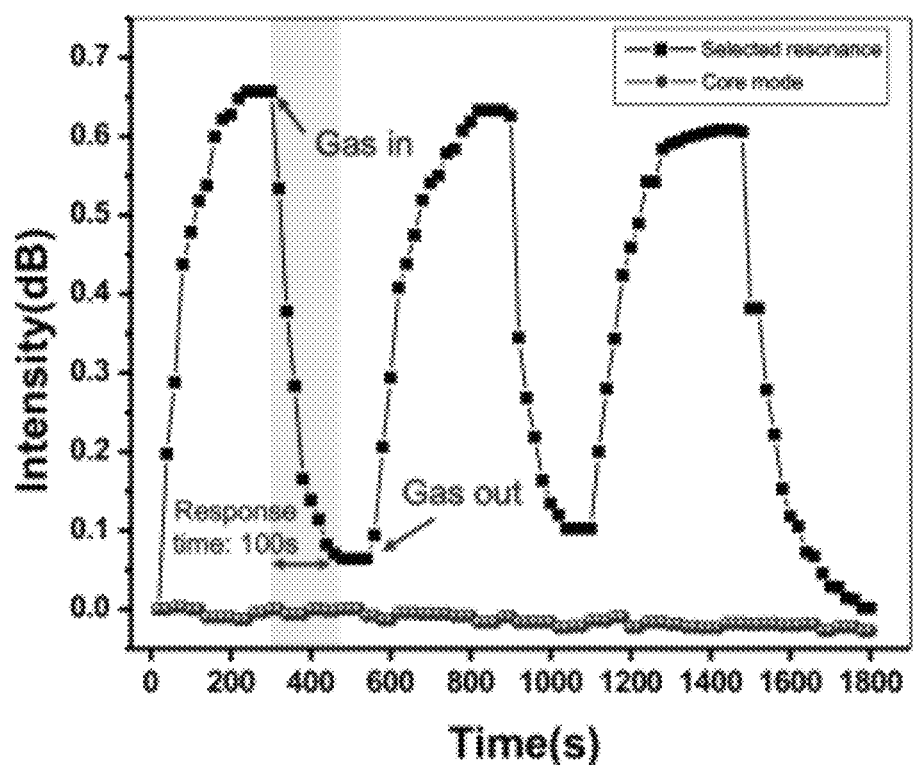
FIG. 25 shows the reversible circulation response change of selected resonance and core mode respectively when $HN_3$ sensor upon exposure to 50 ppm $NH_3$.

Reversibility: FIGS. 24A and 24B present the real-time spectral response of the selected cladding resonance after the sensor exposed on the 50 ppm $NH_3$ and air respectively. As it can be seen, the Intensity of the selected resonance decreases dramatically when it was exposed to $NH_3$ gas. Conversely, that will be increasing when it was exposed to air. As shown in FIG. 25, the results also show that a sensor made from $SnO_2$ film enchased with polyaniline nanograins exhibited an excellent reversibility to $NH_3$ gas. Two determination curves of the response from the first to third exposures to $NH_3$ gas. As it can be seen, for monitoring the intensity change at the center of the selected SPR mode resonance, it is very easy to recover by flushing air through the test chamber at room temperature after the sensor has been exposed to $NH_3$ gas. At the same time, the monitored core mode intensity fluctuates by only 0.03 dB, indicating that the sensor and sensing system are highly stable and surrounding environmentally-induced effects on the measured results can be ignored. In addition, the standard deviation of the mode intensity for a constant $NH_3$ concentration of 50 ppm is ±0.0025 dB. That means that the theoretical limit of detection of this sensor can be estimated to be equivalent to a $NH_3$ concentration value of 2.0 ppm.

Figure 26:
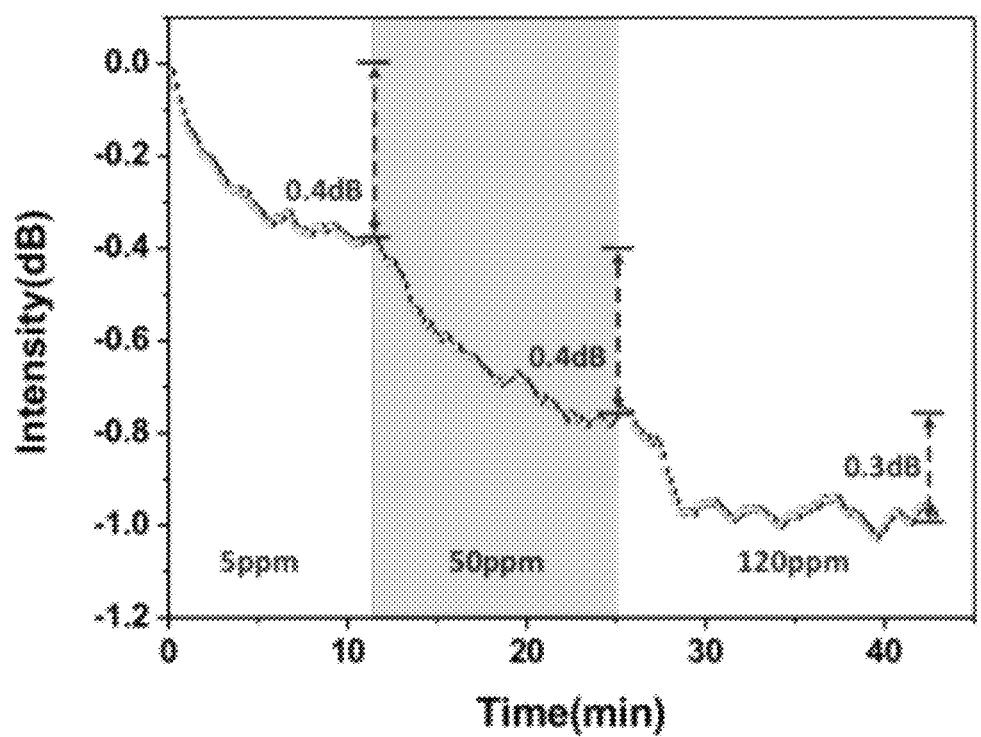
FIG. 26 shows the strength change of the intensity at center of the selected resonance respect to the real time when the sensor upon exposure 5 ppm, 50 ppm, and 120 ppm $NH_3$.
Figure 27:
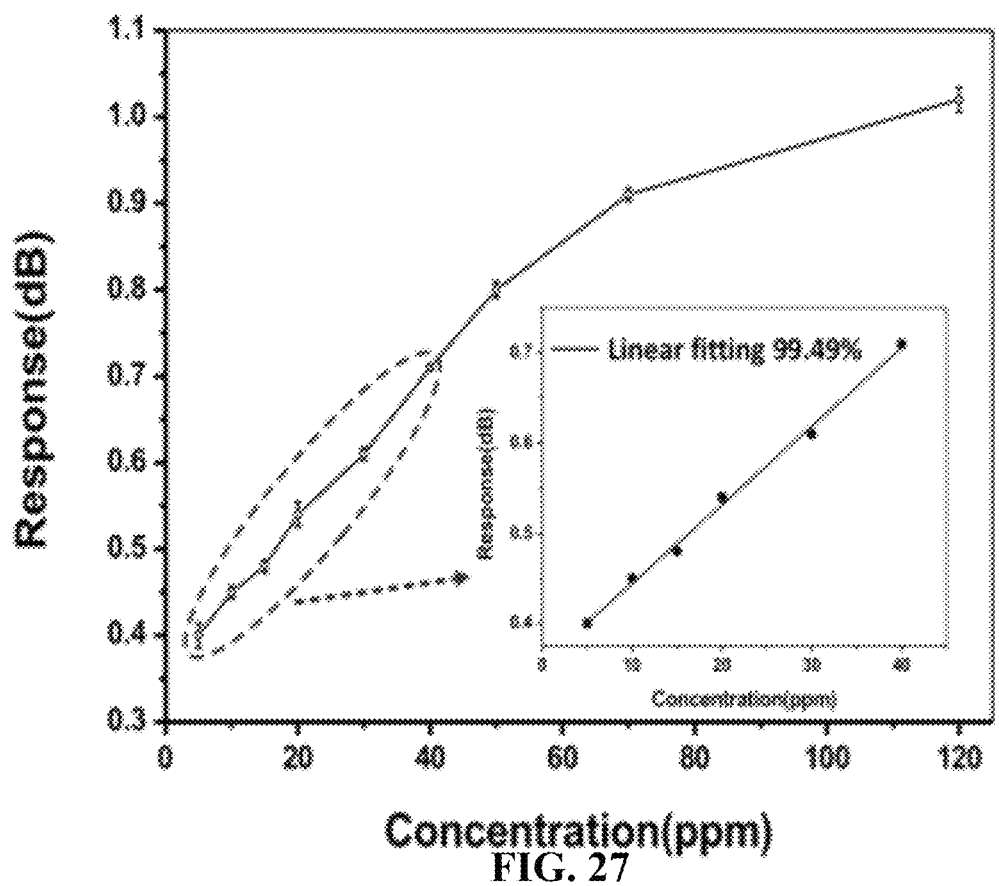
FIG. 27 shows the intensity change of the selected resonance versus various concentration of ammonia from 5 ppm to 120 ppm.

Limit of detection and linear fit: The intensity at the center of the selected resonance versus time is plotted in FIG. 26, the dynamic behaviors of the sensor exposed to different concentrations of $NH_3$ gas. As it can be seen, the strength change of the intensity is very obvious, even though the $NH_3$ concentration in air is as low as 5 ppm. The intensity decreases rapidly during the first 4 minutes and then more or less slowly. And becomes more stable after the sensor has been exposed on 5 ppm $NH_3$ for lasting 10 minutes. After then, the strength change continue decreases when the concentration of $NH_3$ sensor exposed on 50 ppm and 120 ppm. FIG. 27 represents the correlation between intensity change and concentration change of $NH_3$. As $NH_3$ alters induced the surrounding RI, the intensity of the selected resonance changes. When the concentration is below ~40 ppm, the liner fit can be targeted from 5 ppm to 40 ppm (see also inset).

Figure 28:
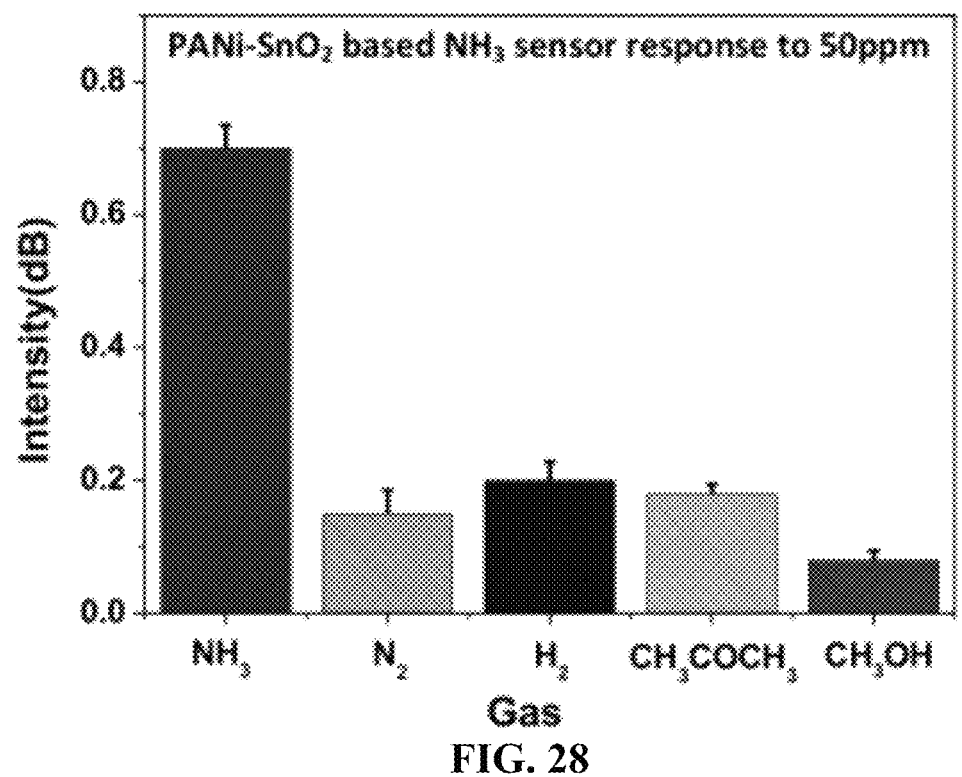
FIG. 28 shows the response change of sensor upon exposure to $NH_3$, $N_2$, $H_2$, $CH_3COCH_3$ and $CH_3OH$.

Selectivity: The gas response characteristic of polyaniline-$SnO_2$ hybrid thin film to $NH_3$, $N_2$, $H_2$, $C_2H_5OH$, $Cl_2$, $NO_2$, $CH_3COCH_3$ and $CH_3OH$ were carried out at room temperature. It was found that polyaniline-$SnO_2$ coated TFBG-SPR sensor could exhibit high response to $NH_3$, but no response to 50 ppm $C_2H_5OH$, $Cl_2$, $NO_2$ and very less response to 50 ppm $CH_3OH$ and $CH_3COCH_3$. The enhanced gas-sensing performance of the polyaniline-$SnO_2$ hybrid thin film is due to the best synergistic effect between the polyaniline and the suitable thickness of $SnO_2$. The responses of polyaniline-$SnO_2$ thin film for 50 ppm to $NH_3$, $N_2$, $H_2$, $CH_3OH$, and $CH_3COCH_3$ at room temperature are shown in FIG. 28. It was observed that the polyaniline-$SnO_2$ thin film showed more selective for $NH_3$ compared to $CH_3COCH_3$ and $CH_3OH$ at room temperature.

Conclusion

A hybrid organic-inorganic functional material (polyaniline-$SnO_2$) thin film based SPR optical fiber sensor (fiber/Au/$SnO_2$/polyaniline) for detection of $NH_3$ has been fabricated. And it can realize detection in room temperature and has highly selective with $NH_3$. The limit of detection achieved 5 ppm and has reproducible property in 50 ppm. The sensor is found to be selective also by measuring the interference with other gases ($CH_3OH$, $C_2H_5OH$, $NH_3$, $Cl_2$ and $NO_2$). The results indicate that trace levels of $NH_3$ (5 ppm to 120 ppm) can be easily and efficiently detected using an plasmonic TFBG sensor coated with an organic-inorganic hybrid material (polyaniline-$SnO_2$).

Embodiment 4

Embodiment 4 provides an optical fiber-based ammonia-sensing apparatus with its coating assembly comprising a gold film layer (50 nm) decorated with $SnO_2$ nanoparticles.

Figure 29:
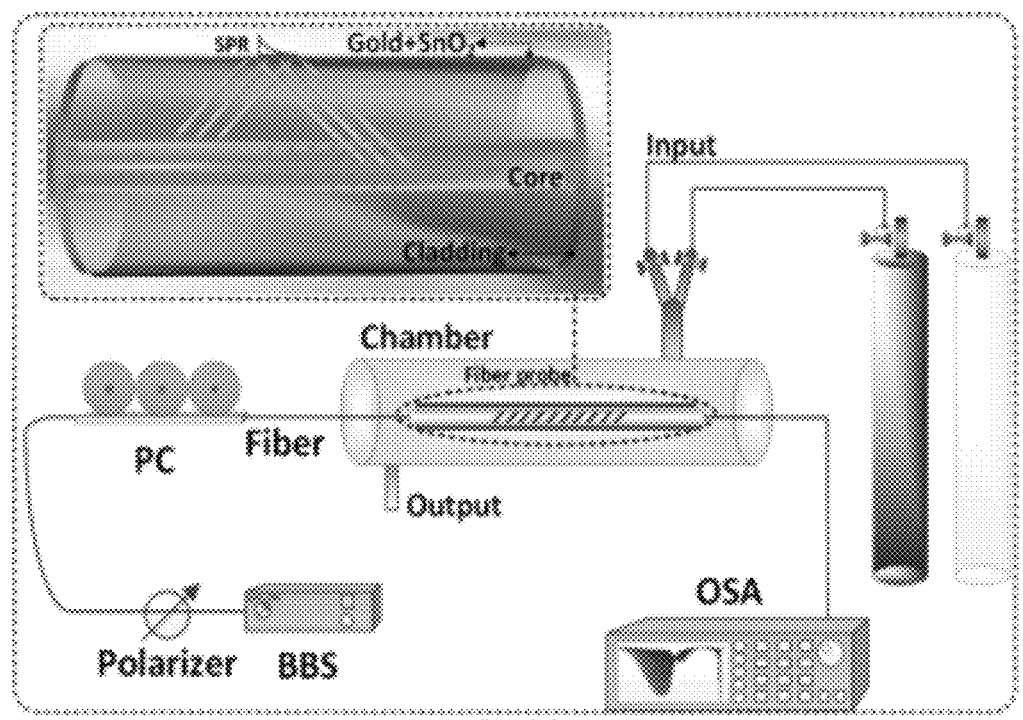
FIG. 29 illustrates a schematic configuration of the ammonia sensing system of this Embodiment 4.

Experimental setup: FIG. 29 depicts the schematic configuration of the ammonia sensing system. The sensing probe placed in the gas chamber providing various concentration of gas. A broadband source (BBS), with the wavelength range matched to the cladding mode and core mode resonance, followed by a linear polarizer, was the light source. The polarization state of the light launched into the TFBG sensor was controlled by a polarization controller (PC) which was adjusted to maximize the coupling of the excited cladding modes to the SPR, ensuring the strongest signal-to-noise ratio. The transmission spectrum from the sensor were monitored and recorded by an optical spectrum analyzer (OSA) with a resolution of 0.02 nm. The BBS then would be replaced by a tunable laser, and the wavelength of the tunable laser would be at the selective SPR mode resonance.

Figure 30:
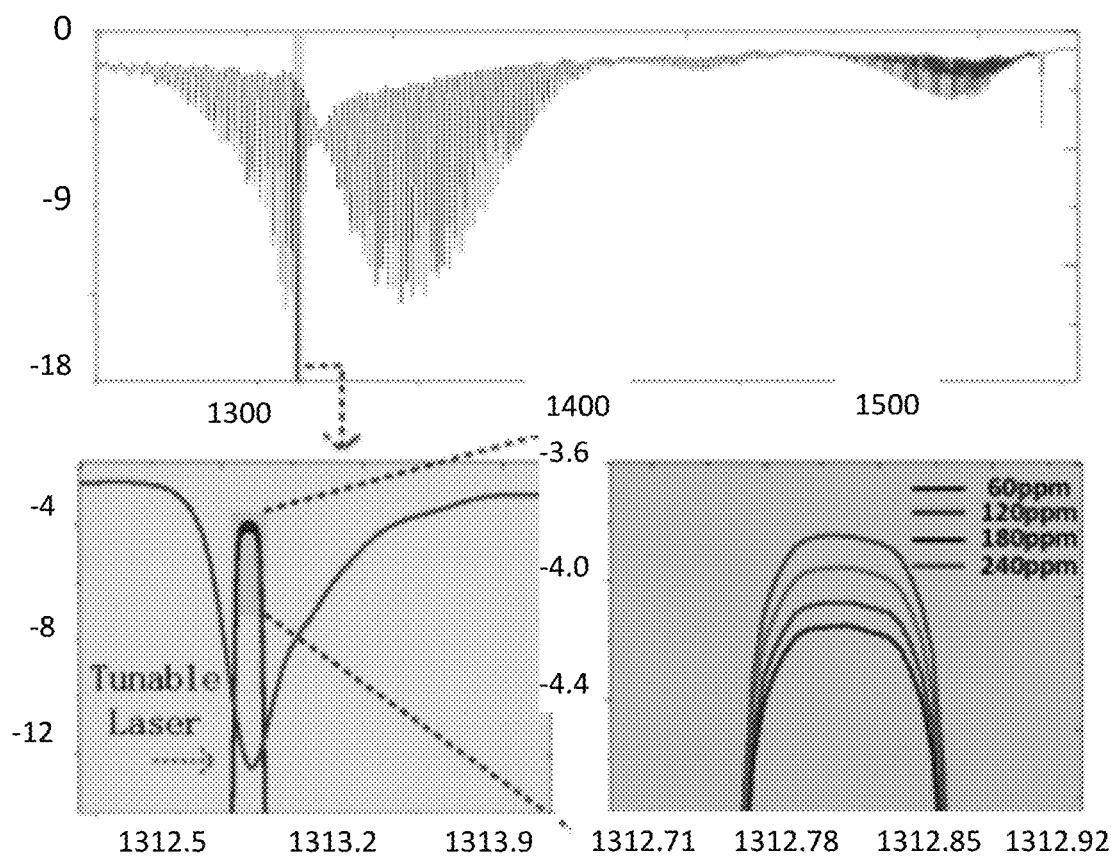
FIG. 30 shows a typical measured spectrum of the functional material coated plasmonic TFBG ammonia sensor when exposure to air.

Sensor interrogation: FIG. 30 shows a typical measured spectrum of the functional material coated plasmonic TFBG ammonia sensor when exposure to air. A tunable laser was used. The wavelength of the laser at the selective SPR mode resonance near 1314 nm was used. The strength of the tunable laser was studied during $NH_3$ measurement: the tunable laser spectrum, see at the lower left and lower right of FIG. 30, was monitored for sensing ammonia.

Figure 31:
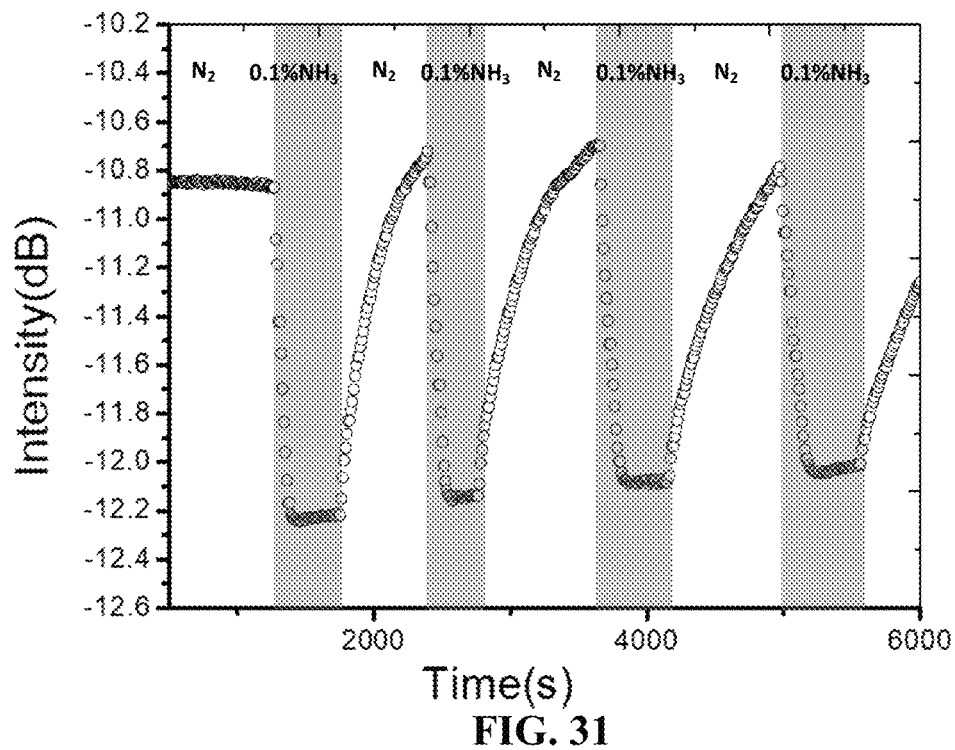
FIG. 31 show the experimental results of the sensor reacts to ammonia leaks with concentration of 0.1%.
Figure 32:
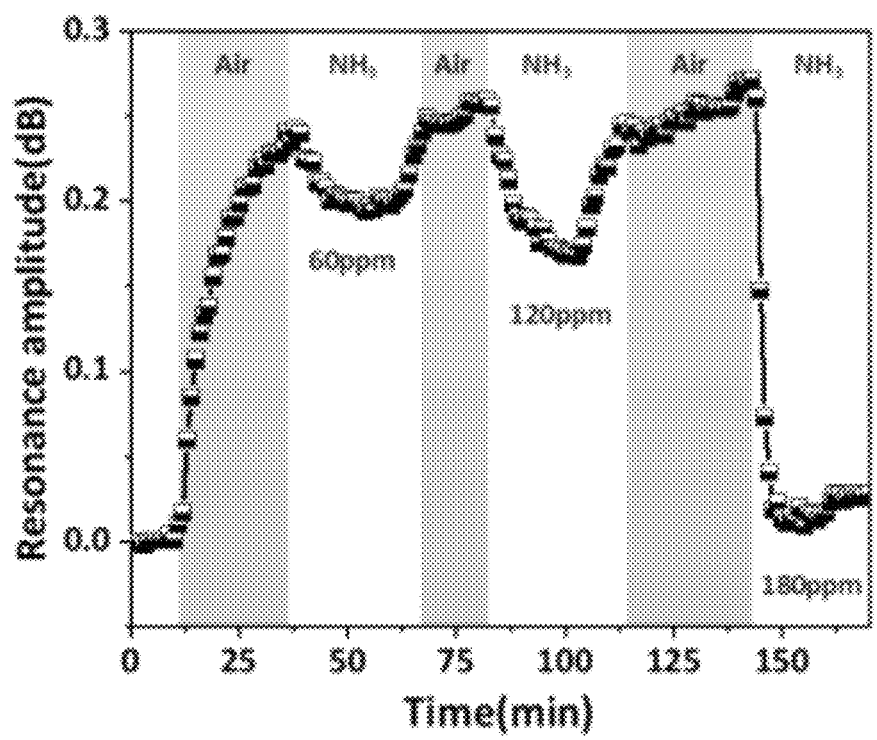
FIG. 32 show that the sensor reacts to ammonia leaks with concentrations of 60 ppm, 120 ppm or 180 ppm in volume.

The results show that with a film of gold layer (50 nm) decorated with $SnO_2$ nanoparticles there is a maximum of light coupling from the cladding modes to the plasmon. A sensor based on a TFBG coated with a layer of these characteristics is fabricated. After that, the performance of the sensor was evaluated when exposing it to different ammonia concentrations in an air atmosphere. The experimental results, see at FIG. 31, show that the sensor reacts to ammonia leaks with concentration of 0.1%. FIG. 32 show that the sensor reacts to ammonia leaks with concentrations of 60 ppm, 120 ppm or 180 ppm in volume. Among the characteristics of the sensor it is worth mentioning a good reversibility, fast response and stabilization times and a low limit of detection. Together with the intrinsic features of optical fibers, these sensors provide a suitable solution for ammonia detection into difficult access.

REFERENCES

Albert J, Shao L Y, Caucheteur C. Tilted fiber Bragg grating sensors. Laser & Photonics Reviews, 2013, 7(1): 83-108.

Bevenot X, Trouillet A, Veillas C, et al. Surface plasmon resonance hydrogen sensor using an optical fibre. Measurement Science and Technology, 2001, 13(1): 118.

Caucheteur, C., Voisin, V., Albert, J., 2015. Near-infrared grating-assisted SPR optical fiber sensors: design rules for ultimate refractometric sensitivity. Optics Express 23, 2918.

Erdogan T, Sipe J E. Tilted fiber phase gratings. Journal of the Optical Society of America A, 1996, 13(2): 296-313.

Guo T, González-Vila Á, Loyez M, et al. Plasmonic optical fiber-grating immunosensing: a review. Sensors, 2017, 17(12): 2732.

Guo, T., 2017. Fiber Grating-Assisted Surface Plasmon Resonance for Biochemical and Electrochemical Sensing. J. Lightwave Technol., JLT 35, 3323-3333.

Guo, T., Liu, F., Guan, B.-O., Albert, J., 2016. Tilted fiber grating mechanical and biochemical sensors. Optics & Laser Technology 78, 19-33.

Johnson, P., Christy, R., 1974. Optical constants of transition metals: Ti, V, Cr, Mn, Fe, Co, Ni, and Pd. Physical Review B 9, 5056-5070.

The invention claimed is:

1. A sensing apparatus for selectively detecting a target molecule in a gaseous medium with a limit of detection of less than 50 ppm, comprising:
    an optical fiber, comprising a core and a cladding surrounding the core, wherein the core is provided with a tilted grating; and
    a coating assembly coating an outside of the cladding; wherein:
        the coating assembly is configured to be active to surface plasmon resonance (SPR), and is further configured to be reversibly reactive to the target molecule to allow for repeated detection with high reproducibility;
        the tilted grating in the core of the optical fiber and the coating assembly is configured to generate surface plasmon waves at an interface between the coating assembly and the gaseous medium upon a compatible electromagnetic radiation propagating in the optical fiber, wherein signals of the surface plasmon waves contain information of the target molecule in the gaseous medium.

2. The sensing apparatus of claim 1, wherein there is at least one range of concentrations for the target molecule allowing the sensing apparatus to have a linear measurement therein.

3. The sensing apparatus of claim 1, wherein the optical fiber is further configured to generate other optical waves in the core upon the compatible electromagnetic radiation propagating in the optical fiber, wherein:
    the sensing apparatus reliably characterizes the target molecule in the gaseous medium with only minimal influence from fluctuations in certain factors based on the signals of the surface plasmon waves and using signals of the other optical waves as an inherent reference.

4. The sensing apparatus of claim 1, wherein the coating assembly comprises:
    a substrate layer coating the cladding of the optical fiber, configured to be active to SPR and insensitive to the target molecule; and
    a reacting layer over an outer surface of the substrate layer, comprising a composition sensitive to the target molecule.

5. The sensing apparatus of claim 4, wherein the target molecule is hydrogen, and the reactive layer comprises palladium (Pd).

6. The sensing apparatus of claim 5, wherein:
    the substrate layer comprises at least one of gold (Au) or silver (Ag), and has a thickness in a range of approximately 20-50 nm; and
    the reactive layer comprises a palladium thin film having a thickness in range of approximately 3-15 nm.

7. The sensing apparatus of claim 6, wherein:
    the substrate layer comprises a gold thin film having a thickness in a range of approximately 25-40 nm;
    the reactive layer comprises a palladium thin film having a thickness in a range of approximately 5-9 nm; and
    the internal tilt angle of the grating is at least approximately 20 degrees.

8. The sensing apparatus of claim 4, wherein the target molecule is ammonia, and the reactive layer has a composition of at least one of:
    an inorganic material, selected from a group consisting of tin oxide ($SnO_2$), zinc oxide (ZnO), tungsten oxide ($WO_3$), titanium oxide ($TiO_2$), and iron oxide ($Fe_2O_3$/$Fe_3O_4$); or
    an organic material, selected from a group consisting of polyaniline, polypyrrole, and metal phthalocyanines.

9. The sensing apparatus of claim 8, wherein:
    the substrate layer comprises a gold thin film having a thickness in a range of approximately 40-60 nm;
    the reactive layer comprises a polyaniline nanocomposite decorated $SnO_2$ thin film having a thickness of approximately 20-30 nm; and
    an internal tilt angle of the grating is at least approximately 20 degrees.

10. The sensing apparatus of claim 1, wherein the coating assembly consists of one single film layer comprising a composition that is both active to SPR and sensitive to the target molecule.

11. The sensing apparatus of claim 10, wherein the target molecule is hydrogen, wherein:
    the coating assembly consists of one single palladium film layer having a thickness in a range of approximately 40-70 nm; and an internal tilt angle of the grating is at least approximately 6 degrees.

12. The sensing apparatus of claim 1, wherein the coating assembly comprises a substrate layer coating the cladding of the optical fiber, configured to be active to SPR and insensitive to the target molecule, and the substrate layer is provided with a modified outer surface exposed to the gaseous medium, configured to sensitive to the target molecule.

13. The sensing apparatus of claim 12, wherein the target molecule is ammonia, wherein:
the substrate layer comprises at least one of gold (Au) or silver (Ag), and has a thickness in a range of approximately 30-70 nm; and
the modified outer surface of the substrate layer comprises $SnO_2$ nanoparticles.

14. A sensing system, comprising:
a sensing apparatus according to claim 1;
a light source apparatus, optically coupled to a first end of, and configured to provide an input light into, the sensing apparatus so as to allow the electromagnetic radiation to propagate in the core of the optical fiber of the sensing apparatus; and
a signal detection apparatus, coupled to the sensing apparatus and configured to obtain the signals of the surface plasmon waves therefrom so as to derive the information of the target molecule in the gaseous medium.

15. The sensing system of claim 14, wherein the light source apparatus comprises a light source, a polarizer, and a polarization controller, sequentially along an optical pathway into the optical fiber of the sensing apparatus, arranged such that the input light emitted from the light source becomes a polarized light having a polarization direction substantially parallel to an inscription direction of the grating in the core of the optical fiber.

16. The sensing system of claim 15, wherein:
the light source comprises a broadband source (BBS); and
the signal detection apparatus comprises an optical spectrum analyzer (OSA).

17. The sensing system of claim 15, wherein:
the light source comprises a tunable laser source (TLS); and
the signal detection apparatus comprises:
an optical detector, configured to detect, and to convert into analog electrical signals, the signals of the plasmon waves from the sensing apparatus; and
an analog-to-digital converter, configured to convert the analog electrical signals into digital electrical signals.

18. The sensing system of claim 14, wherein the signal detection apparatus is coupled to a second end of the optical fiber.

19. The sensing system of claim 18, further comprising at least one other sensing apparatus, each having a second optical fiber, wherein:
the second optical fiber in the each of the at least one other sensing apparatus is optically connected to one another in series and is further connected in series to a beginning end of the optical fiber of the sensing apparatus to thereby share a common electromagnetic radiation propagation pathway; and
the signal detector is configured to differentially obtain signals of the surface plasmon waves from the sensing apparatus and each of the at least one other sensing apparatus.

20. The sensing system of claim 14, wherein the signal detection apparatus is coupled to the first end of the optical fiber, wherein:
a second end of the optical fiber is provided with a mirror having a reflection surface facing to, configured to reflect the electromagnetic radiation back towards, the first end of the optical fiber; and
the sensing system further comprises a coupler, wherein:
the coupler is arranged between the light source apparatus and the sensing apparatus along an input optical pathway and between the sensing apparatus and the signal detection apparatus along an output optical pathway; and
the coupler is configured to separate the input optical pathway and the output optical pathway to thereby allow the signal detection apparatus to obtain the signals of the surface plasmon waves from the sensing apparatus without being influenced by the input light.

21. A method for selectively detecting a target molecule in a gaseous medium, comprising:
providing a sensing system according to claim 14;
exposing the sensing apparatus to the gaseous medium;
switching on the light source apparatus to provide an input light into the sensing apparatus;
obtaining, by means of the signal detection apparatus, signals of surface plasmon waves produced on the interface between the coating assembly and the gaseous medium upon excitement by the input light; and
analyzing the signals of the surface plasmon waves to thereby derive the information of the target molecule in the gaseous medium.

22. The method of claim 21, wherein the obtaining, by means of the signal detection apparatus, signals of surface plasmon waves produced on the interface between the coating assembly and the gaseous medium upon excitement by the input light comprises:
obtaining, by means of the signal detection apparatus, signals of the surface plasmon waves and signals of other optical waves in the core;
wherein:
the analyzing the signals of the surface plasmon waves to thereby derive the information of the target molecule in the gaseous medium comprises:
analyzing the signals of the surface plasmon waves and the signals of the other optical waves to thereby derive the information of the target molecule in the gaseous medium.

23. The method according to claim 21, wherein the light source apparatus comprises a broadband source (BBS), and the signal detection apparatus comprises an optical spectrum analyzer (OSA), wherein:
the switching on the light source apparatus to provide an input light into the sensing apparatus comprises:
switching on the broadband source (BBS) to provide an input light with a broadband into the sensing apparatus; and
the analyzing the signals of the surface plasmon waves comprises:
performing a spectral interrogation over the signals of the surface plasmon waves to quantify a wavelength shift and optical intensity change induced by a refractive index change of the sensing apparatus so as to derive information of the target molecule in the gaseous medium.

24. The method according to claim 21, wherein in the providing a sensing system, the sensing apparatus is determined to have a first wavelength of light that, upon being inputted into the sensing apparatus, produces a most sensitive mode of the plasmon waves, the light source apparatus comprises a tunable laser (TLS), and the signal detection apparatus comprises an optical detector and an analog-to-digital converter, wherein:

the switching on the light source apparatus to provide an input light into the sensing apparatus comprises:
    switching on the tunable laser (TLS) such that an input light having a second wavelength matching the first wavelength is produced and emits into the sensing apparatus;
  the obtaining, by means of the signal detection apparatus, signals of surface plasmon waves comprises:
    converting, by means of the optical detector, the signals of the surface plasmon waves from the sensing apparatus into analog electrical signals; and
    converting, by means of the analog-to-digital converter, the analog electrical signals into digital electrical signals; and
  the analyzing the signals of the surface plasmon waves to thereby derive the information of the target molecule in the gaseous medium comprises:
    performing an interrogation over a quantification of intensity variations based on the digital electrical signals to thereby derive the information of the target molecule in the gaseous medium.

25. The method according to claim 21, wherein in the providing a sensing system, the sensing system comprises more than one sensing apparatus, optically connected to one another in series and each comprising an optical fiber sharing a common electromagnetic radiation propagation pathway, wherein:
  the obtaining, by means of the signal detection apparatus, signals of surface plasmon waves produced on the interface between the coating assembly and the gaseous medium upon excitement by the input light comprises:
    differentially obtaining, by means of the signal detection apparatus, signals of surface plasmon waves from each of the more than one sensing apparatus; and
  the analyzing the signals of the surface plasmon waves comprises:
differentially analyzing the signals of the surface plasmon waves from the each of the more than one sensing apparatus.

* * * * *